US010927300B2

(12) United States Patent
Kimura et al.

(10) Patent No.: US 10,927,300 B2
(45) Date of Patent: Feb. 23, 2021

(54) SPONTANEOUS ALIGNMENT ASSISTANT FOR LIQUID CRYSTAL COMPOSITIONS

(71) Applicant: DIC Corporation, Tokyo (JP)

(72) Inventors: Masaomi Kimura, Kita-adachi-gun (JP); Yuuichi Inoue, Kita-adachi-gun (JP); Hidenari Akiyama, Kita-adachi-gun (JP); Masanao Hayashi, Kita-adachi-gun (JP); Tetsuo Kusumoto, Kita-adachi-gun (JP)

(73) Assignee: DIC CORPORATION, Tokyo (JP)

( * ) Notice: Subject to any disclaimer, the term of this patent is extended or adjusted under 35 U.S.C. 154(b) by 0 days.

(21) Appl. No.: 16/340,798

(22) PCT Filed: Oct. 17, 2017

(86) PCT No.: PCT/JP2017/037481

§ 371 (c)(1),
(2) Date: Apr. 10, 2019

(87) PCT Pub. No.: WO2018/079333

PCT Pub. Date: May 3, 2018

(65) Prior Publication Data

US 2019/0264108 A1 Aug. 29, 2019

(30) Foreign Application Priority Data

Oct. 26, 2016 (JP) ............................ JP2016-209592
Jun. 1, 2017 (JP) ............................ JP2017-109171

(51) Int. Cl.
*C09K 19/56* (2006.01)
*C07C 69/54* (2006.01)
(Continued)

(52) U.S. Cl.
CPC .............. *C09K 19/56* (2013.01); *C07C 69/54* (2013.01); *C07C 69/612* (2013.01);
(Continued)

(58) Field of Classification Search
CPC ........ C09K 19/56; C09K 19/14; C09K 19/12; C09K 19/30; C09K 19/3405;
(Continued)

(56) References Cited

U.S. PATENT DOCUMENTS

2014/0138581 A1 5/2014 Archetti et al.
2015/0252265 A1 9/2015 Archetti et al.
2017/0210994 A1 7/2017 Lim et al.

FOREIGN PATENT DOCUMENTS

JP 2014-524951 A 9/2014
JP 2015-168826 A 9/2015

OTHER PUBLICATIONS

International Search Report dated Jan. 16, 2018, issued in counterpart International Application No. PCT/JP2017/037481 (3 pages).

*Primary Examiner* — Ruiyun Zhang
(74) *Attorney, Agent, or Firm* — Westerman, Hattori, Daniels & Adrian, LLP

(57) ABSTRACT

The spontaneous orientation aid for a liquid crystal composition provides storage stability and allows liquid crystal molecules to be vertically aligned without a PI layer when added to a liquid crystal composition. The spontaneous orientation aid for a liquid crystal composition includes a compound having a partial structure represented by formula (i), particularly in which $K^{i1}$ is represented by one of formula (K-1) to formula (K-11). When used in a liquid crystal composition, the spontaneous orientation aid can adsorb to substrates sandwiching a liquid crystal composition (liquid crystal layer) and keep the liquid crystal molecules aligned in a vertical direction. The spontaneous orientation aid makes it possible to align liquid crystal molecules without a PI layer (to induce vertical alignment of liquid crystal molecules under no applied voltage and to achieve horizontal alignment of the liquid crystal molecules under an applied voltage).

12 Claims, 2 Drawing Sheets

(51) Int. Cl.

| | |
|---|---|
| ***C07C 69/612*** | (2006.01) |
| ***C07D 317/64*** | (2006.01) |
| ***C07D 319/06*** | (2006.01) |
| ***C09K 19/20*** | (2006.01) |
| ***C09K 19/34*** | (2006.01) |
| ***C09K 19/14*** | (2006.01) |
| ***G02F 1/139*** | (2006.01) |
| ***C07D 309/30*** | (2006.01) |
| ***G02F 1/13*** | (2006.01) |
| ***C07D 309/32*** | (2006.01) |
| ***C07D 305/06*** | (2006.01) |
| ***C09K 19/12*** | (2006.01) |
| ***C09K 19/30*** | (2006.01) |
| ***G02F 1/1337*** | (2006.01) |
| ***C07D 309/06*** | (2006.01) |
| *G02F 1/1362* | (2006.01) |

(52) U.S. Cl.

CPC ......... *C07D 305/06* (2013.01); *C07D 309/06* (2013.01); *C07D 309/30* (2013.01); *C07D 309/32* (2013.01); *C07D 317/64* (2013.01); *C07D 319/06* (2013.01); *C09K 19/12* (2013.01); *C09K 19/14* (2013.01); *C09K 19/2007* (2013.01); *C09K 19/30* (2013.01); *C09K 19/3402* (2013.01); *C09K 19/3405* (2013.01); *G02F 1/13* (2013.01); *G02F 1/139* (2013.01); *G02F 1/1337* (2013.01); *C09K 2019/3422* (2013.01); *C09K 2323/00* (2020.08); *C09K 2323/02* (2020.08); *G02F 1/1362* (2013.01)

(58) Field of Classification Search

CPC .... C09K 2019/3422; C09K 2019/0448; C09K 2323/00; C09K 2323/02; G02F 1/13; G02F 1/1337; G02F 1/133703; G02F 2001/133765; G02F 2001/133742; G02F 2001/139; Y10T 428/10; Y10T 428/1005

USPC ........ 428/1.1, 1.2; 349/182, 191; 252/299.6, 252/299.61, 299.01, 299.4

See application file for complete search history.

SPONTANEOUS ALIGNMENT ASSISTANT FOR LIQUID CRYSTAL COMPOSITIONS

TECHNICAL FIELD

The present invention relates to a spontaneous orientation aid for a liquid crystal composition, a liquid crystal composition, and a liquid crystal display element.

BACKGROUND ART

In related art, in a VA type liquid crystal display, a polyimide alignment film (PI) layer is provided on an electrode, in order to induce a vertical alignment of liquid crystal molecules, in a case where a voltage is not applied, and to realize a horizontal alignment of the liquid crystal molecules, in a case where a voltage is applied. However, the large cost is necessary for forming a PI layer, and accordingly, in recent years, a method for realizing alignment of liquid crystal molecules while omitting the PI layer is researched.

For example, PTL 1 discloses a liquid crystal medium including at least one kind of spontaneous alignment additives, on the basis of a mixture of polar compounds having negative dielectric anisotropy, and discloses that this liquid crystal medium is highly suitable for a use in a display not including an alignment layer at all. In PTL 1, a specific compound including a hydroxyl group is used as the spontaneous alignment additive.

CITATION LIST

Patent Literature

PTL 1: JP-T-2014-524951

SUMMARY OF INVENTION

Technical Problem

However, studies conducted by the inventors have revealed that when the spontaneous alignment additive disclosed in PTL 1 is used, the alignment regulating force for vertically aligning liquid crystal molecules is not sufficient and that the liquid crystal composition containing the spontaneous alignment additive has room for improvement in storage stability.

Therefore, an object of the invention is to provide a spontaneous orientation aid for a liquid crystal composition, which provides storage stability when added to a liquid crystal composition and allows vertical alignment of liquid crystal molecules without a PI layer. Another object of the invention is to provide a liquid crystal composition containing such a spontaneous orientation additive that provides excellent storage stability and allows vertical alignment of liquid crystal molecules without a PI layer, and to provide a liquid crystal display element produced using such a liquid crystal composition.

Solution to Problem

The invention provides a spontaneous orientation aid for a liquid crystal composition, including one or more compounds each having a mesogenic group substituted with: $P^{i1}$-$Sp^{i1}$-, wherein $P^{i1}$ represents a polymerizable group and represents a substituent selected from the group consisting of substituents represented by general formula (P-1) to general formula (P-15) in which each black point on a right end represents atomic bonding,

[Chem. 1]

(P-1)

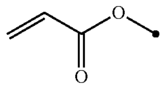

(P-2)

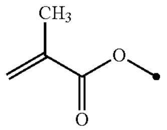

(P-3)

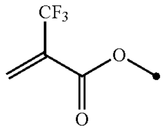

(P-4)

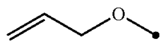

(P-5)

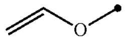

(P-6)

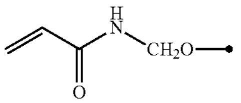

(P-7)

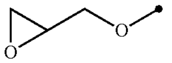

(P-8)

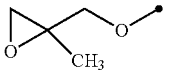

(P-9)

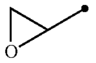

(P-10)

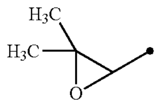

(P-11)

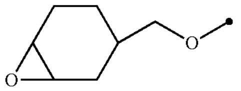

(P-12)

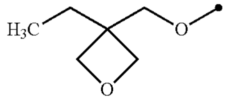

(P-13)

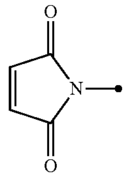

-continued (P-14)

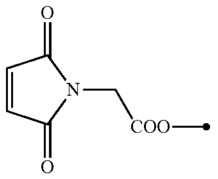

(P-15)

HS—• and $Sp^{i1}$ represents a spacer group; a monovalent organic group having a substituent represented by $K^{i1}$, wherein $K^{i1}$ represents a substituent represented by one of general formula (K-1) to general formula (K-11)); and $R^{i1}$ representing a hydrogen atom, a linear or branched alkyl group having 1 to 40 carbon atoms, a halogenated alkyl group, or $P^{i1}$-$Sp^{i1}$-, wherein —$CH_2$— in the alkyl group may be replaced with —CH═CH—, —C≡C—, —O—, —NH—, —COO—, or —OCO—, provided that —O— moieties are not bonded in series, wherein at least one $P^{i1}$-$Sp^{i1}$- is bonded to the mesogen from the lateral side with respect to the long axis of the mesogen.

[Chem. 2]

(K-1)

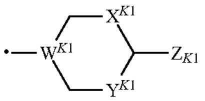

(K-2)

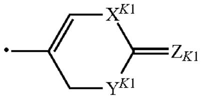

(K-3)

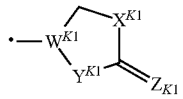

(K-4)

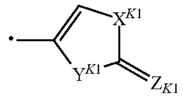

(K-5)

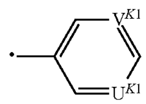

(K-6)

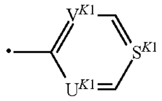

(K-7)

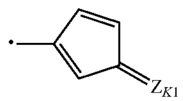

(K-8)

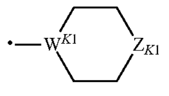

-continued (K-9)

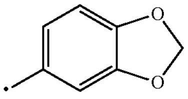

(K-10)

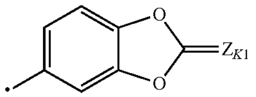

(K-11)

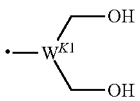

In the formulae, $W^{K1}$ represents a methine group, C—$CH_3$, C—$C_2H_5$, or a nitrogen atom, $X^{K1}$ and $Y^{K1}$ each independently represent —$CH_2$—, an oxygen atom, or a sulfur atom, $Z^{K1}$ represents an oxygen atom or a sulfur atom, $U^{K1}$, $V^{K1}$, and $S^{K1}$ each independently represent a methine group or a nitrogen atom, exclusive of a combination of (K-5) and (K-6) forming a pyridine ring, and each black point on the left end represents atomic bonding, provided that when $K^{i1}$ is (K-11), the mesogenic group includes one of —$CH_2$—$CH_2COO$—, —$OCOCH_2$—$CH_2$—, —CH═C($CH_3$)COO—, —OCOC($CH_3$)═CH, —$CH_2$—CH($CH_3$)COO—, —OCOCH($CH_3$)—$CH_2$—, and —$OCH_2CH_2O$—)

In addition, the invention further provides a liquid crystal composition having negative dielectric anisotropy (Δε) and including one or more compounds each having a partial structure defined for the spontaneous orientation aid for a liquid crystal composition.

Advantageous Effects of Invention

The invention makes it possible to provide a liquid crystal composition containing a spontaneous orientation additive that provides excellent storage stability and allows vertical alignment of liquid crystal molecules without a PI layer, and to provide a liquid crystal display element produced using such a liquid crystal composition.

Figure 1:
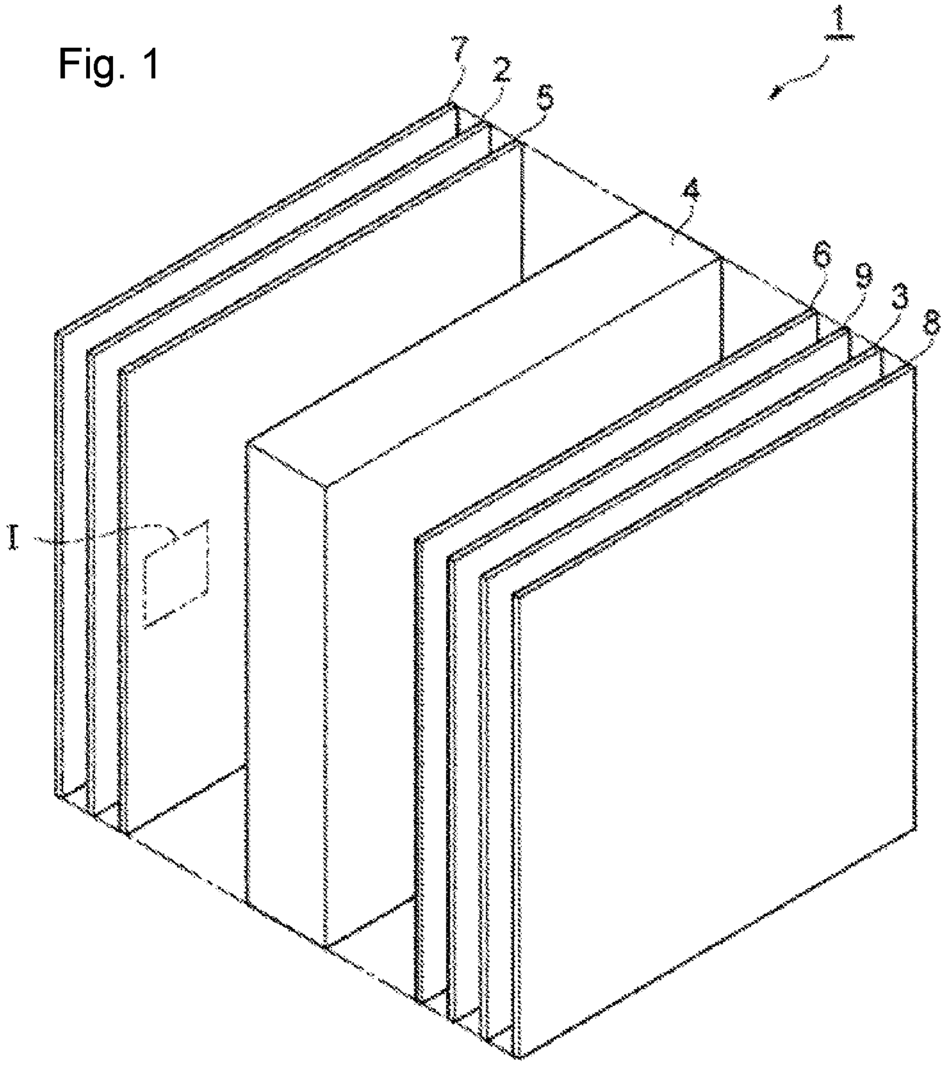
FIG. 1 is a view schematically showing one embodiment of a liquid crystal display element.

DESCRIPTION OF EMBODIMENTS (Spontaneous Orientation Aid for Liquid Crystal Composition)

The spontaneous orientation aid for a liquid crystal composition according to the embodiment includes one or more compounds each having a mesogenic group substituted with: $P^{i1}$-$Sp^{i1}$-, wherein $P^{i1}$ represents a polymerizable group and represents a substituent selected from the group consisting of substituents represented by general formula (P-1) to general formula (P-15) in which a black point on the right end represents atomic bonding,

[Chem. 3]

(P-1)

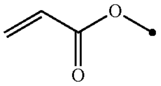

(P-2)

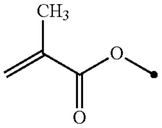

(P-3)

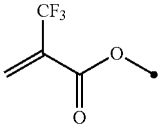

(P-4)

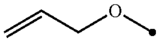

(P-5)

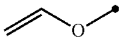

(P-6)

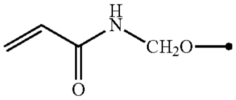

(P-7)

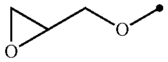

(P-8)

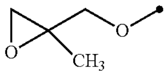

(P-9)

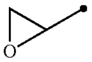

(P-10)

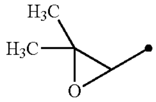

(P-11)

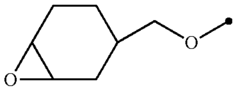

(P-12)

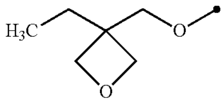

(P-13)

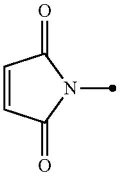

-continued (P-14)

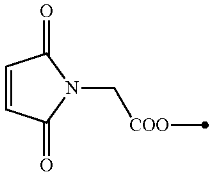

(P-15)

HS—• and $Sp^{i1}$ represents a spacer group; a monovalent organic group having a substituent represented by $K^{i1}$, wherein $K^{i1}$ represents a substituent represented by one of general formula (K-1) to general formula (K-11); and $R^{i1}$ representing a hydrogen atom, a linear or branched alkyl group having 1 to 40 carbon atoms, a halogenated alkyl group, or $P^{i1}$-$Sp^{i1}$-, wherein $—CH_2—$ in the alkyl group may be replaced with —CH═CH—, —C≡C—, —O—, —NH—, —COO—, or —OCO—, provided that —O— moieties are not bonded in series, wherein at least one $P^{i1}$-$Sp^{i1}$- is bonded to the mesogen from the lateral side with respect to the long axis of the mesogen.

[Chem. 4]

(K-1)

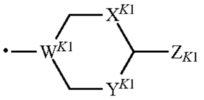

(K-2)

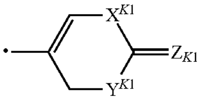

(K-3)

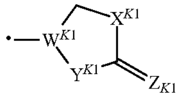

(K-4)

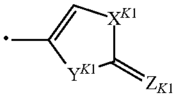

(K-5)

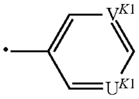

(K-6)

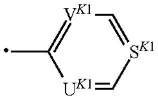

(K-7)

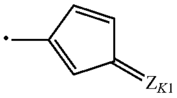

(K-8)

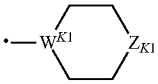

-continued (K-9)

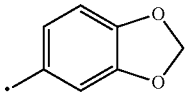

(K-10)

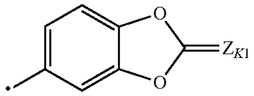

(K-11)

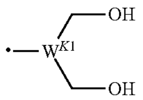

In the formulae, $W^{K1}$ represents a methine group, $C—CH_3$, $C—C_2H_5$, or a nitrogen atom, $X^{K1}$ and $Y^{K1}$ each independently represent $—CH_2—$, an oxygen atom, or a sulfur atom, $Z^{K1}$ represents an oxygen atom or a sulfur atom, $U^{K1}$, $V^{K1}$, and $S^{K1}$ each independently represent a methine group or a nitrogen atom, exclusive of a combination of (K-5) and (K-6) forming a pyridine ring, and each black point on the left end represents atomic bonding, provided that when $K^{i1}$ is (K-11), the mesogenic group contains one of $—CH_2—CH_2COO—$, $—OCOCH_2—CH_2—$, $—CH{=}C(CH_3)COO—$, $—OCOC(CH_3){=}CH—$, $—CH_2—CH(CH_3)COO—$, $—OCOCH(CH_3)—CH_2—$, and $—OCH_2CH_2O—$.

The mesogenic group has a partial structure represented by general formula (i):

[Chem. 5]

$$\bullet\!\!-\!\!\left(A^{i1}-Z^{i1}\right)_{m^{i1}}\!\!-\!\!\bullet \qquad \text{(i)}$$

In the formula, $Z^{i1}$ represents a single bond, $—CH{=}CH—$, $—CF{=}CF—$, $—C{\equiv}C—$, $—COO—$, $—OCO—$, $—OCOO—$, $—OOCO—$, $—CF_2O—$, $—OCF_2—$, $—CH{=}CHCOO—$, $—OCOCH{=}CH—$, $—CH_2—CH_2COO—$, $—OCOCH_2—CH_2—$, $—CH{=}C(CH_3)COO—$, $—OCOC(CH_3){=}CH—$, $—CH_2—CH(CH_3)COO—$, $—OCOCH(CH_3)—CH_2—$, $—OCH_2CH_2O—$, or an alkylene group having 2 to 20 carbon atoms, one or two or more $—CH_2—$'s not adjacent to each other in this alkylene group may be substituted with $—O—$, $—COO—$, or $—OCO$, provided that when $K^{i1}$ is (K-11), the mesogenic group includes one of $—CH_2—CH_2COO—$, $—OCOCH_2—CH_2—$, $—CH{=}C(CH_3)COO—$, $—OCOC(CH_3){=}CH—$, $—CH_2—CH(CH_3)COO—$, $—OCOCH(CH_3)—CH_2—$, and $—OCH_2CH_2O—$, $A^{i1}$ represents a divalent 6-membered ring aromatic group, a divalent 6-membered ring heteroaromatic group, a divalent 6-membered ring aliphatic group, or a divalent 6-membered ring heteroaliphatic group, hydrogen atoms in these ring structures may be substituted with a halogen atom, $P^{i1}$-$Sp^{i1}$-, a monovalent organic group having a substituent represented by general formula $K^{i1}$, or $R^{i1}$, provided that at least one is substituted with $P^{i1}$-$Sp^{i1}$- and when a plurality of $Z^{i1}$'s or $A^{i1}$'s are present, these may be the same or different, $m^{i1}$ represents an integer of 1 to 5. In the formula (i), the black point on the left end and the black point on the right end represent atomic bonding. The spontaneous orientation aid includes at least one compound having such a partial structure (hereinafter also referred to as the "compound (i)").

The spontaneous orientation aid for a liquid crystal composition of the embodiment includes a compound having a partial structure represented by formula (i), particularly, a structure in which $K^{i1}$ in formula (i) is represented by any of formula (K-1) to formula (K-11). Thus, when used in a liquid crystal composition, the spontaneous orientation aid can adsorb to substrates sandwiching the liquid crystal composition (liquid crystal layer) and keep the liquid crystal molecules aligned in the vertical direction. Therefore, the spontaneous orientation aid for a liquid crystal composition of the embodiment makes it possible to vertically align the liquid crystal molecules without a PI layer (to induce vertical alignment of the liquid crystal molecules under no applied voltage and to achieve horizontal alignment of the liquid crystal molecules under an applied voltage). Thus, the compound (i) is suitable for use in aiding the spontaneous orientation of the liquid crystal molecules in the liquid crystal composition.

In addition, the inventors have found that the spontaneous orientation aid for a liquid crystal composition according to the embodiment, which includes the compound having a partial structure represented by formula (i), not only allows alignment of liquid crystal molecules but also provides storage stability for a liquid crystal composition. In a case where chemical stability is important for the spontaneous orientation aid, $K^{i1}$ is preferably (K-1), (K-3), (K-8), (K-9), (K-10), and (K-11), in a case where the liquid crystal alignment is important, $K^{i1}$ is preferably (K-1), (K-3), and (K-11), in a case where solubility to a liquid crystal compound is important, $K^{i1}$ is preferably (K-1), (K-8), and (K-10), and in a case where the balance between these is important, $K^{i1}$ is more preferably (K-1), (K-3), and (K-11). In addition, from viewpoints of chemical stability and polymerization sensitivity, $P^{i1}$ is preferably any substituent of formulae (P-1), (P-2), (P-7) to (P-10), and (P-12), and from a viewpoint of simple handling, $P^{i1}$ is more preferably formulae (P-1), (P-2), (P-9), and (P-10).

From the viewpoints described above, the compound in the spontaneous orientation aid for a liquid crystal composition according to the embodiment may have a partial structure represented by formula (i) at a terminal of the molecule, preferably a terminal of the main chain of the molecule, and the chemical structure of a portion to be bonded to the partial structure represented by formula (i) is not particularly limited, as long as the function of the liquid crystal composition is not inhibited. The compound in the spontaneous orientation aid for a liquid crystal composition according to the embodiment may be, for example, a compound represented by general formula (ii) (hereinafter, also referred to as a "compound (ii)"):

[Chem. 6]

$$R^{ii1}\!-\!\left(A^{ii1}-Z^{ii1}\right)_{m^{ii1}}\!-\!R^{ii2} \qquad \text{(ii)}$$

In the formula, $Z^{ii1}$, $A^{ii1}$, and $m^{ii1}$ each have the same meaning as $Z^{i1}$, $A^{i1}$, and $m^{i1}$ in general formula (i), $R^{ii1}$ and $R^{ii2}$ each independently represent a hydrogen atom, a linear or branched alkyl group having 1 to 40 carbon atoms, a halogenated alkyl group, or $P^{i1}$-$Sp^{i1}$-, wherein $—CH_2—$ in the alkyl group may be substituted with $—CH{=}CH—$, $—C{\equiv}C—$, $—NH—$, $—COO—$, or $—OCO—$, provided that $—O—$ moieties are not bonded in series, at least one of $R^{ii1}$ and $R^{ii2}$ represents a monovalent organic group having a substituent represented by $K^{i1}$, and general formula (ii) has one or two or more $P^{i1}$-$Sp^{i1}$-'s, one or two or more monovalent organic groups including a substituent represented by $K^{i1}$, and one or more $R^{i1}$'s, provided that when $K^{i1}$ is (K-11), $Z^{ii1}$ is any one of —$CH_2$—$CH_2COO$—, —$OCOCH_2$—$CH_2$—, —$CH_2$—$CH(CH_3)COO$—, —$OCOCH(CH_3)$—$CH_2$—, and —$OCH_2CH_2O$—.

In formula (i) and formula (ii), $Z^{i1}$ represents a single bond or a group substituted with —CH═CH—, —C≡—, —COO—, —OCO—, —OCOO—, —OOCO—, —CH═CHCOO—, —OCOCH═CH—, —$CH_2$—$CH_2COO$—, —$OCOCH_2$—$CH_2$—, —CH═$C(CH_3)COO$—, —$OCOC(CH_3)$═CH—, —$CH_2$—$CH(CH_3)COO$—, —$OCOCH(CH_3)$—$CH_2$—, —$OCH_2CH_2O$—, a linear or branched alkylene group having 1 to 40 carbon atoms, or a group in which one or two or more —$CH_2$—'s not adjacent to each other in the alkylene group are replaced with —O—, preferably represents a single bond, —COO—, —OCO—, —CH═CHCOO—, —OCOCH═CH—, —$CH_2$—$CH_2COO$—, —$OCOCH_2$—$CH_2$—, —CH═$C(CH_3)COO$—, —$OCOC(CH_3)$═CH—, —$CH_2$—$CH(CH_3)COO$—, —$OCOCH(CH_3)$—$CH_2$—, —$OCH_2CH_2O$—, a linear or branched alkylene group having 1 to 40 carbon atoms, or a group in which one or two or more —$CH_2$—'s not adjacent to each other in the alkylene group are replaced with —O—, or a single bond, a linear alkylene group having 2 to 15 carbon atoms, or a group in which one or two or more —$CH_2$—'s not adjacent to each other in the alkylene group are replaced with —O—, and more preferably represents a single bond, $CH_2$—$CH_2COO$—, —$OCOCH_2$—$CH_2$—, —CH═$C(CH_3)COO$—, —$OCOC(CH_3)$═CH—, —$CH_2$—$CH(CH_3)COO$—, —$OCOCH(CH_3)$—$CH_2$—, —$OCH_2CH_2O$—, an alkylene group (ethylene group (—$CH_2CH_2$—)) having 2 carbon atoms, a group in which one —$CH_2$— in the ethylene group is replaced with —O— (—$CH_2O$—, —$OCH_2$—), a linear alkylene group having 3 to 13 carbon atoms, or a group in which one or two or more —$CH_2$—'s not adjacent to each other in the alkylene group are replaced with —O—.

$A^{i1}$ preferably represents a divalent 6-membered ring aromatic group or a divalent 6-membered ring aliphatic group. $A^{i1}$ may represent a divalent unsubstituted 6-membered ring aromatic group or a divalent unsubstituted 6-membered ring aliphatic group. A hydrogen atom in these ring structures is preferably not replaced or replaced with an alkyl group having 1 to 6 carbon atoms, an alkoxy group having 1 to 6 carbon atoms, or a halogen atom. $A^{i1}$ preferably represents a divalent unsubstituted 6-membered ring aromatic group, a group in which a hydrogen atom in this ring structure is replaced with a fluorine atom, or a divalent unsubstituted 6-membered ring aliphatic group. $A^{i1}$ preferably represents a 1,4-phenylene group, a 2,6-naphthalene group, or a 1,4-cyclohexyl group, in which a hydrogen atom on the substituent may be replaced with a halogen atom, an alkyl group, or an alkoxy group, provided that at least one substituent is substituted with $P^{i1}$-$Sp^{i1}$-.

Preferably $m^1$ represents an integer of 2 to 5 and more preferably represents an integer of 2 to 4.

In a case where chemical stability is important for the spontaneous orientation aid, $K^{i1}$ is preferably (K-1), (K-3), (K-8), (K-9), (K-10), and (K-11), in a case where liquid crystal alignment is important, $K^{i1}$ is preferably (K-1) to (K-7), (K-10), and (K-11), in a case where solubility to the liquid crystal compound is important, $K^{i1}$ is preferably (K-1), (K-8), and (K-10), and in a case where the balance between these is important, $K^{i1}$ is more preferably (K-1), (K-3), (K-9), and (K-11).

In formula (K-1) to formula (K-11), $W^{K1}$ preferably represents a methine group or C—$CH_3$. $X^{K1}$ and $Y^{K1}$ each independently preferably represent —$CH_2$— or an oxygen atom. $Z^{K1}$ preferably represents an oxygen atom.

In formula (ii), $Sp^{i1}$ preferably represents a linear alkylene group having 1 to 18 carbon atoms or a single bond, more preferably represents a linear alkylene group having 2 to 15 carbon atoms or a single bond, and even more preferably represents a linear alkylene group having 3 to 12 carbon atoms or a single bond.

$R^{i1}$ represents a hydrogen atom, a linear or branched alkyl group having 1 to 20 carbon atoms, a halogenated alkyl group, or $P^{i1}$-$Sp^{i1}$-, wherein —$CH_2$— in the alkyl group is preferably replaced with —O—, —OCO—, or —COO—, provided that —O— moieties are not bonded in series, $R^{i1}$ more preferably represents a hydrogen atom, a linear or branched alkyl group having 1 to 18 carbon atoms, or $P^{i1}$-$Sp^{i1}$- wherein —$CH_2$— in the alkyl group is replaced with —O— or —OCO—, provided that —O— moieties are not bonded in series.

In addition, formula (i) may be, for example, a compound represented by general formula (iii) (hereinafter, also referred to as the "compound (iii)"):

[Chem. 7]

$$R^{i1}-(A^{i2}-Z^{i2})_{m^{iii2}}-G^{i1}-((A^{i1}-Z^{i1})_{m^{iii1}}-K^{i1})_{m^{iii3}} \quad \text{(iii)}$$

In the formula, $Z^{i1}$, $A^{i1}$, $R^{i1}$, and $K^{i1}$ each have the same meaning as $Z^{i1}$, $A^{i1}$, $R^{i1}$, and in general formula (i), $A^{i2}$ has the same meaning as $A^{i1}$ in general formula (i), $Z^{i2}$ has the same meaning as $Z^{i1}$ in general formula (i), in a case where a plurality of $Z^{i1}$'s, $Z^{i2}$'s, $A^{i1}$'s, $m^{iii1}$'s, and/or $A^{i2}$'s are present, these may be the same or different, provided that one of $A^{i1}$ and $A^{i2}$ is substituted with at least one $P^{i1}$-$Sp^{i1}$- and when $K^{i1}$ is (K-11), $Z^{ii1}$ includes at least one of —$CH_2$—$CH_2COO$—, —$OCOCH_2$—$CH_2$—, —$CH_2$—$CH(CH_3)COO$—, —$OCOCH(CH_3)$—$CH_2$—, or —$OCH_2CH_2O$—, $m^{iii1}$ represents an integer of 1 to 5, $m^{iii2}$ represents an integer of 1 to 5, $G^{i1}$ represents a divalent, trivalent, or tetravalent branched structure or a divalent, trivalent, or tetravalent aliphatic or aromatic ring structure, and $m^{iii3}$ represents an integer smaller than the valence of $G^{i1}$ by 1.

$m^{iii1}$ and $m^{iii2}$ each independently represent an integer of 1 to 5, preferably represent an integer of 2 to 5, and more preferably represent an integer of 2 to 4. No matter whether only one $m^{iii1}$ is present or a plurality of $m^{iii1}$'s are present in the molecule, $m^{iii1}$+$m^{iii2}$ is preferably an integer of 1 to 5, preferably an integer of 1 to 4, and preferably an integer of 1 to 3, in the combination of all of $m^{iii1}$ and $m^{iii2}$ in the molecule. $G^{i1}$ represents a divalent, trivalent, or tetravalent branched structure or a divalent, trivalent, or tetravalent aliphatic or aromatic ring structure, the divalent, trivalent, or tetravalent branched structure is preferably any structure of 2-substituted carbon atom, a 3-substituted carbon atom, a 4-substituted carbon atom, a 2-substituted nitrogen atom, a 3-substituted nitrogen atom, and a 4-substituted carbon atom, and the divalent, trivalent, or tetravalent aliphatic or aromatic ring structure is preferably 3- or higher substituted benzene ring or 3- or higher substituted cyclohexane ring.

$m^{iii3}$ means that $A^{i1}$ is bonded to a portion other than atomic bonding, where $G^{i1}$ is bonded to $Z^{i2}$ and accordingly, $m^{iii3}$ represents an integer smaller than the valence of $G^{i1}$ by 1.

More specific examples of general formula (ii) include compounds represented by any of formulae (R-1-1) to (R-1-45). In the formulae, $R^{i1}$ has the same meaning as $R^{i1}$ in formula (ii).

[Chem. 8]

(R-1-1)

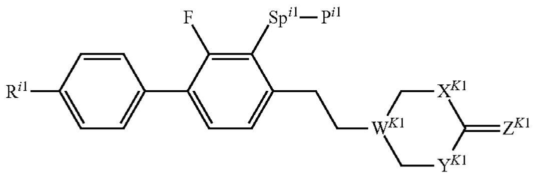

(R-1-2)

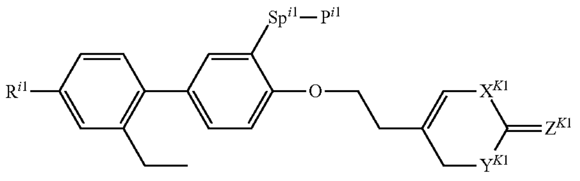

(R-1-3)

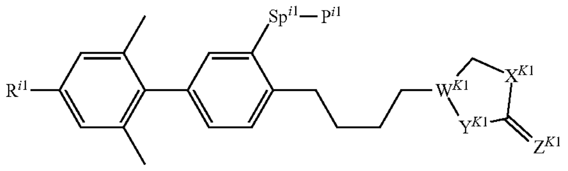

(R-1-4)

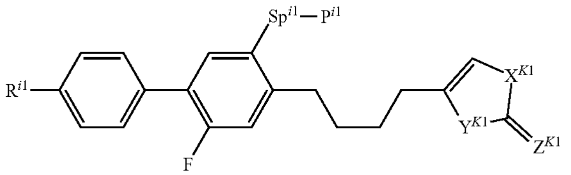

[Chem. 9]

(R-1-5)

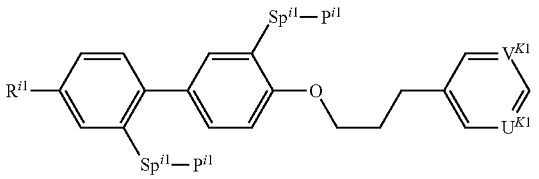

(R-1-6)

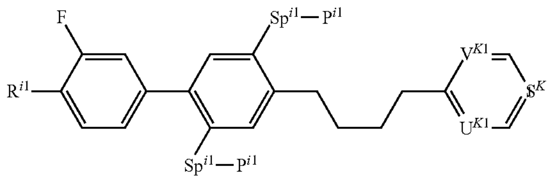

(R-1-7)

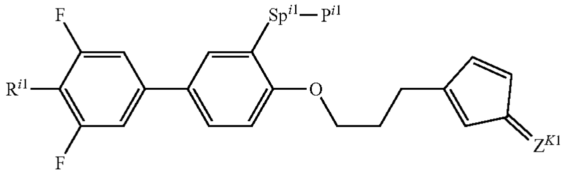

(R-1-8)

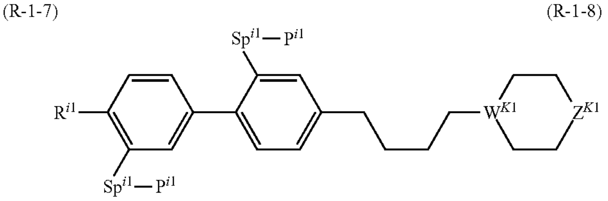

(R-1-9)

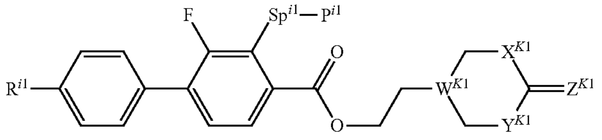

(R-1-10)

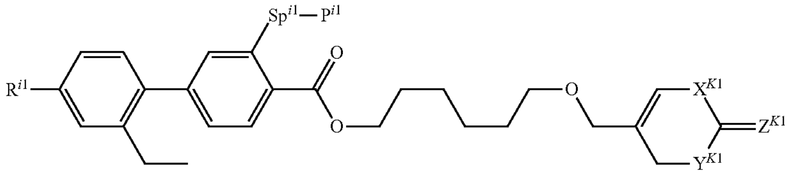

-continued
[Chem. 10]
(R-1-11)
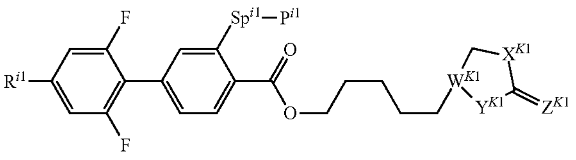
(R-1-12)
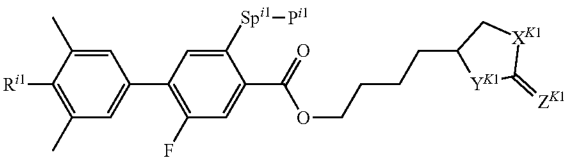
(R-1-13)
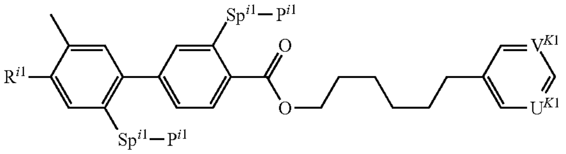
(R-1-14)
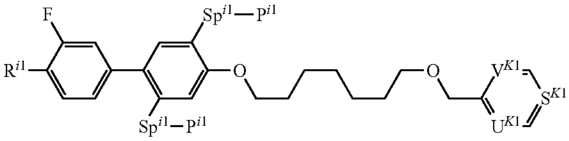
(R-1-15)
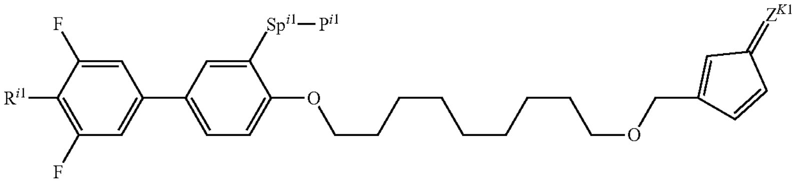
(R-1-16)
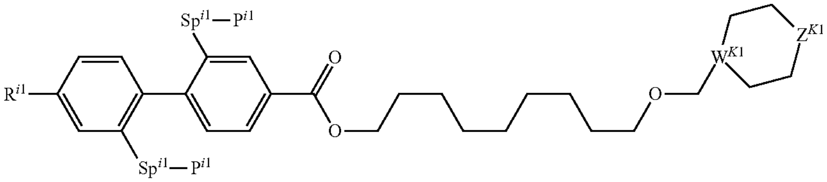
[Chem. 11]
(R-1-17)
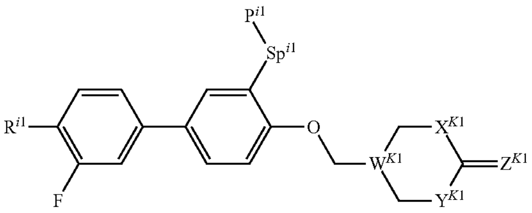
(R-1-18)
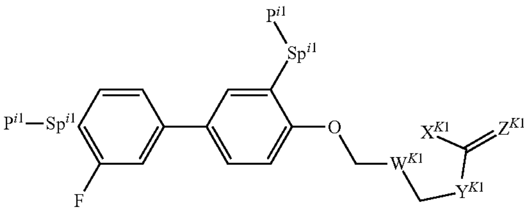
(R-1-19)
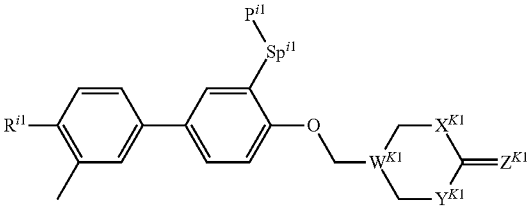
(R-1-20)
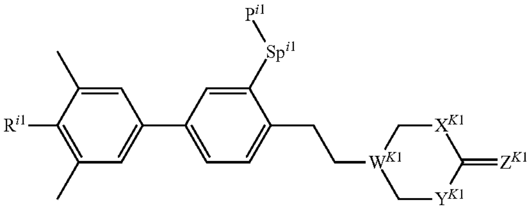
(R-1-21)
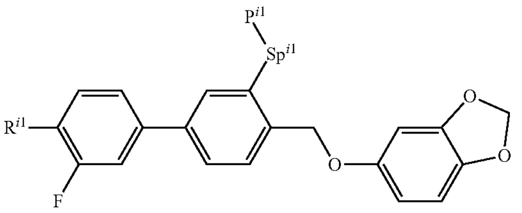
(R-1-22)
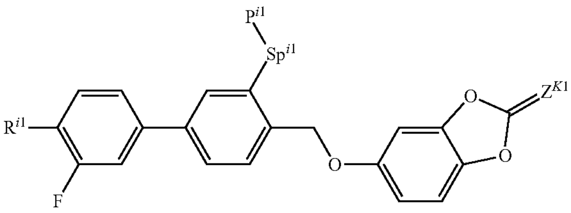

-continued
(R-1-23)
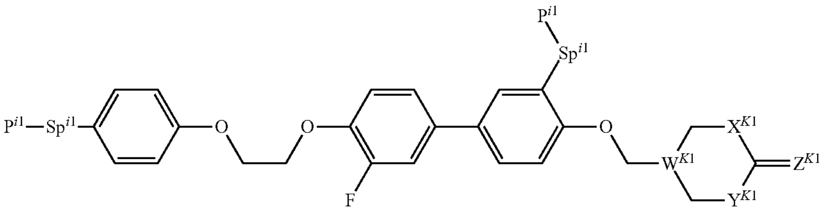
(R-1-24)
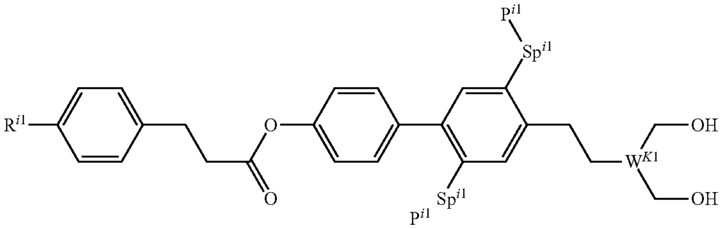
[Chem. 12]
(R-1-25)
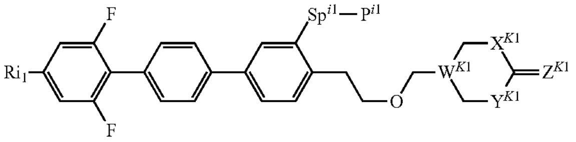
(R-1-26)
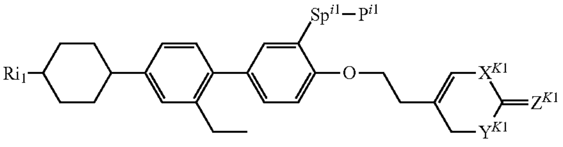
(R-1-27)
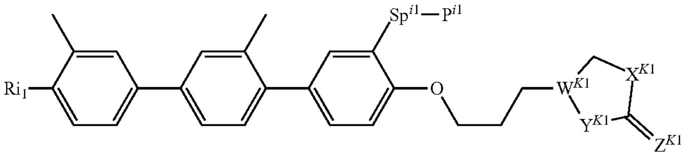
(R-1-28)
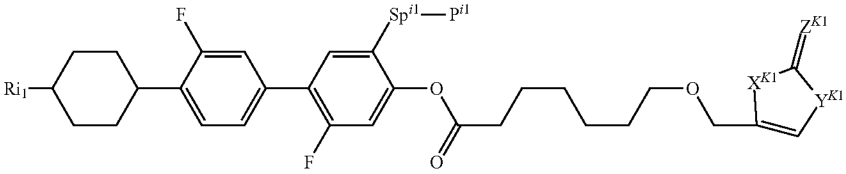
[Chem. 13]
(R-1-29)
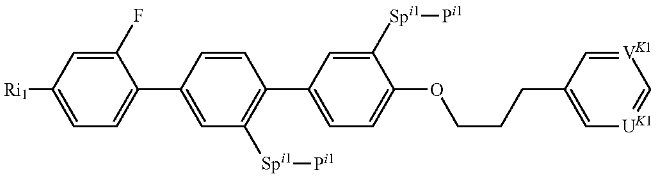
(R-1-30)
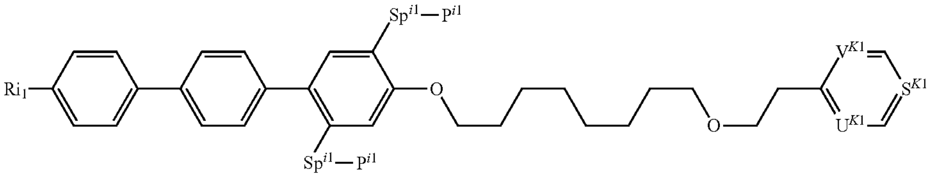

-continued (R-1-31)

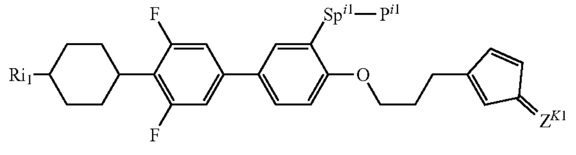

(R-1-32)

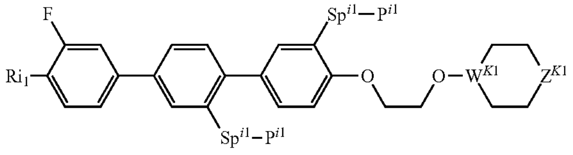

Examples of the compound shown as the compound (iii) include compounds represented by any of general formulae (iii-1) and (iii-2).

[Chem. 14]

(iii-1)

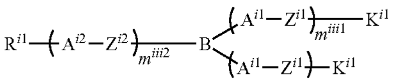

(iii-2)

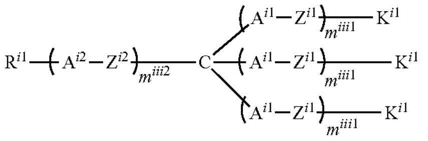

$Z^{i1}$, $A^{i1}$, $R^{i1}$, and $K^{i1}$ each have the same meaning as $Z^{i1}$, $A^{i1}$, $R^{i1}$, and $K^{i1}$ in general formula (i), $A^{i2}$ has the same meaning as $A^{i1}$ in general formula (i), $Z^{i1}$ has the same meaning as $Z^{i1}$ in general formula (i), when a plurality of $Z^{i1}$'s, $Z^{i2}$'s, $A^{i1}$'s, $m^{iii1}$'s, and/or $A^{i2}$'s are present, these may be the same or different, $m^{iii1}$ represents an integer of 1 to 5, $m^{iii2}$ represents an integer of 1 to 5, B represents a trivalent branched structure or a trivalent aliphatic or aromatic ring structure, and C represents a tetravalent branched structure or a tetravalent aliphatic or aromatic ring structure.

More specific examples of general formula (iii) include compounds represented by any of formulae (R-1-33) to (R-1-37). In the formulae, $R^{i1}$ has the same meaning as $R^{i1}$ in formula (ii).

[Chem. 15]

(R-1-33)

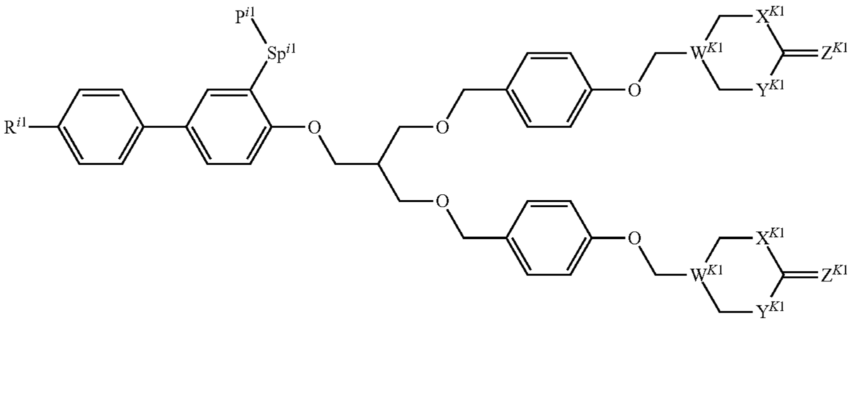

(R-1-34)

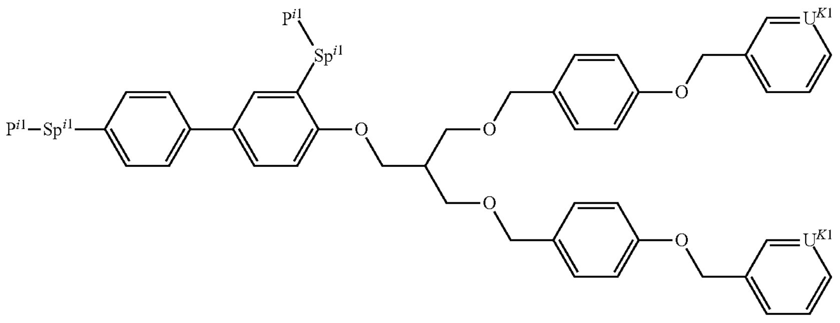

-continued
(R-1-35)
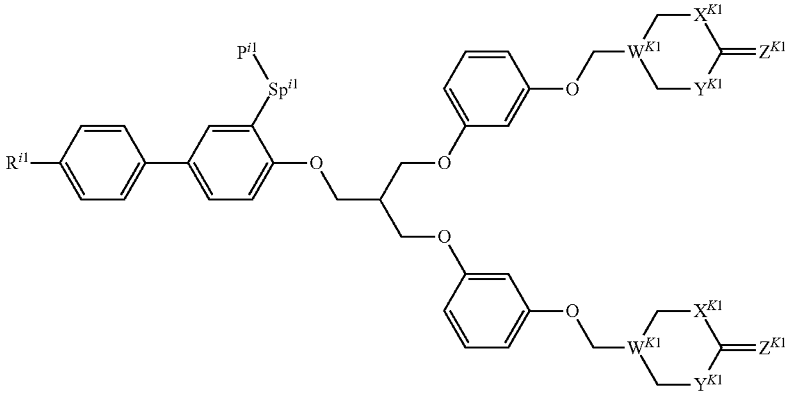
(R-1-36)
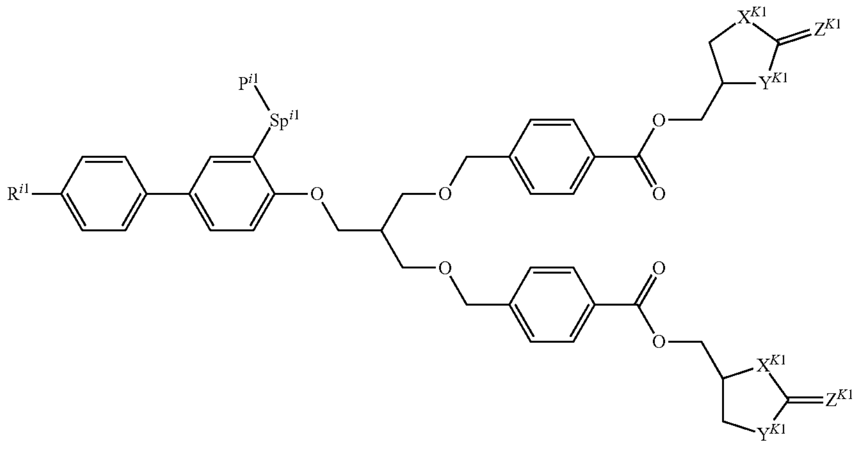
(R-1-37)
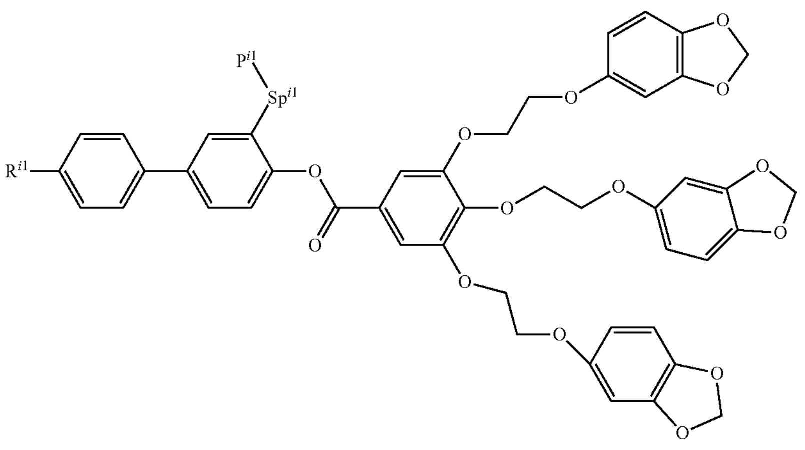

The spontaneous orientation aid for a liquid crystal composition may include one or two or more compounds (i), and may further include a well-known compound used in liquid crystal compositions in addition to one or two or more compounds (i). More specific examples of the spontaneous orientation aid for a liquid crystal composition are represented by (P-1-1) to (P-1-26).

[Chem. 16]

(P-1-1)

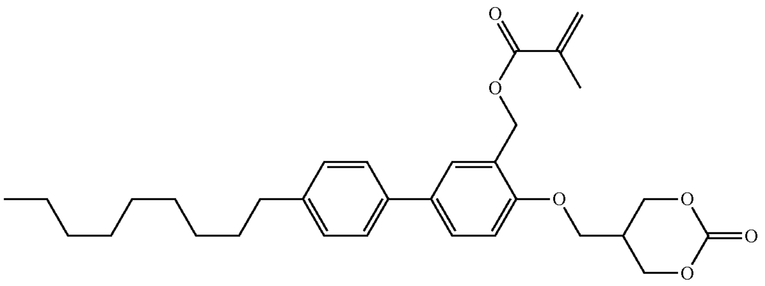

(P-1-2)

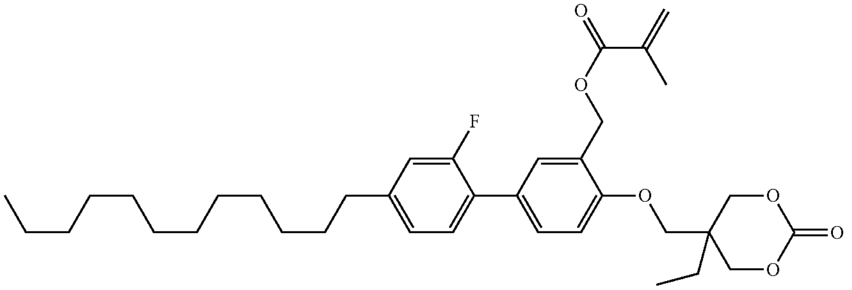

(P-1-3)

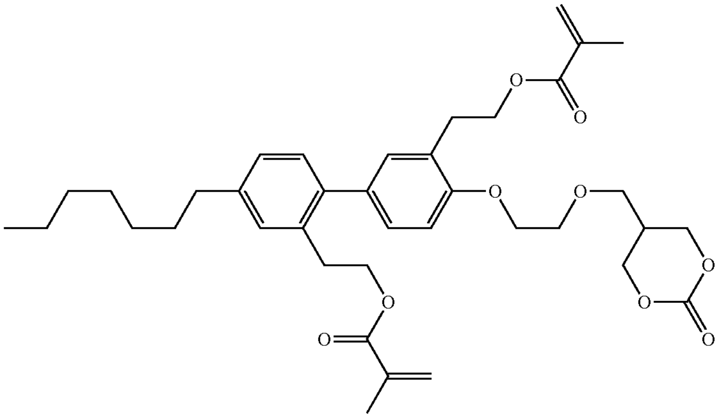

(P-1-4)

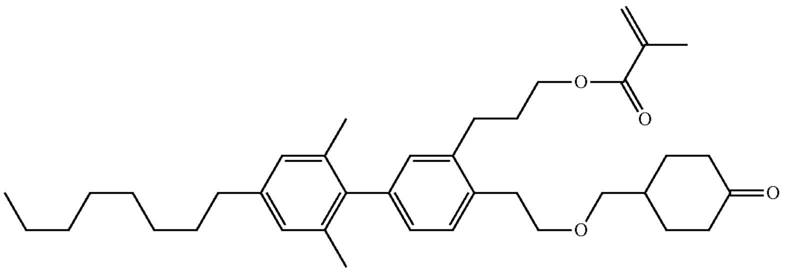

-continued
[Chem. 17]
(P-1-5)
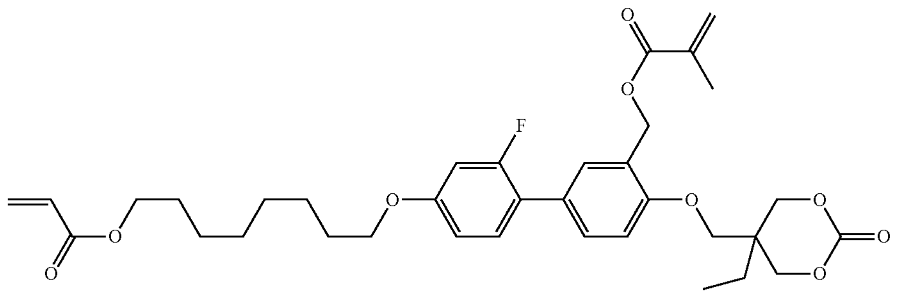
(P-1-6)
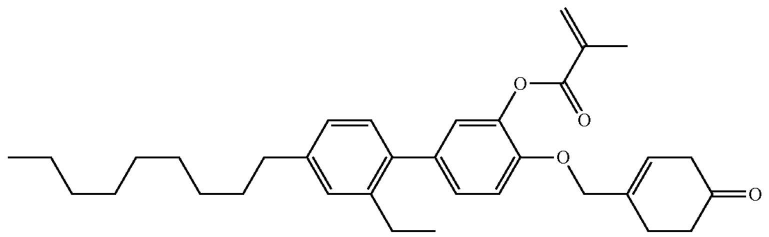
(P-1-7)
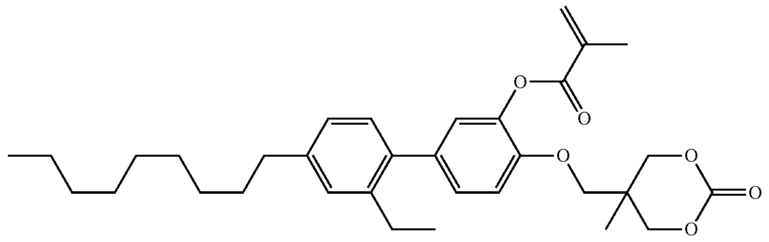
(P-1-8)
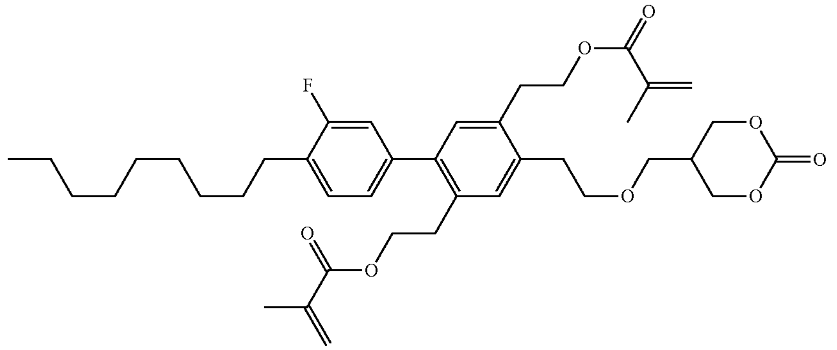

-continued
(P-1-9)
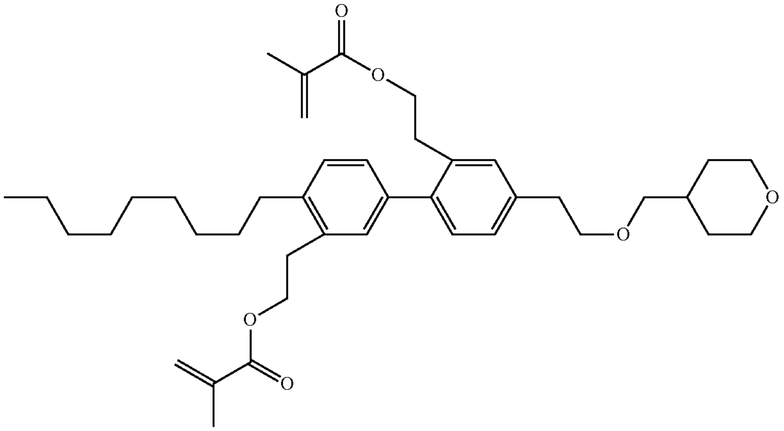
[Chem. 18]
(P-1-10)
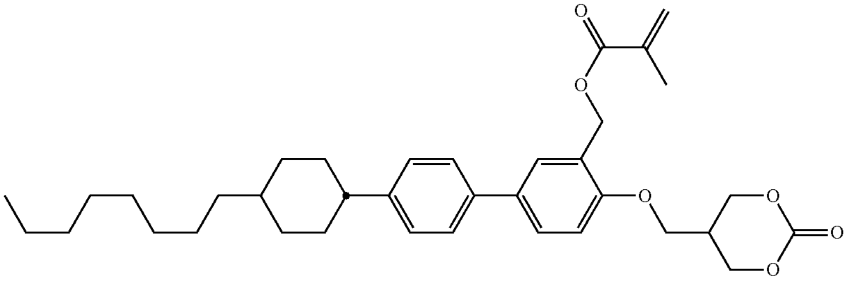
(P-1-11)
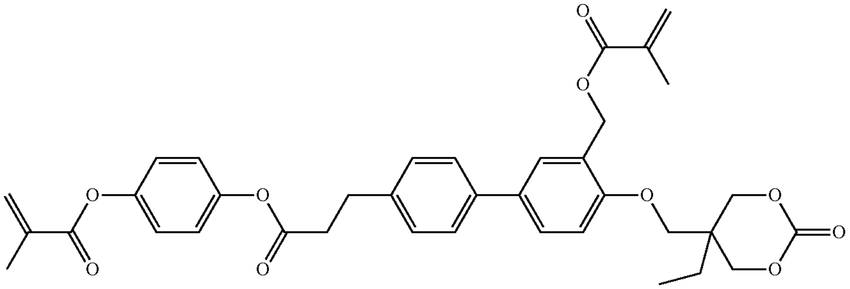
(P-1-12)
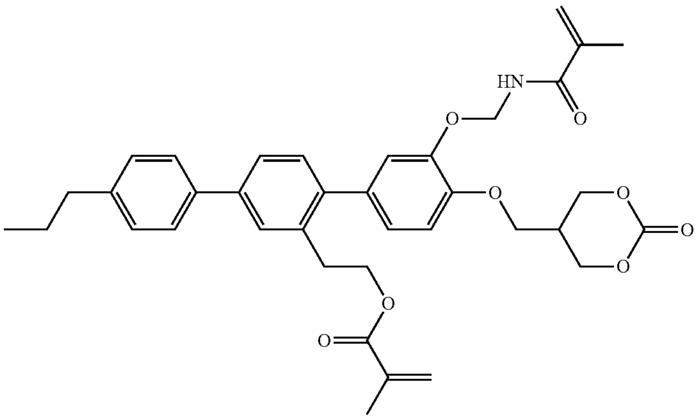

-continued
(P-1-13)
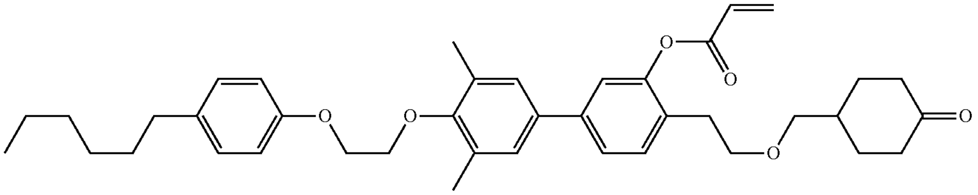
(P-1-14)
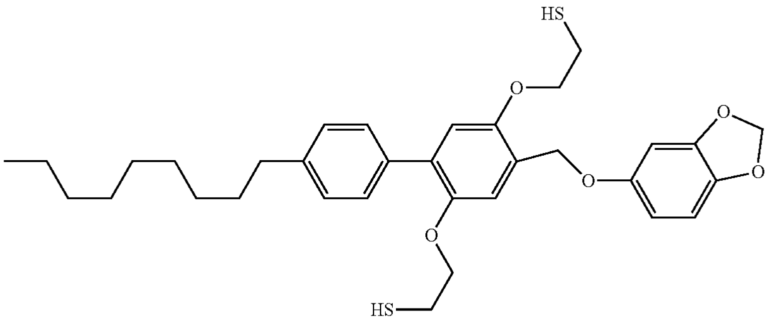
[Chem. 19]
(P-1-15)
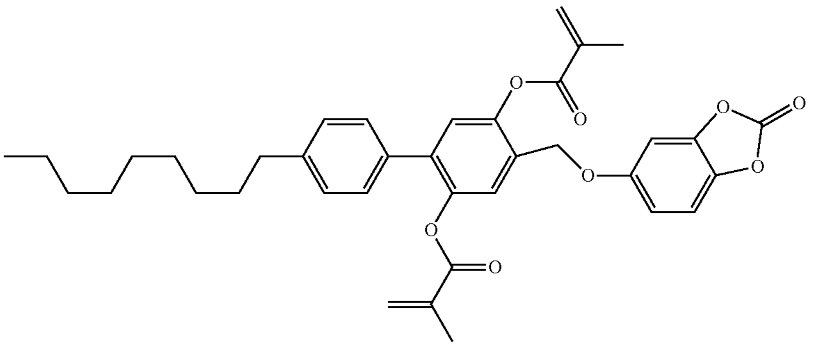
(P-1-16)
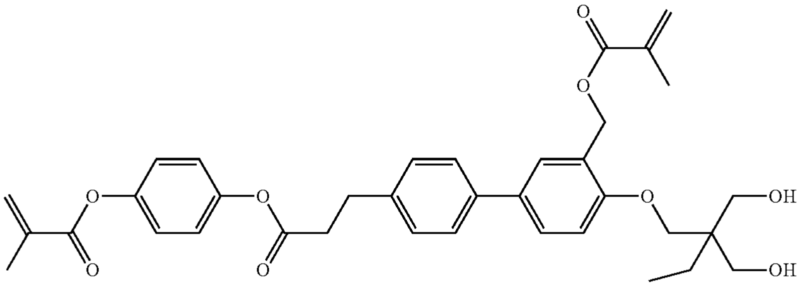
(P-1-17)
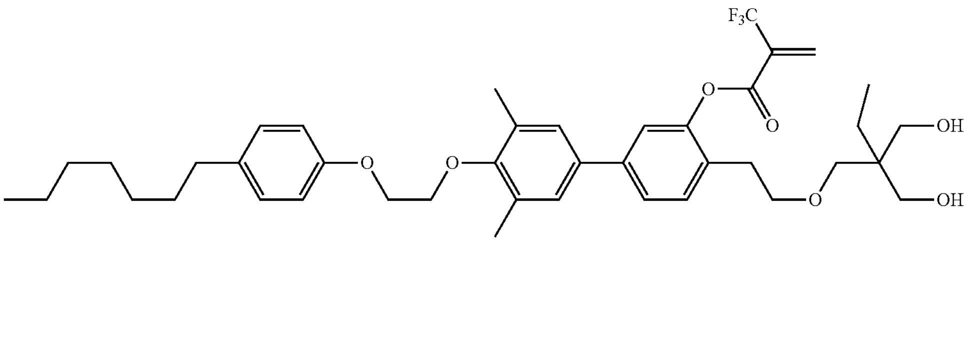

-continued
(P-1-18)
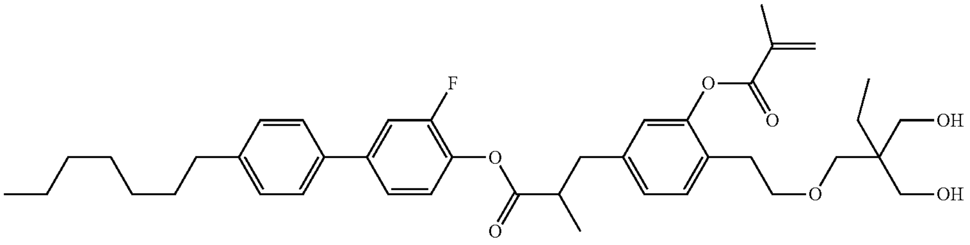
(P-1-19)
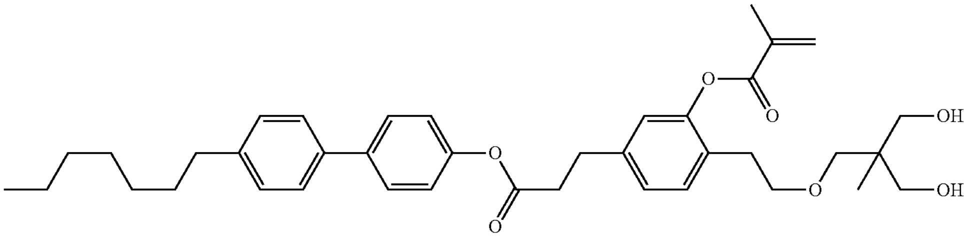
[Chem. 20]
(P-1-20)
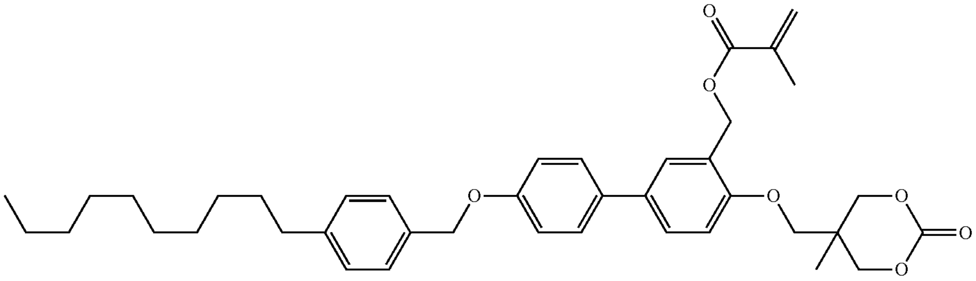
(P-1-21)
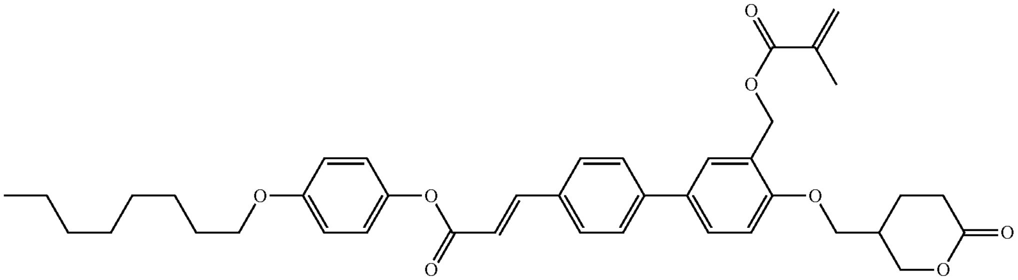
(P-1-22)
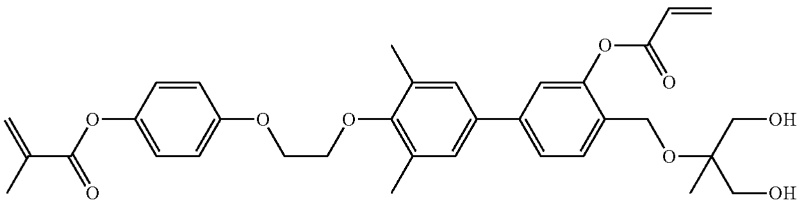
(P-1-23)
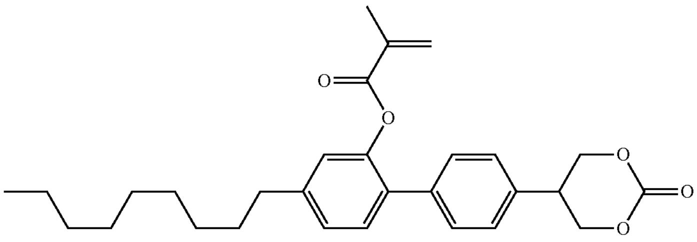

-continued
(P-1-24)
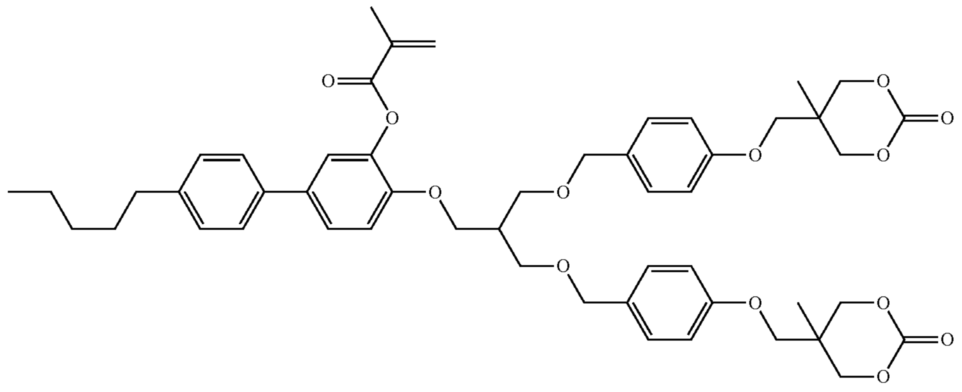
[Chem. 21]
(P-1-25)
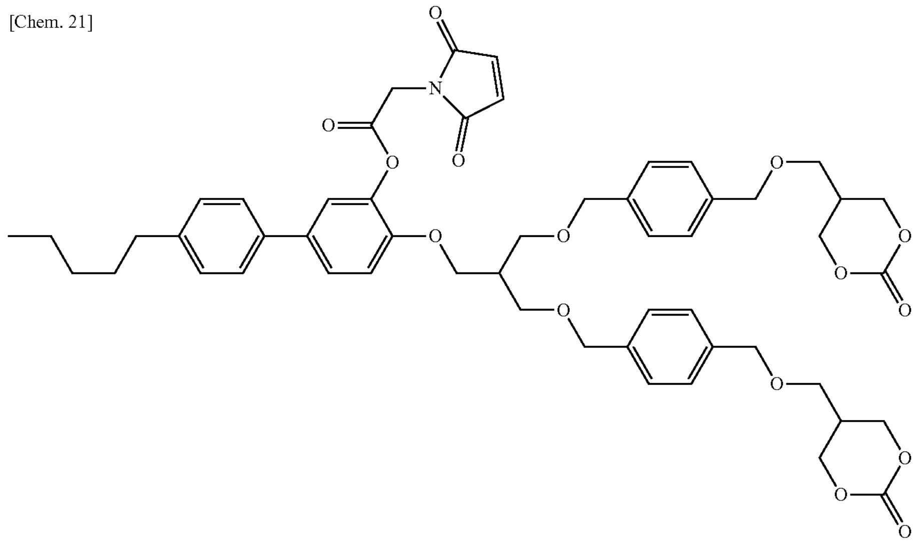
(P-1-26)
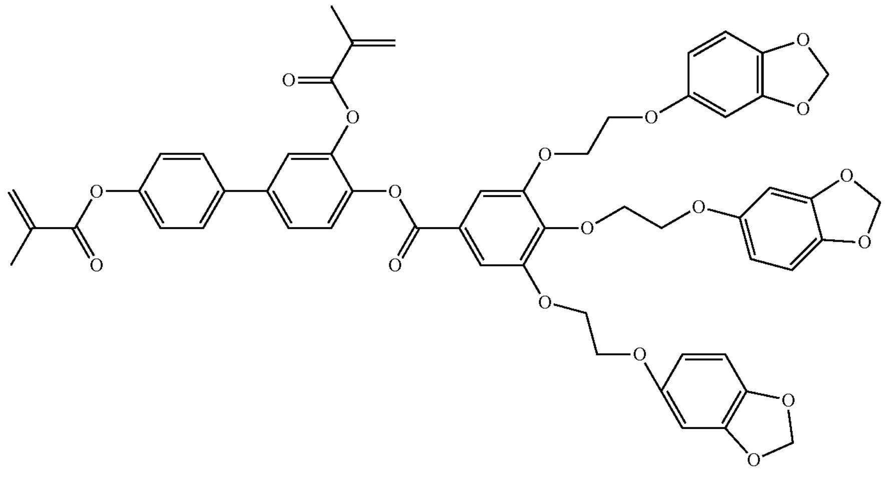

(Liquid Crystal Composition)

The liquid crystal composition of the embodiment includes one kind or two or more kinds of the compound having a partial structure represented by general formula (i). This liquid crystal composition has negative dielectric anisotropy (Δε). The compound having a partial structure represented by general formula (i) included in the liquid crystal composition is the same as the compound (i) of the spontaneous orientation aid for a liquid crystal composition, including the compound (iii), the compound represented by any of formulae (R-1-1) to (R-1-32), the compound (iii), formulae (iii-1) and (iii-2), formulae (R-1-33) to (R-1-37) which are specific examples thereof, and accordingly, the description is omitted here.

A content of the compound (i) is preferably 0.01 to 50% by mass, and the lower limit value thereof is preferably equal to or greater than 0.01% by mass, equal to or greater than 0.1% by mass, equal to or greater than 0.5% by mass, equal to or greater than 0.7% by mass, or equal to or greater than 1% by mass, with respect to a total amount of the liquid crystal composition, from a viewpoint of further suitably aligning liquid crystal molecules. The upper limit value of the content of the compound (i) is preferably equal to or smaller than 50% by mass, equal to or smaller than 30% by mass, equal to or smaller than 10% by mass, equal to or smaller than 7% by mass, equal to or smaller than 5% by mass, equal to or smaller than 4% by mass, equal to or smaller than 3% by mass, with respect to a total amount of the liquid crystal composition, from a viewpoint of excellent response properties.

The liquid crystal composition may further include a compound selected from the group of compounds represented by any of general formulae (N-1), (N-2), and (N-3):

[Chem. 22]

(N-1)

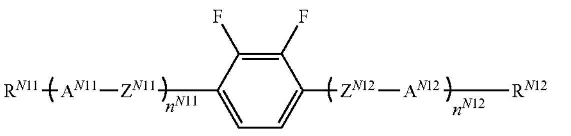

(N-2)

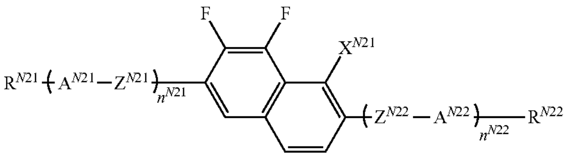

(N-3)

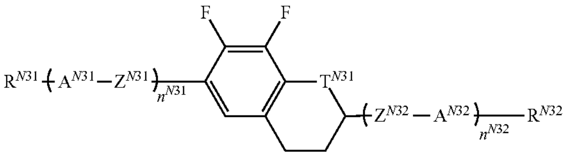

In formulae (N-1), (N-2), and (N-3), $R^{N11}$, $R^{N12}$, $R^{N21}$, $R^{N22}$, $R^{N31}$, and $R^{N32}$ each independently represent an alkyl group having 1 to 8 carbon atoms, one or two or more —$CH_2$—'s not adjacent to each other in the alkyl group each may be independently substituted with —CH═CH—, —O—, —CO—, —COO—, or —OCO—, $A^{N11}$, $A^{N12}$, $A^{N21}$, $A^{N22}$, $A^{N31}$, and $A^{N32}$ each independently represent a group selected from the group consisting of (a) a 1,4-cyclohexylene group (one —$CH_2$— or two or more —$CH_2$—'s not adjacent to each other present in this group may be substituted with —O—), (b) a 1,4-phenylene group (one —CH═ or two or more —CH═'s not adjacent to each other present in this group may be substituted with —N═), (c) a naphthalene-2,6-diyl group, a 1,2,3,4-tetrahydronaphthalene-2,6-diyl group, or a decahydronaphthalene-2,6-diyl group (one —CH═ or two or more —CH═'s not adjacent to each other present in the naphthalene-2,6-diyl group or the 1,2,3,4-tetrahydronaphthalene-2,6-diyl group may be substituted with —N═), and a (d) 1,4-cyclohexenylene group, the group (a), the group (b), the group (c), and the group (d) each may be independently substituted with a cyano group, a fluorine atom, or a chlorine atom, $Z^{N11}$, $Z^{N12}$, $Z^{N21}$, $Z^{N22}$, $Z^{N31}$, and $Z^{N32}$ each independently represent a single bond, —$CH_2CH_2$—, —$(CH_2)_4$—, —$OCH_2$—, —$CH_2O$—, —COO—, —OCO—, —$OCF_2$—, —$CF_2O$—, —CH═N—N═CH—, —CH═CH—, —CF═CF—, or —C≡C—, $X^{N21}$ represents a hydrogen atom or a fluorine atom, $T^{N31}$ represents —$CH_2$— or an oxygen atom, $n^{N11}$, $n^{N12}$, $n^{N21}$, $n^{N22}$, $n^{N31}$, and $n^{N32}$ each independently represent an integer of 0 to 3, $n^{N11}$, $n^{N12}$, $n^{N21}$, $n^{N22}$, and $n^{N31}$ $n^{N32}$ are each independently 1, 2, or 3, and two or more occurrences of one of $A^{N11}$ to $A^{N32}$ and $Z^{N11}$ to $Z^{N32}$ may be the same or different.

The compound represented by any of general formula (N-1), (N-2), and (N-3) is preferably a compound having negative Δε and an absolute value greater than 3.

In general formula (N-1), (N-2), and (N-3), $R^{N11}$, $R^{N12}$, $R^{N21}$, $R^{N22}$, $R^{N31}$, and $R^{N32}$ are each independently preferably an alkyl group having 1 to 8 carbon atoms, an alkoxy group having 1 to 8 carbon atoms, an alkenyl group having 2 to 8 carbon atoms, or an alkenyloxy group having 2 to 8 carbon atoms, more preferably an alkyl group having 1 to 5 carbon atoms, an alkoxy group having 1 to 5 carbon atoms, an alkenyl group having 2 to 5 carbon atoms, or an alkenyloxy group having 2 to 5 carbon atoms, even more preferably an alkyl group having 1 to 5 carbon atoms or an alkenyl group having 2 to 5 carbon atoms, still more preferably an alkyl group having 2 to 5 carbon atoms or an alkenyl group having 2 or 3 carbon atoms, and particularly preferably an alkenyl group (propenyl group) having 3 carbon atoms.

In a case where a ring structure to which $R^{N11}$, $R^{N12}$, $R^{N21}$, $R^{N22}$, $R^{N31}$, and $R^{N32}$ are bonded, is a phenyl group (aromatic group), $R^{N11}$, $R^{N12}$, $R^{N21}$, $R^{N22}$, $R^{N31}$, and $R^{N32}$ are each independently preferably a linear alkyl group having 1 to 5 carbon atoms, a linear alkoxy group having 1 to 4 carbon atoms, and an alkenyl group having 4 or 5 carbon atoms, and in a case where the ring structure, to which these are bonded, is a saturated ring structure of cyclohexane, pyran, and dioxane, $R^{N11}$, $R^{N12}$, $R^{N21}$, $R^{N22}$, $R^{N31}$, and $R^{N32}$ are each independently preferably a linear alkyl group having 1 to 5 carbon atoms, a linear alkoxy group having 1 to 4 carbon atoms, and a linear alkenyl group having 2 to 5 carbon atoms. In order to stabilize a nematic phase, a total number of carbon atoms and oxygen atoms, in a case where oxygen atoms are present, is preferably equal to or smaller than 5 and the structure thereof is preferably linear.

The alkenyl group is preferably selected from groups represented by any of formula (R1) to formula (R5) (each black point in each formula represents atomic bonding).

[Chem. 23]

(R1)

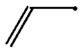

(R2)

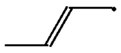

(R3)

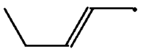

(R4)

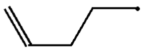

(R5)

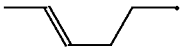

$A^{N11}$, $A^{N12}$, $A^{N21}$, $A^{N22}$, $A^{N31}$, and $A^{N32}$ are each independently an aromatic group, in a case where a value greater than Δn is required to obtain, and preferably an aliphatic group, in order to improve a response speed. $A^{N11}$, $A^{N12}$, $A^{N21}$, $A^{N22}$, $A^{N31}$, and $A^{N32}$ each independently preferably represent a trans-1,4-cyclohexylene group, 1,4-phenylene group, a 2-fluoro-1,4-phenylene group, a 3-fluoro-1,4-phenylene group, a 3,5-difluoro-1,4-phenylene group, a 2,3-difluoro-1,4-phenylene group, a 1,4-cyclohexenylene group, a 1,4-bicyclo [2.2.2]octylene group, a piperidine-1,4-diyl group, a naphthalene-2,6-diyl group, a decahydronaphthalene-2,6-diyl group, or a 1,2,3,4-tetrahydronaphthalene-2,6-diyl group, more preferably represent the following structures:

[Chem. 24]

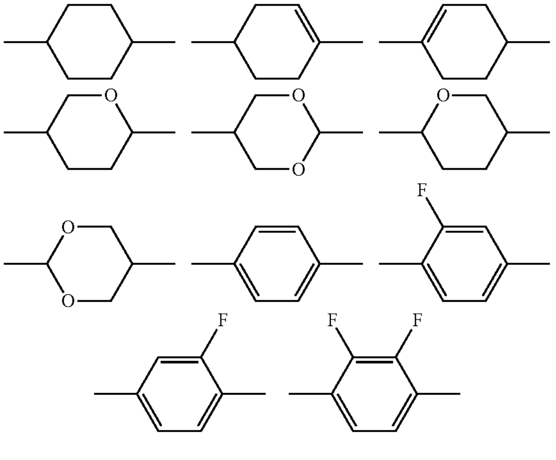

and more preferably represent a trans-1,4-cyclohexylene group, a 1,4-cyclohexenylene group, or a 1,4-phenylene group.

$Z^{N11}$, $Z^{N12}$, $Z^{N21}$, $Z^{N22}$, $Z^{N31}$, and $Z^{N32}$ each independently preferably represent $—CH_2O—$, $—CF_2O—$, $—CH_2CH_2—$, $—CF_2CF_2—$, or a single bond, more preferably represent $—CH_2O—$, $—CH_2CH_2—$, or a single bond, and particularly preferably represent $—CH_2O—$ or a single bond.

$X^{N21}$ is preferably a fluorine atom.

$T^{N31}$ is preferably an oxygen atom.

$n^{N11}+n^{N12}$, $n^{N21}+n^{N22}$, and $n^{N31}+n^{N32}$ are preferably 1 or 2, and a combination in which $n^{N11}$ is 1 and $n^{N12}$ is 0, a combination in which $n^{N11}$ is 2 and $n^{N12}$ is 0, a combination in which $n^{N11}$ is 1 and $n^{N12}$ is 1, a combination in which $n^{N11}$ is 2 and $n^{N12}$ is 1, a combination in which $n^{N21}$ is 1 and $n^{N22}$ is 0, a combination in which $n^{N21}$ is 2 and $n^{N22}$ is 0, a combination in which $n^{N31}$ is 1 and $n^{N32}$ is 0, and a combination in which $n^{N31}$ is 2 and $n^{N32}$ is 0 are preferable.

The preferable lower limit value of the content of the compound represented by formula (N-1) with respect to a total amount of the composition of the embodiment is equal to or greater than 1% by mass, equal to or greater than 10% by mass, equal to or greater than 20% by mass, equal to or greater than 30% by mass, equal to or greater than 40% by mass, equal to or greater than 50% by mass, equal to or greater than 55% by mass, equal to or greater than 60% by mass, equal to or greater than 65% by mass, equal to or greater than 70% by mass, equal to or greater than 75% by mass, and equal to or greater than 80% by mass. The preferable upper limit value of the content thereof is equal to or smaller than 95% by mass, equal to or smaller than 85% by mass, equal to or smaller than 75% by mass, equal to or smaller than 65% by mass, equal to or smaller than 55% by mass, equal to or smaller than 45% by mass, equal to or smaller than 35% by mass, equal to or smaller than 25% by mass, and equal to or smaller than 20% by mass.

The preferable lower limit value of the content of the compound represented by formula (N-2) with respect to a total amount of the composition of the embodiment is equal to or greater than 1% by mass, equal to or greater than 10% by mass, equal to or greater than 20% by mass, equal to or greater than 30% by mass, equal to or greater than 40% by mass, equal to or greater than 50% by mass, equal to or greater than 55% by mass, equal to or greater than 60% by mass, equal to or greater than 65% by mass, equal to or greater than 70% by mass, equal to or greater than 75% by mass, and equal to or greater than 80% by mass. The preferable upper limit value of the content thereof is equal to or smaller than 95% by mass, equal to or smaller than 85% by mass, equal to or smaller than 75% by mass, equal to or smaller than 65% by mass, equal to or smaller than 55% by mass, equal to or smaller than 45% by mass, equal to or smaller than 35% by mass, equal to or smaller than 25% by mass, and equal to or smaller than 20% by mass.

The preferable lower limit value of the content of the compound represented by formula (N-3) with respect to a total amount of the composition of the embodiment is equal to or greater than 1% by mass, equal to or greater than 10% by mass, equal to or greater than 20% by mass, equal to or greater than 30% by mass, equal to or greater than 40% by mass, equal to or greater than 50% by mass, equal to or greater than 55% by mass, equal to or greater than 60% by mass, equal to or greater than 65% by mass, equal to or greater than 70% by mass, equal to or greater than 75% by mass, and equal to or greater than 80% by mass. The preferable upper limit value of the content thereof is equal to or smaller than 95% by mass, equal to or smaller than 85% by mass, equal to or smaller than 75% by mass, equal to or smaller than 65% by mass, equal to or smaller than 55% by mass, equal to or smaller than 45% by mass, equal to or smaller than 35% by mass, equal to or smaller than 25% by mass, and equal to or smaller than 20% by mass.

In a case where a viscosity of the composition of the embodiment is maintained to be low and a composition having a high response speed is necessary, it is preferable that the lower limit value is low and the upper limit value is low. In addition, in a case where Tni of the composition of the embodiment is maintained to be high and a composition having excellent temperature stability is necessary, it is preferable that the lower limit value is low and the upper limit value is low. In a case where it is desired to increase dielectric anisotropy for maintaining a driving voltage to be low, it is preferable that the lower limit value is high and the upper limit value is high.

As the compound represented by general formula (N-1), a compound group represented by general formulae (N-1a) to (N-1g) can be used.

[Chem. 25]

(N-1a)

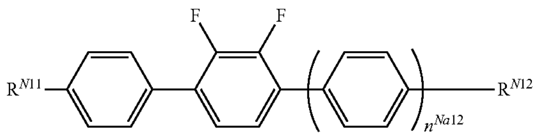

(N-1b)

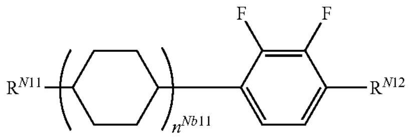

(N-1c)

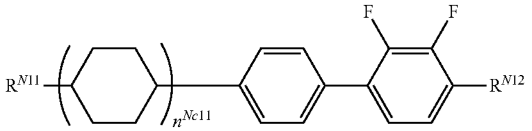

(N-1d)

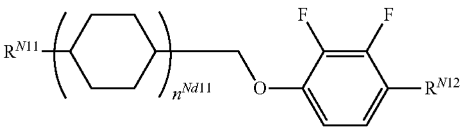

(N-1e)

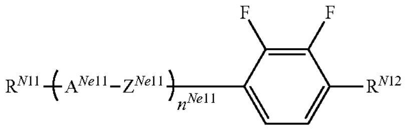

(N-1f)

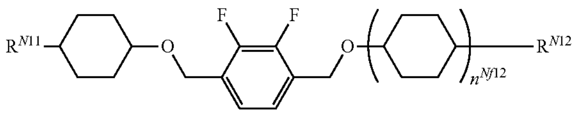

(N-1g)

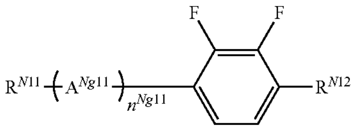

In the formulae, $R^{N11}$ and $R^{N12}$ represent the same meaning as $R^{N11}$ and $R^{N12}$ in general formula (N-1), $n^{Na11}$ represents 0 or 1, $n^{Nb11}$ represents 0 or 1, $n^{Nc11}$ represents 0 or 1, $n^{Nd11}$ represents 0 or 1, $n^{Ne11}$ represents 1 or 2, $n^{Nf11}$ represents 1 or 2, $n^{Ng11}$ represents 1 or 2, $A^{Ne11}$ represents a trans-1,4-cyclohexylene group or a 1,4-phenylene group, $A^{Ng11}$ represents a trans-, 4-cyclohexylene group, 1,4-cyclohexenylene group, or 1,4-phenylene group, at least one thereof represents a 1,4-cyclohexenylene group, and $Z^{Ne11}$ represents a single bond or ethylene, and at least one thereof represents ethylene.

More specifically, the compound represented by general formula (N-1) is preferably a compound selected from the compound group represented by general formulae (N-1-1) to (N-1-21).

The compound represented by general formula (N-1-1) is the following compound.

[Chem. 26]

(N-1-1)

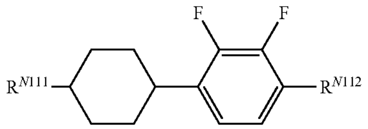

In the formula, $R^{N111}$ and $R^{N112}$ each independently represent the same meaning as $R^{N11}$ and $R^{N12}$ in general formula (N).

$R^{N111}$ is preferably an alkyl group having 1 to 5 carbon atoms or an alkenyl group having 2 to 5 carbon atoms, and preferably a propyl group, a pentyl group, or a vinyl group. $R^{N112}$ is preferably an alkyl group having 1 to 5 carbon atoms, an alkenyl group having 4 or 5 carbon atoms, or an alkoxy group having 1 to 4 carbon atoms, and preferably an ethoxy group or a butoxy group.

The compound represented by general formula (N-1-1) can be used alone, and two or more compounds can also be used in combination. The kind of the compound which can be used in combination is not particularly limited, and compounds are suitably used in combination, in accordance with required performance such as solubility at a low temperature, a transition temperature, electrical reliability, or a birefringence. The number of kind of the compound used is one, two, three, four, or five or more, in one embodiment, for example.

In a case where the improvement of $\Delta\varepsilon$ is important, the content is preferably set to be high, in a case where the solubility at a low temperature is important, the effect is high by setting the content to be great, and in a case where $T_{NI}$ is important, the effect is high by setting the content to be low. In a case of improving dropping marks or burning properties, the range of the content is preferably set to be moderate.

The preferable lower limit value of the content of the compound represented by formula (N-1-1) with respect to a total amount of the composition of the embodiment is equal to or greater than 5% by mass, equal to or greater than 10% by mass, equal to or greater than 13% by mass, equal to or greater than 15% by mass, equal to or greater than 17% by mass, equal to or greater than 20% by mass, equal to or greater than 23% by mass, equal to or greater than 25% by mass, equal to or greater than 27% by mass, equal to or greater than 30% by mass, equal to or greater than 33% by mass, or equal to or greater than 35% by mass. The preferable upper limit value of the content thereof with respect to a total amount of the composition of the embodiment is equal to or smaller than 50% by mass, equal to or smaller than 40% by mass, equal to or smaller than 38% by mass, equal to or smaller than 35% by mass, equal to or smaller than 33% by mass, equal to or smaller than 30% by mass, equal to or smaller than 28% by mass, equal to or smaller than 25% by mass, equal to or smaller than 23% by mass, equal to or smaller than 20% by mass, equal to or smaller than 18% by mass, equal to or smaller than 15% by mass, equal to or smaller than 13% by mass, equal to or smaller than 10% by mass, equal to or smaller than 8% by mass, equal to or smaller than 7% by mass, equal to or smaller than 6% by mass, equal to or smaller than 5% by mass, or equal to or smaller than 3% by mass.

The compound represented by general formula (N-1-1) is preferably a compound selected from the compound group represented by formula (N-1-1.1) to formula (N-1-1.23), preferably a compound represented by formula (N-1-1.1) to formula (N-1-1.4), and preferably a compound represented by formula (N-1-1.1) and formula (N-1-1.3).

[Chem. 27]

(N-1-1.1)

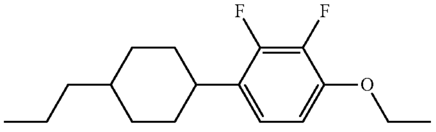

(N-1-1.2)

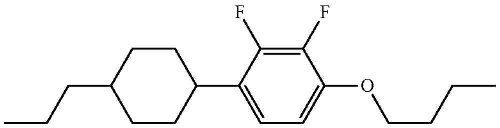

(N-1-1.3)

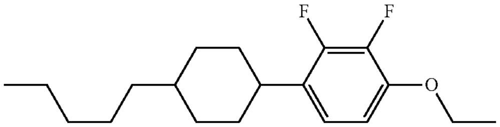

(N-1-1.4)

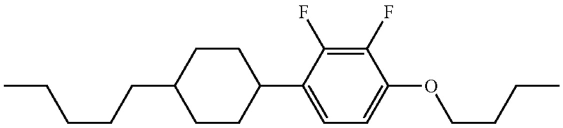

(N-1-1.11)

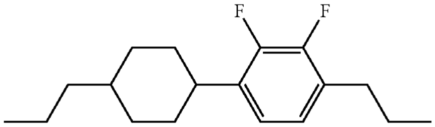

(N-1-1.12)

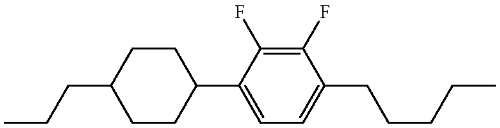

(N-1-1.13)

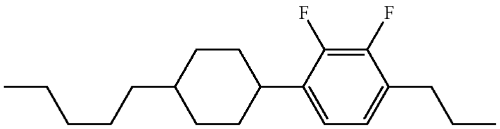

(N-1-1.14)

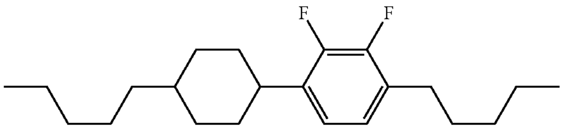

-continued (N-1-120)

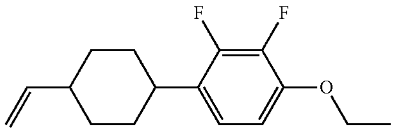

(N-1-1.21)

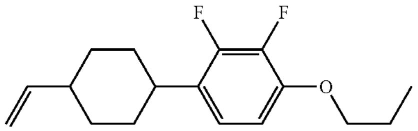

(N-1-1.22)

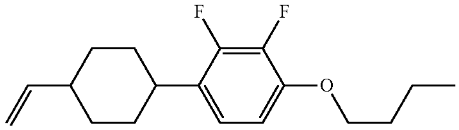

The compounds represented by formulae (N-1-1.1) to (N-1-1.22) can be used alone or in combination, and the preferable lower limit value of the content of the single compound or these compounds with respect to a total amount of the composition of the embodiment is equal to or greater than 5% by mass, equal to or greater than 10% by mass, equal to or greater than 13% by mass, equal to or greater than 15% by mass, equal to or greater than 17% by mass, equal to or greater than 20% by mass, equal to or greater than 23% by mass, equal to or greater than 25% by mass, equal to or greater than 27% by mass, equal to or greater than 30% by mass, equal to or greater than 33% by mass, or equal to or greater than 35% by mass. The preferable upper limit value of the content thereof with respect to a total amount of the composition of the embodiment is equal to or smaller than 50% by mass, equal to or smaller than 40% by mass, equal to or smaller than 38% by mass, equal to or smaller than 35% by mass, equal to or smaller than 33% by mass, equal to or smaller than 30% by mass, equal to or smaller than 28% by mass, equal to or smaller than 25% by mass, equal to or smaller than 23% by mass, equal to or smaller than 20% by mass, equal to or smaller than 18% by mass, equal to or smaller than 15% by mass, equal to or smaller than 13% by mass, equal to or smaller than 10% by mass, equal to or smaller than 8% by mass, equal to or smaller than 7% by mass, equal to or smaller than 6% by mass, equal to or smaller than 5% by mass, or equal to or smaller than 3% by mass.

The compound represented by general formula (N-1-2) is the following compound.

[Chem. 28]

(N-1-2)

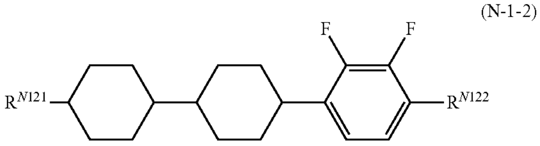

In the formula, $R^{N121}$ and $R^{N122}$ each independently represent the same meaning as $R^{N11}$ and $R^{N12}$ in general formula (N).

$R^{N121}$ is preferably an alkyl group having 1 to 5 carbon atoms or an alkenyl group having 2 to 5 carbon atoms, and preferably an ethyl group, a propyl group, a butyl group, or a pentyl group. $R^{N122}$ is preferably an alkyl group having 1 to 5 carbon atoms, an alkenyl group having 4 or 5 carbon atoms, or an alkoxy group having 1 to 4 carbon atoms, and preferably a methyl group, a propyl group, a methoxy group, an ethoxy group, or a propoxy group.

The compound represented by general formula (N-1-2) can be used alone or a combination of two or more compounds can also be used. The kind of the compound which can be used in combination is not particularly limited, and compounds are suitably used in combination, in accordance with required performance such as solubility at a low temperature, a transition temperature, electrical reliability, or a birefringence. The number of kind of the compound used is one, two, three, four, or five or more, in one embodiment, for example.

In a case where the improvement of Δε is important, the content is preferably set to be high, in a case where the solubility at a low temperature is important, the effect is high by setting the content to be low, and in a case where $T_{NI}$ is important, the effect is high by setting the content to be great. In a case of improving dropping marks or burning properties, the range of the content is preferably set to be moderate.

The preferable lower limit value of the content of the compound represented by formula (N-1-2) with respect to a total amount of the composition of the embodiment is equal to or greater than 5% by mass, equal to or greater than 7% by mass, equal to or greater than 10% by mass, equal to or greater than 13% by mass, equal to or greater than 15% by mass, equal to or greater than 17% by mass, equal to or greater than 20% by mass, equal to or greater than 23% by mass, equal to or greater than 25% by mass, equal to or greater than 27% by mass, equal to or greater than 30% by mass, equal to or greater than 33% by mass, equal to or greater than 35% by mass, equal to or greater than 37% by mass, equal to or greater than 40% by mass, or equal to or greater than 42% by mass. The preferable upper limit value of the content thereof with respect to a total amount of the composition of the embodiment is equal to or smaller than 50% by mass, equal to or smaller than 48% by mass, equal to or smaller than 45% by mass, equal to or smaller than 43% by mass, equal to or smaller than 40% by mass, equal to or smaller than 38% by mass, equal to or smaller than 35% by mass, equal to or smaller than 33% by mass, equal to or smaller than 30% by mass, equal to or smaller than 28% by mass, equal to or smaller than 25% by mass, equal to or smaller than 23% by mass, equal to or smaller than 20% by mass, equal to or smaller than 18% by mass, equal to or smaller than 15% by mass, equal to or smaller than 13% by mass, equal to or smaller than 10% by mass, equal to or smaller than 8% by mass, equal to or smaller than 7% by mass, equal to or smaller than 6% by mass, or equal to or smaller than 5% by mass.

The compound represented by general formula (N-1-2) is preferably a compound selected from the compound group represented by formula (N-1-2.1) to formula (N-1-2.22), preferably a compound represented by formula (N-1-2.3) to formula (N-1-2.7), formula (N-1-2.10), formula (N-1-2.11), formula (N-1-2.13), and formula (N-1-2.20), preferably a compound represented by formula (N-1-2.3) to formula (N-1-2.7), in a case where the improvement of Δε is important, preferably a compound represented by formula (N-1-2.10), formula (N-1-2.11), and formula (N-1-2.13), in a case where the improvement of $T_{NI}$ is important, and preferably a compound represented by formula (N-1-2.20), in a case where the improvement of the response speed is important.

[Chem. 29]

(N-1-2.1)

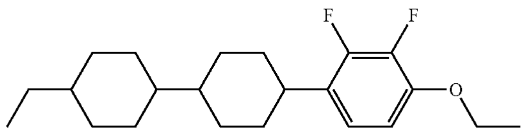

(N-1-2.2)

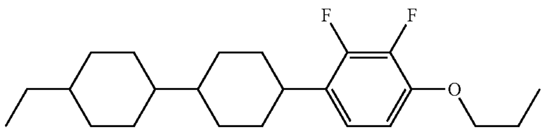

(N-1-2.3)

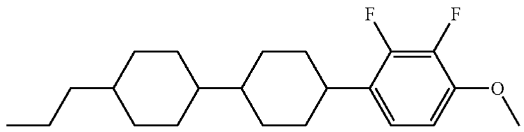

(N-1-2.4)

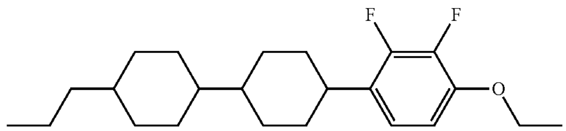

(N-1-2.5)

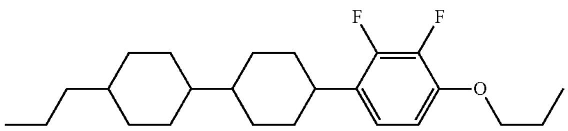

(N-1-2.6)

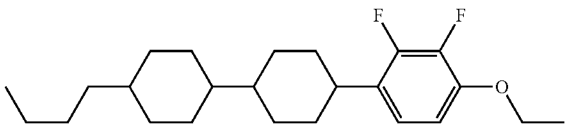

(N-1-2.7)

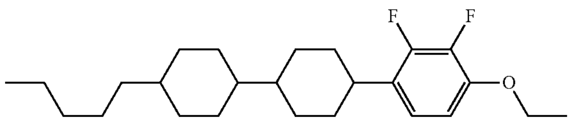

(N-1-2.10)

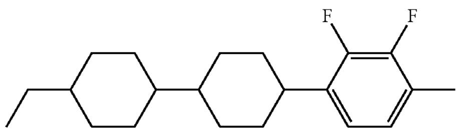

(N-1-2.11)

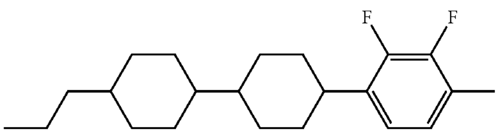

(N-1-2.12)

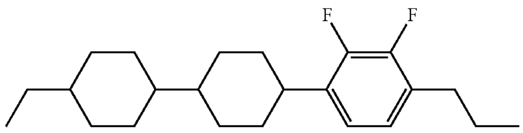

-continued (N-1-2.13)

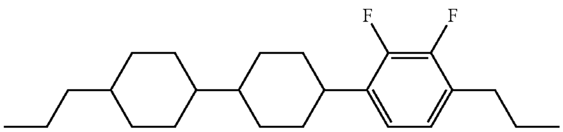

(N-1-2.20)

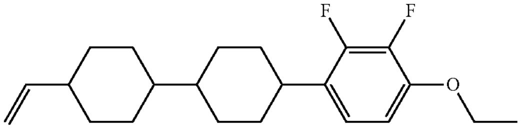

(N-1-2.21)

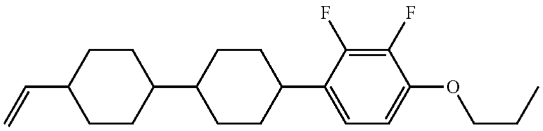

(N-1-2.22)

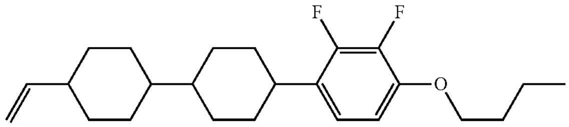

The compounds represented by formula (N-1-2.1) to formula (N-1-2.22) can be used alone or in combination, and the preferable lower limit value of the content of the single compound or these compounds with respect to a total amount of the composition of the embodiment is equal to or greater than 5% by mass, equal to or greater than 10% by mass, equal to or greater than 13% by mass, equal to or greater than 15% by mass, equal to or greater than 17% by mass, equal to or greater than 20% by mass, equal to or greater than 23% by mass, equal to or greater than 25% by mass, equal to or greater than 27% by mass, equal to or greater than 30% by mass, equal to or greater than 33% by mass, or equal to or greater than 35% by mass. The preferable upper limit value of the content thereof with respect to a total amount of the composition of the embodiment is equal to or smaller than 50% by mass, equal to or smaller than 40% by mass, equal to or smaller than 38% by mass, equal to or smaller than 35% by mass, equal to or smaller than 33% by mass, equal to or smaller than 30% by mass, equal to or smaller than 28% by mass, equal to or smaller than 25% by mass, equal to or smaller than 23% by mass, equal to or smaller than 20% by mass, equal to or smaller than 18% by mass, equal to or smaller than 15% by mass, equal to or smaller than 13% by mass, equal to or smaller than 10% by mass, equal to or smaller than 8% by mass, equal to or smaller than 7% by mass, equal to or smaller than 6% by mass, equal to or smaller than 5% by mass, or equal to or smaller than 3% by mass.

The compound represented by general formula (N-1-3) is the following compound.

[Chem. 30]

(N-1-3)

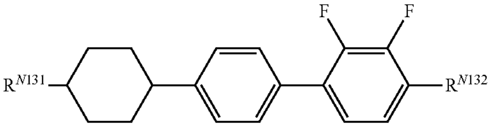

In the formula, $R^{N31}$ and $R^{N132}$ each independently represent the same meaning as $R^{N11}$ and $R^{N12}$ in general formula (N).

$R^{N131}$ is preferably an alkyl group having 1 to 5 carbon atoms or an alkenyl group having 2 to 5 carbon atoms, and preferably an ethyl group, a propyl group, or a butyl group. $R^{N132}$ is preferably an alkyl group having 1 to 5 carbon atoms, an alkenyl group having 3 to 5 carbon atoms, or an alkoxy group having 1 to 4 carbon atoms, and preferably a 1-propenyl group, an ethoxy group, a propoxy group, or a butoxy group.

The compound represented by general formula (N-1-3) can be used alone or a combination of two or more compounds can also be used. The kind of the compound which can be used in combination is not particularly limited, and compounds are suitably used in combination, in accordance with required performance such as solubility at a low temperature, a transition temperature, electrical reliability, or a birefringence. The number of kind of the compound used is one, two, three, four, or five or more, in one embodiment, for example.

In a case where the improvement of Δε is important, the content is preferably set to be high, in a case where the solubility at a low temperature is important, the effect is high by setting the content to be great, and in a case where $T_{NI}$ is important, the effect is high by setting the content to be great. In a case of improving dropping marks or burning properties, the range of the content is preferably set to be moderate.

The preferable lower limit value of the content of the compound represented by formula (N-1-3) with respect to a total amount of the composition of the embodiment is equal to or greater than 5% by mass, equal to or greater than 10% by mass, equal to or greater than 13% by mass, equal to or greater than 15% by mass, equal to or greater than 17% by mass, or equal to or greater than 20% by mass. The preferable upper limit value of the content thereof with respect to a total amount of the composition of the embodiment is equal to or smaller than 35% by mass, equal to or smaller than 30% by mass, equal to or smaller than 28% by mass, equal to or smaller than 25% by mass, equal to or smaller than 23% by mass, equal to or smaller than 20% by mass, equal to or smaller than 18% by mass, equal to or smaller than 15% by mass, or equal to or smaller than 13% by mass.

The compound represented by general formula (N-1-3) is preferably a compound selected from the compound group represented by formula (N-1-3.1) to formula (N-1-3.21), preferably a compound represented by formulae (N-1-3.1) to (N-1-3.7) and formula (N-1-3.21), and preferably a compound represented by formula (N-1-3.1), formula (N-1-3.2), formula (N-1-3.3), formula (N-1-3.4), and formula (N-1-3.6).

[Chem. 31]

(N-1-3.1)

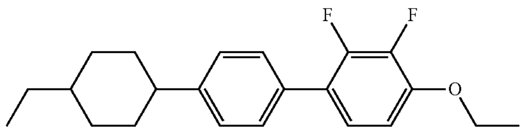

(N-1-3.2)

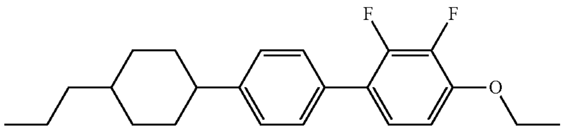

(N-1-3.3)

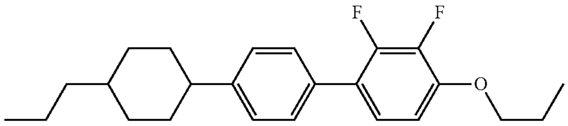

(N-1-3.4)

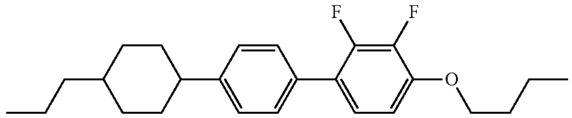

(N-1-3.5)

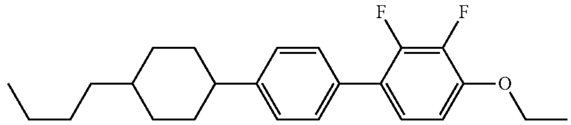

(N-1-3.7)

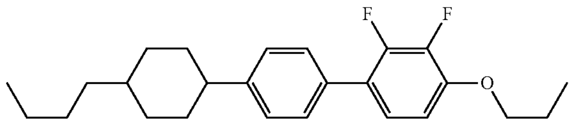

(N-1-3.7)

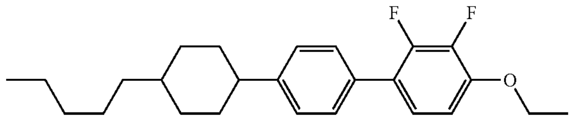

(N-1-3.10)

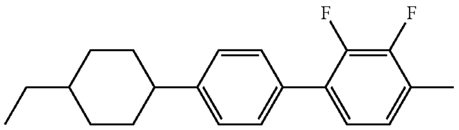

(N-1-3.11)

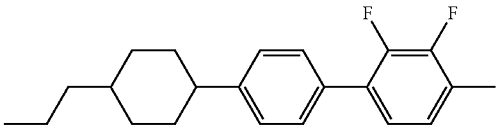

(N-1-3.20)

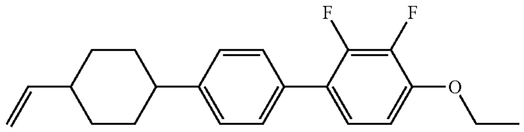

-continued (N-1-3.21)

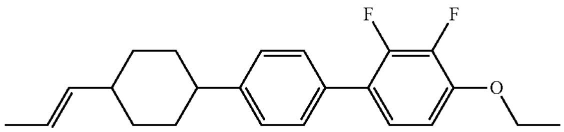

The compounds represented by formula (N-1-3.1) to formula (N-1-3.4), formula (N-1-3.6), and formula (N-1-3.21) can be used alone or in combination, and a combination of formula (N-1-3.1) and formula (N-1-3.2), or two or three kinds of combinations selected from formula (N-1-3.3), formula (N-1-3.4), and formula (N-1-3.6) is preferable. The preferable lower limit value of the content of the single compound or these compounds with respect to a total amount of the composition of the embodiment is equal to or greater than 5% by mass, equal to or greater than 10% by mass, equal to or greater than 13% by mass, equal to or greater than 15% by mass, equal to or greater than 17% by mass, or equal to or greater than 20% by mass. The preferable upper limit value of the content thereof with respect to a total amount of the composition of the embodiment is equal to or smaller than 35% by mass, equal to or smaller than 30% by mass, equal to or smaller than 28% by mass, equal to or smaller than 25% by mass, equal to or smaller than 23% by mass, equal to or smaller than 20% by mass, equal to or smaller than 18% by mass, equal to or smaller than 15% by mass, or equal to or smaller than 13% by mass.

The compound represented by general formula (N-1-4) is the following compound.

[Chem. 32]

(N-1-4)

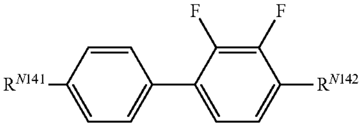

In the formula, $R^{N141}$ and $R^{N142}$ each independently represent the same meaning as $R^{N11}$ and $R^{N12}$ in general formula (N).

$R^{N141}$ and $R^{N142}$ each independently represent an alkyl group having 1 to 5 carbon atoms, an alkenyl group having 4 or 5 carbon atoms, or an alkoxy group having 1 to 4 carbon atoms, and preferably a methyl group, a propyl group, an ethoxy group, or a butoxy group.

The compound represented by general formula (N-1-4) can be used alone, and two or more compounds can also be used in combination. The kind of the compound which can be used in combination is not particularly limited, and compounds are suitably used in combination, in accordance with required performance such as solubility at a low temperature, a transition temperature, electrical reliability, or a birefringence. The number of kind of the compound used is one, two, three, four, or five or more, in one embodiment, for example.

In a case where the improvement of $\Delta\varepsilon$ is important, the content is preferably set to be high, in a case where the solubility at a low temperature is important, the effect is high by setting the content to be great, and in a case where $T_{NI}$ is important, the effect is high by setting the content to be low.

In a case of improving dropping marks or burning properties, the range of the content is preferably set to be moderate.

The preferable lower limit value of the content of the compound represented by formula (N-1-4) with respect to a total amount of the composition of the embodiment is equal to or greater than 3% by mass, equal to or greater than 5% by mass, equal to or greater than 7% by mass, equal to or greater than 10% by mass, equal to or greater than 13% by mass, equal to or greater than 15% by mass, equal to or greater than 17% by mass, or equal to or greater than 20% by mass. The preferable upper limit value of the content thereof with respect to a total amount of the composition of the embodiment is equal to or smaller than 35% by mass, equal to or smaller than 30% by mass, equal to or smaller than 28% by mass, equal to or smaller than 25% by mass, equal to or smaller than 23% by mass, equal to or smaller than 20% by mass, equal to or smaller than 18% by mass, equal to or smaller than 15% by mass, equal to or smaller than 13% by mass, equal to or smaller than 11% by mass, equal to or smaller than 10% by mass, or equal to or smaller than 8% by mass.

The compound represented by general formula (N-1-4) is preferably a compound selected from the compound group represented by formula (N-1-4.1) to formula (N-1-4.14), preferably a compound represented by formula (N-1-4.1) to formula (N-1-4.4), and preferably a compound represented by formula (N-1-4.1), formula (N-1-4.2), formula (N-1-4.4).

[Chem. 33]

(N-1-4.1)

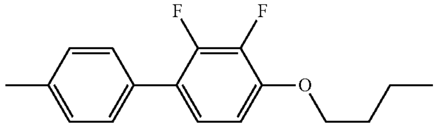

(N-1-4.2)

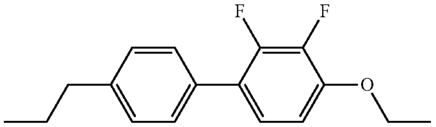

(N-1-4.3)

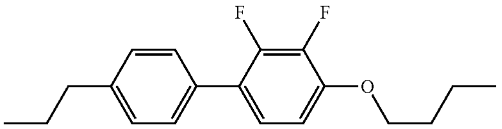

(N-1-4.4)

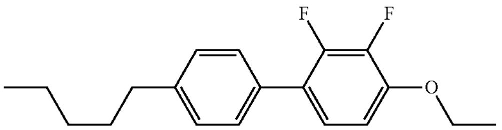

(N-1-4.11)

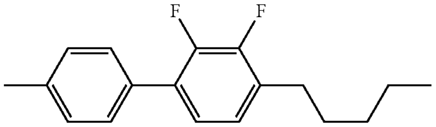

(N-1-4.12)

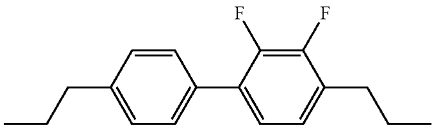

-continued (N-1-4.13)

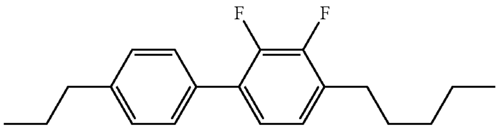

(N-1-4.14)

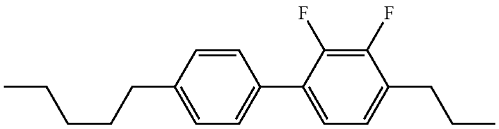

The compounds represented by formulae (N-1-4.1) to (N-1-4.14) can be used alone or in combination, and the preferable lower limit value of the content of the single compound or these compounds with respect to a total amount of the composition of the embodiment is equal to or greater than 3% by mass, equal to or greater than 5% by mass, equal to or greater than 7% by mass, equal to or greater than 10% by mass, equal to or greater than 13% by mass, equal to or greater than 15% by mass, equal to or greater than 17% by mass, or equal to or greater than 20% by mass. The preferable upper limit value of the content thereof with respect to a total amount of the composition of the embodiment is equal to or smaller than 35% by mass, equal to or smaller than 30% by mass, equal to or smaller than 28% by mass, equal to or smaller than 25% by mass, equal to or smaller than 23% by mass, equal to or smaller than 20% by mass, equal to or smaller than 18% by mass, equal to or smaller than 15% by mass, equal to or smaller than 13% by mass, equal to or smaller than 11% by mass, equal to or smaller than 10% by mass, or equal to or smaller than 8% by mass.

The compound represented by general formula (N-1-5) is the following compound.

[Chem. 34]

(N-1-5)

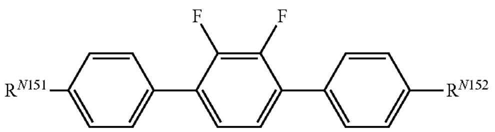

In the formula, $R^{N151}$ and $R^{N152}$ each independently represent the same meaning as $R^{N11}$ and $R^{N12}$ in general formula (N).

$R^{N151}$ and $R^{N12}$ each independently represent an alkyl group having 1 to 5 carbon atoms, an alkenyl group having 4 or 5 carbon atoms, or an alkoxy group having 1 to 4 carbon atoms, and preferably an ethyl group, a propyl group, or a butyl group.

The compound represented by general formula (N-1-5) can be used alone, and two or more compounds can also be used in combination. The kind of the compound which can be used in combination is not particularly limited, and compounds are suitably used in combination, in accordance with required performance such as solubility at a low temperature, a transition temperature, electrical reliability, or a birefringence. The number of kind of the compound used is one, two, three, four, or five or more, in one embodiment, for example.

In a case where the improvement of Δε is important, the content is preferably set to be high, in a case where the solubility at a low temperature is important, the effect is high by setting the content to be low, and in a case where $T_{NI}$ is important, the effect is high by setting the content to be great. In a case of improving dropping marks or burning properties, the range of the content is preferably set to be moderate.

The preferable lower limit value of the content of the compound represented by formula (N-1-5) with respect to a total amount of the composition of the embodiment is equal to or greater than 5% by mass, equal to or greater than 8% by mass, equal to or greater than 10% by mass, equal to or greater than 13% by mass, equal to or greater than 15% by mass, equal to or greater than 17% by mass, or equal to or greater than 20% by mass. The preferable upper limit value of the content thereof with respect to a total amount of the composition of the embodiment is equal to or smaller than 35% by mass, equal to or smaller than 33% by mass, equal to or smaller than 30% by mass, equal to or smaller than 28% by mass, equal to or smaller than 25% by mass, equal to or smaller than 23% by mass, equal to or smaller than 20% by mass, equal to or smaller than 18% by mass, equal to or smaller than 15% by mass, or equal to or smaller than 13% by mass.

The compound represented by general formula (N-1-5) is preferably a compound selected from the compound group represented by formula (N-1-5.1) to formula (N-1-5.6), and preferably a compound represented by formula (N-1-5.1), formula (N-1-5.2), and formula (N-1-5.4).

[Chem. 35]

(N-1-5.1)

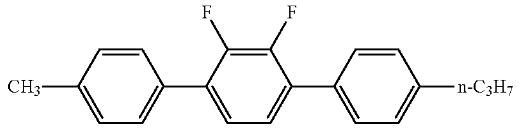

(N-1-5.2)

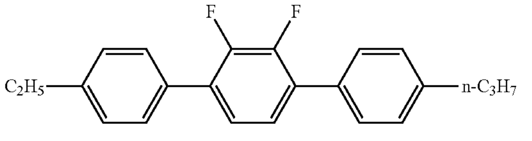

(N-1-5.3)

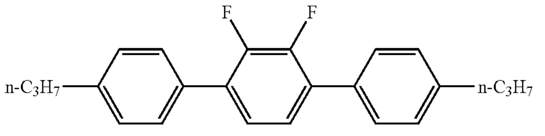

(N-1-5.4)

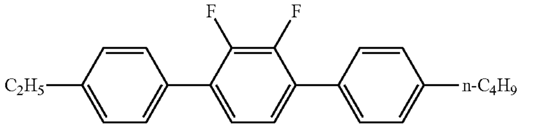

-continued (N-1-5.5)

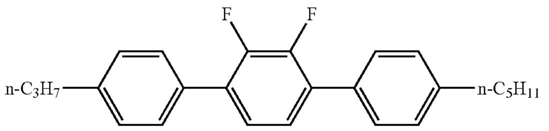

(N-1-5.6)

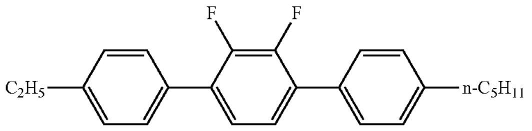

The compounds represented by formula (N-1-5.1), formula (N-1-5.2), and formula (N-1-5.4) can be used alone or in combination, and the preferable lower limit value of the content of the single compound or these compounds with respect to a total amount of the composition of the embodiment is equal to or greater than 5% by mass, equal to or greater than 8% by mass, equal to or greater than 10% by mass, equal to or greater than 13% by mass, equal to or greater than 15% by mass, equal to or greater than 17% by mass, or equal to or greater than 20% by mass. The preferable upper limit value of the content thereof with respect to a total amount of the composition of the embodiment is equal to or smaller than 35% by mass, equal to or smaller than 33% by mass, equal to or smaller than 30% by mass, equal to or smaller than 28% by mass, equal to or smaller than 25% by mass, equal to or smaller than 23% by mass, equal to or smaller than 20% by mass, equal to or smaller than 18% by mass, equal to or smaller than 15% by mass, or equal to or smaller than 13% by mass.

The compound represented by general formula (N-1-10) is the following compound.

[Chem. 36]

(N-1-10)

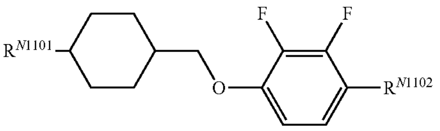

In the formula, $R^{N1101}$ and $R^{N1102}$ each independently represent the same meaning as $R^{N11}$ and $R^{N12}$ in general formula (N).

$R^{N1101}$ is preferably an alkyl group having 1 to 5 carbon atoms or an alkenyl group having 2 to 5 carbon atoms, and preferably an ethyl group, a propyl group, a butyl group, a vinyl group, or a 1-propenyl group. $R^{N1102}$ is preferably an alkyl group having 1 to 5 carbon atoms, an alkenyl group having 4 or 5 carbon atoms, or an alkoxy group having 1 to 4 carbon atoms, and preferably an ethoxy group, a propoxy group, or a butoxy group.

The compound represented by general formula (N-1-10) can be used alone or a combination of two or more compounds can also be used. The kind of the compound which can be used in combination is not particularly limited, and compounds are suitably used in combination, in accordance with required performance such as solubility at a low temperature, a transition temperature, electrical reliability, or a birefringence. The number of kind of the compound used is one, two, three, four, or five or more, in one embodiment of the embodiment, for example.

In a case where the improvement of Δε is important, the content is preferably set to be high, in a case where the solubility at a low temperature is important, the effect is high by setting the content to be high, and in a case where $T_{NI}$ is important, the effect is high by setting the content to be high. In a case of improving dropping marks or burning properties, the range of the content is preferably set to be moderate.

The preferable lower limit value of the content of the compound represented by formula (N-1-10) with respect to a total amount of the composition of the embodiment is equal to or greater than 5% by mass, equal to or greater than 10% by mass, equal to or greater than 13% by mass, equal to or greater than 15% by mass, equal to or greater than 17% by mass, or equal to or greater than 20% by mass. The preferable upper limit value of the content thereof with respect to a total amount of the composition of the embodiment is equal to or smaller than 35% by mass, equal to or smaller than 30% by mass, equal to or smaller than 28% by mass, equal to or smaller than 25% by mass, equal to or smaller than 23% by mass, equal to or smaller than 20% by mass, equal to or smaller than 18% by mass, equal to or smaller than 15% by mass, or equal to or smaller than 13% by mass.

The compound represented by general formula (N-1-10) is preferably a compound selected from the compound group represented by formula (N-1-10.1) to formula (N-1-10.21), preferably a compound represented by formulae (N-1-10.1) to (N-1-10.5), formula (N-1-10.20), and formula (N-1-10.21), and preferably a compound represented by formula (N-1-10.1), formula (N-1-10.2), formula (N-1-10.20), and formula (N-1-10.21).

[Chem. 37]

(N-1-10.1)

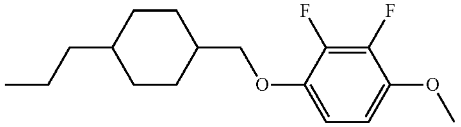

(N-1-10.2)

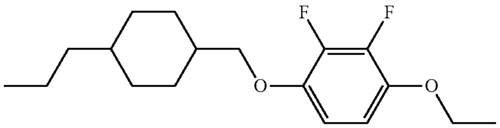

(N-1-10.3)

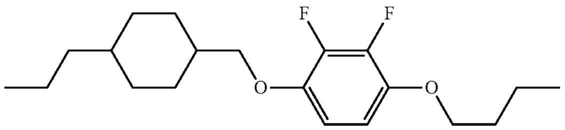

(N-1-10.4)

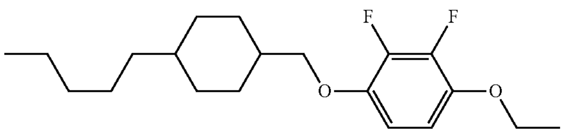

(N-1-10.5)

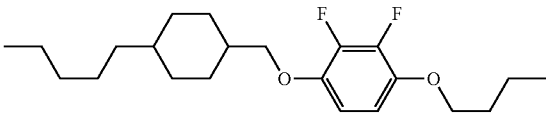

-continued (N-1-10.11)

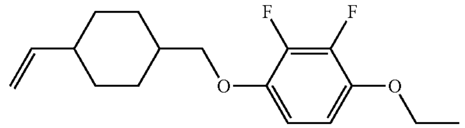

(N-1-10.12)

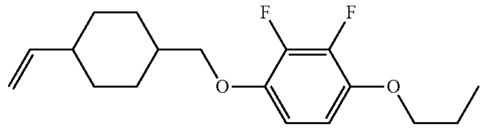

(N-1-10.13)

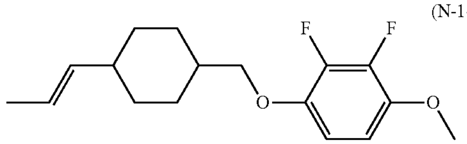

(N-1-10.14)

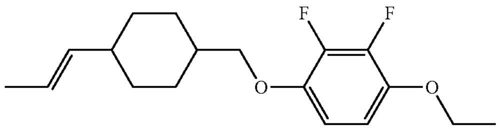

The compounds represented by formula (N-1-10.1), formula (N-1-10.2), formula (N-1-10.20), and formula (N-1-10.21) can be used alone or in combination, and the preferable lower limit value of the content of the single compound or these compounds with respect to a total amount of the composition of the embodiment is equal to or greater than 5% by mass, equal to or greater than 10% by mass, equal to or greater than 13% by mass, equal to or greater than 15% by mass, equal to or greater than 17% by mass, or equal to or greater than 20% by mass. The preferable upper limit value of the content thereof with respect to a total amount of the composition of the embodiment is equal to or smaller than 35% by mass, equal to or smaller than 30% by mass, equal to or smaller than 28% by mass, equal to or smaller than 25% by mass, equal to or smaller than 23% by mass, equal to or smaller than 20% by mass, equal to or smaller than 18% by mass, equal to or smaller than 15% by mass, or equal to or smaller than 13% by mass.

The compound represented by general formula (N-1-11) is the following compound.

[Chem. 38]

(N-1-11)

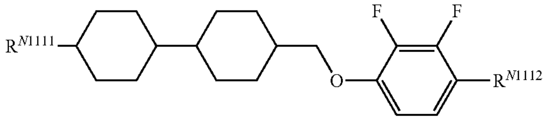

In the formula, $R^{N1111}$ and $R^{N1112}$ each independently represent the same meaning as $R^{N11}$ and $R^{N12}$ in general formula (N).

$R^{N1111}$ is preferably an alkyl group having 1 to 5 carbon atoms or an alkenyl group having 2 to 5 carbon atoms, and preferably an ethyl group, a propyl group, a butyl group, a vinyl group, or a 1-propenyl group. $R^{N1112}$ is preferably an alkyl group having 1 to 5 carbon atoms, an alkenyl group having 4 or 5 carbon atoms, or an alkoxy group having 1 to 4 carbon atoms, and preferably an ethoxy group, a propoxy group, or a butoxy group.

The compound represented by general formula (N-1-11) can be used alone or a combination of two or more compounds can also be used. The kind of the compound which can be used in combination is not particularly limited, and compounds are suitably used in combination, in accordance with required performance such as solubility at a low temperature, a transition temperature, electrical reliability, or a birefringence. The number of kind of the compound used is one, two, three, four, or five or more, in one embodiment, for example.

In a case where the improvement of Δε is important, the content is preferably set to be high, in a case where the solubility at a low temperature is important, the effect is high by setting the content to be low, and in a case where $T_{NI}$ is important, the effect is high by setting the content to be high. In a case of improving dropping marks or burning properties, the range of the content is preferably set to be moderate.

The preferable lower limit value of the content of the compound represented by formula (N-1-11) with respect to a total amount of the composition of the embodiment is equal to or greater than 5% by mass, equal to or greater than 10% by mass, equal to or greater than 13% by mass, equal to or greater than 15% by mass, equal to or greater than 17% by mass, or equal to or greater than 20% by mass. The preferable upper limit value of the content thereof with respect to a total amount of the composition of the embodiment is equal to or smaller than 35% by mass, equal to or smaller than 30% by mass, equal to or smaller than 28% by mass, equal to or smaller than 25% by mass, equal to or smaller than 23% by mass, equal to or smaller than 20% by mass, equal to or smaller than 18% by mass, equal to or smaller than 15% by mass, or equal to or smaller than 13% by mass.

The compound represented by general formula (N-1-11) is preferably a compound selected from the compound group represented by formula (N-1-11.1) to formula (N-1-11.15), preferably a compound represented by formulae (N-1-11.1) to (N-1-11.15), and preferably a compound represented by formula (N-1-11.2) and formula (N-1-11.4).

[Chem. 39]

(N-1-11.1)

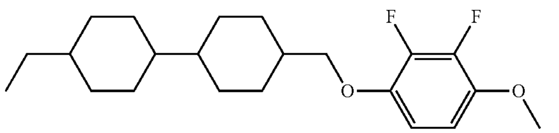

(N-1-11.2)

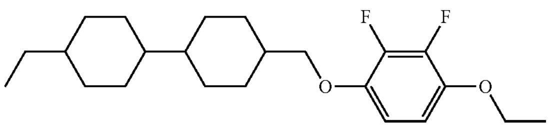

(N-1-11.3)

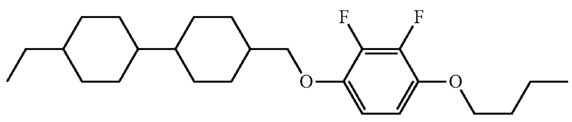

-continued (N-1-11.4)

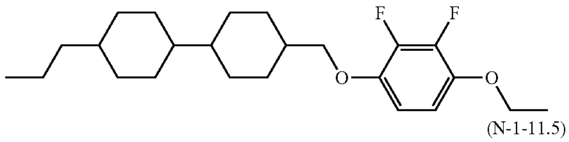

(N-1-11.5)

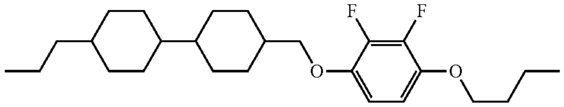

(N-1-11.11)

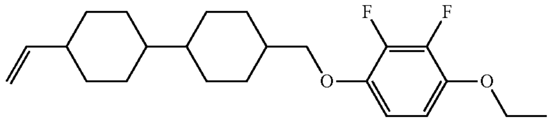

(N-1-11.12)

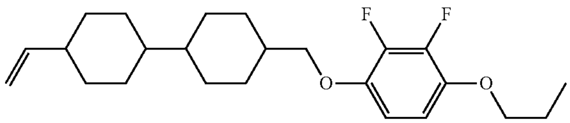

(N-1-11.13)

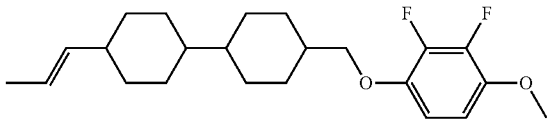

(N-1-11.14)

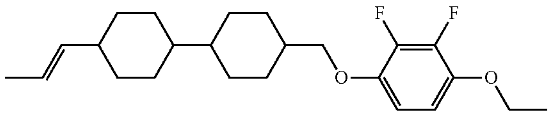

The compounds represented by formula (N-1-11.2) and formula (N-1-11.4) can be used alone or in combination, and the preferable lower limit value of the content of the single compound or these compounds with respect to a total amount of the composition of the embodiment is equal to or greater than 5% by mass, equal to or greater than 10% by mass, equal to or greater than 13% by mass, equal to or greater than 15% by mass, equal to or greater than 17% by mass, or equal to or greater than 20% by mass. The preferable upper limit value of the content thereof with respect to a total amount of the composition of the embodiment is equal to or smaller than 35% by mass, equal to or smaller than 30% by mass, equal to or smaller than 28% by mass, equal to or smaller than 25% by mass, equal to or smaller than 23% by mass, equal to or smaller than 20% by mass, equal to or smaller than 18% by mass, equal to or smaller than 15% by mass, or equal to or smaller than 13% by mass.

The compound represented by general formula (N-1-12) is the following compound.

[Chem. 40]

(N-1-12)

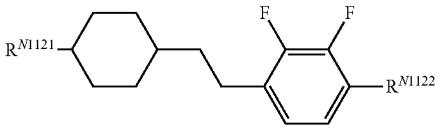

In the formula, $R^{N1121}$ and $R^{N1122}$ each independently represent the same meaning as $R^{N11}$ and $R^{N12}$ in general formula (N).

$R^{N1121}$ is preferably an alkyl group having 1 to 5 carbon atoms or an alkenyl group having 2 to 5 carbon atoms, and preferably an ethyl group, a propyl group, or a butyl group. $R^{N1122}$ is preferably an alkyl group having 1 to 5 carbon atoms, an alkenyl group having 4 or 5 carbon atoms, or an alkoxy group having 1 to 4 carbon atoms, and preferably an ethoxy group, a propoxy group, or a butoxy group.

The compound represented by general formula (N-1-12) can be used alone or a combination of two or more compounds can also be used. The kind of the compound which can be used in combination is not particularly limited, and compounds are suitably used in combination, in accordance with required performance such as solubility at a low temperature, a transition temperature, electrical reliability, or a birefringence. The number of kind of the compound used is one, two, three, four, or five or more, in one embodiment, for example.

In a case where the improvement of Δε is important, the content is preferably set to be high, in a case where the solubility at a low temperature is important, the effect is high by setting the content to be great, and in a case where $T_{NI}$ is important, the effect is high by setting the content to be great. In a case of improving dropping marks or burning properties, the range of the content is preferably set to be moderate.

The preferable lower limit value of the content of the compound represented by formula (N-1-12) with respect to a total amount of the composition of the embodiment is equal to or greater than 5% by mass, equal to or greater than 10% by mass, equal to or greater than 13% by mass, equal to or greater than 15% by mass, equal to or greater than 17% by mass, or equal to or greater than 20% by mass. The preferable upper limit value of the content thereof with respect to a total amount of the composition of the embodiment is equal to or smaller than 35% by mass, equal to or smaller than 30% by mass, equal to or smaller than 28% by mass, equal to or smaller than 25% by mass, equal to or smaller than 23% by mass, equal to or smaller than 20% by mass, equal to or smaller than 18% by mass, equal to or smaller than 15% by mass, or equal to or smaller than 13% by mass.

The compound represented by general formula (N-1-13) is the following compound.

[Chem. 41]

(N-1-13)

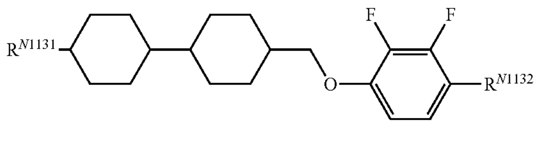

In the formula, $R^{N1131}$ and $R^{N1132}$ each independently represent the same meaning as $R^{N11}$ and $R^{N12}$ in general formula (N).

$R^{N1131}$ is preferably an alkyl group having 1 to 5 carbon atoms or an alkenyl group having 2 to 5 carbon atoms, and preferably an ethyl group, a propyl group, or a butyl group. $R^{N1132}$ is preferably an alkyl group having 1 to 5 carbon atoms, an alkenyl group having 4 or 5 carbon atoms, or an alkoxy group having 1 to 4 carbon atoms, and preferably an ethoxy group, a propoxy group, or a butoxy group.

The compound represented by general formula (N-1-13) can be used alone, and two or more compounds can also be used in combination. The kind of the compound which can be used in combination is not particularly limited, and compounds are suitably used in combination, in accordance with required performance such as solubility at a low temperature, a transition temperature, electrical reliability, or a birefringence. The number of kind of the compound used is one, two, three, four, or five or more, in one embodiment, for example.

In a case where the improvement of Δε is important, the content is preferably set to be high, in a case where the solubility at a low temperature is important, the effect is high by setting the content to be great, and in a case where $T_{NI}$ is important, the effect is high by setting the content to be great. In a case of improving dropping marks or burning properties, the range of the content is preferably set to be moderate.

The preferable lower limit value of the content of the compound represented by formula (N-1-13) with respect to a total amount of the composition of the embodiment is equal to or greater than 5% by mass, equal to or greater than 10% by mass, equal to or greater than 13% by mass, equal to or greater than 15% by mass, equal to or greater than 17% by mass, or equal to or greater than 20% by mass. The preferable upper limit value of the content thereof with respect to a total amount of the composition of the embodiment is equal to or smaller than 35% by mass, equal to or smaller than 30% by mass, equal to or smaller than 28% by mass, equal to or smaller than 25% by mass, equal to or smaller than 23% by mass, equal to or smaller than 20% by mass, equal to or smaller than 18% by mass, equal to or smaller than 15% by mass, or equal to or smaller than 13% by mass.

The compound represented by general formula (N-1-14) is the following compound.

[Chem. 42]

(N-1-14)

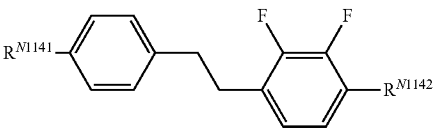

In the formula, $R^{N1141}$ and $R^{N1142}$ each independently represent the same meaning as $R^{N11}$ and $R^{N12}$ in general formula (N).)

$R^{N1141}$ is preferably an alkyl group having 1 to 5 carbon atoms or an alkenyl group having 2 to 5 carbon atoms, and preferably an ethyl group, a propyl group, or a butyl group. $R^{N1142}$ is preferably an alkyl group having 1 to 5 carbon atoms, an alkenyl group having 4 or 5 carbon atoms, or an alkoxy group having 1 to 4 carbon atoms, and preferably an ethoxy group, a propoxy group, or a butoxy group.

The compound represented by general formula (N-1-14) can be used alone or a combination of two or more compounds can also be used. The kind of the compound which can be used in combination is not particularly limited, and compounds are suitably used in combination, in accordance with required performance such as solubility at a low temperature, a transition temperature, electrical reliability, or a birefringence. The number of kind of the compound used is one, two, three, four, or five or more, in one embodiment of the embodiment, for example.

In a case where the improvement of Δε is important, the content is preferably set to be high, in a case where the solubility at a low temperature is important, the effect is high by setting the content to be great, and in a case where $T_{NI}$ is important, the effect is high by setting the content to be great. In a case of improving dropping marks or burning properties, the range of the content is preferably set to be moderate.

The preferable lower limit value of the content of the compound represented by formula (N-1-14) with respect to a total amount of the composition of the embodiment is equal to or greater than 5% by mass, equal to or greater than 10% by mass, equal to or greater than 13% by mass, equal to or greater than 15% by mass, equal to or greater than 17% by mass, or equal to or greater than 20% by mass. The preferable upper limit value of the content thereof with respect to a total amount of the composition of the embodiment is equal to or smaller than 35% by mass, equal to or smaller than 30% by mass, equal to or smaller than 28% by mass, equal to or smaller than 25% by mass, equal to or smaller than 23% by mass, equal to or smaller than 20% by mass, equal to or smaller than 18% by mass, equal to or smaller than 15% by mass, or equal to or smaller than 13% by mass.

The compound represented by general formula (N-1-15) is the following compound.

[Chem. 43]

(N-1-15)

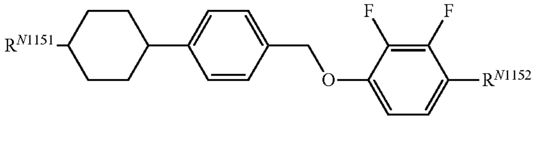

In the formula, $R^{N1151}$ and $R^{N1152}$ each independently represent the same meaning as $R^{N11}$ and $R^{N12}$ in general formula (N).

$R^{N1151}$ is preferably an alkyl group having 1 to 5 carbon atoms or an alkenyl group having 2 to 5 carbon atoms, and preferably an ethyl group, a propyl group, or a butyl group. $R^{N1152}$ is preferably an alkyl group having 1 to 5 carbon atoms, an alkenyl group having 4 or 5 carbon atoms, or an alkoxy group having 1 to 4 carbon atoms, and preferably an ethoxy group, a propoxy group, or a butoxy group.

The compound represented by general formula (N-1-15) can be used alone, and two or more compounds can also be used in combination. The kind of the compound which can be used in combination is not particularly limited, and compounds are suitably used in combination, in accordance with required performance such as solubility at a low temperature, a transition temperature, electrical reliability, or a birefringence. The number of kind of the compound used is one, two, three, four, or five or more, in one embodiment, for example.

In a case where the improvement of Δε is important, the content is preferably set to be high, in a case where the solubility at a low temperature is important, the effect is high by setting the content to be great, and in a case where $T_{NI}$ is important, the effect is high by setting the content to be great. In a case of improving dropping marks or burning properties, the range of the content is preferably set to be moderate.

The preferable lower limit value of the content of the compound represented by formula (N-1-15) with respect to a total amount of the composition of the embodiment is equal to or greater than 5% by mass, equal to or greater than 10% by mass, equal to or greater than 13% by mass, equal to or greater than 15% by mass, equal to or greater than 17% by mass, or equal to or greater than 20% by mass. The preferable upper limit value of the content thereof with respect to a total amount of the composition of the embodiment is equal to or smaller than 35% by mass, equal to or smaller than 30% by mass, equal to or smaller than 28% by mass, equal to or smaller than 25% by mass, equal to or smaller than 23% by mass, equal to or smaller than 20% by mass, equal to or smaller than 18% by mass, equal to or smaller than 15% by mass, or equal to or smaller than 13% by mass.

The compound represented by general formula (N-1-16) is the following compound.

[Chem. 44]

(N-1-16)

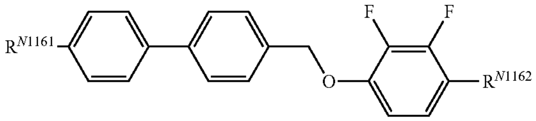

In the formula, $R^{N1161}$ and $R^{N1162}$ each independently represent the same meaning as $R^{N11}$ and $R^{N12}$ in general formula (N).

$R^{N1161}$ is preferably an alkyl group having 1 to 5 carbon atoms or an alkenyl group having 2 to 5 carbon atoms, and preferably an ethyl group, a propyl group, or a butyl group. $R^{N1162}$ is preferably an alkyl group having 1 to 5 carbon atoms, an alkenyl group having 4 or 5 carbon atoms, or an alkoxy group having 1 to 4 carbon atoms, and preferably an ethoxy group, a propoxy group, or a butoxy group.

The compound represented by general formula (N-1-16) can be used alone, and two or more compounds can also be used in combination. The kind of the compound which can be used in combination is not particularly limited, and compounds are suitably used in combination, in accordance with required performance such as solubility at a low temperature, a transition temperature, electrical reliability, or a birefringence. The number of kind of the compound used is one, two, three, four, or five or more, in one embodiment, for example.

In a case where the improvement of Δε is important, the content is preferably set to be high, in a case where the solubility at a low temperature is important, the effect is high by setting the content to be great, and in a case where $T_{NI}$ is important, the effect is high by setting the content to be great. In a case of improving dropping marks or burning properties, the range of the content is preferably set to be moderate.

The preferable lower limit value of the content of the compound represented by formula (N-1-16) with respect to a total amount of the composition of the embodiment is equal to or greater than 5% by mass, equal to or greater than 10% by mass, equal to or greater than 13% by mass, equal to or greater than 15% by mass, equal to or greater than 17% by mass, or equal to or greater than 20% by mass. The preferable upper limit value of the content thereof with respect to a total amount of the composition of the embodiment is equal to or smaller than 35% by mass, equal to or smaller than 30% by mass, equal to or smaller than 28% by mass, equal to or smaller than 25% by mass, equal to or smaller than 23% by mass, equal to or smaller than 20% by mass, equal to or smaller than 18% by mass, equal to or smaller than 15% by mass, or equal to or smaller than 13% by mass.

The compound represented by general formula (N-1-17) is the following compound.

[Chem. 45]

(N-1-17)

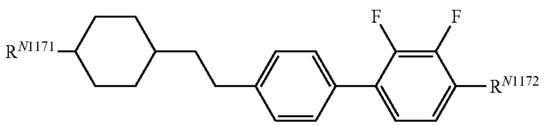

In the formula, $R^{N1171}$ and $R^{N1172}$ each independently represent the same meaning as $R^{N11}$ and $R^{N12}$ in general formula (N).

$R^{N1171}$ is preferably an alkyl group having 1 to 5 carbon atoms or an alkenyl group having 2 to 5 carbon atoms, and preferably an ethyl group, a propyl group, or a butyl group. $R^{N1172}$ is preferably an alkyl group having 1 to 5 carbon atoms, an alkenyl group having 4 or 5 carbon atoms, or an alkoxy group having 1 to 4 carbon atoms, and preferably an ethoxy group, a propoxy group, or a butoxy group.

The compound represented by general formula (N-1-17) can be used alone or a combination of two or more compounds can also be used. The kind of the compound which can be used in combination is not particularly limited, and compounds are suitably used in combination, in accordance with required performance such as solubility at a low temperature, a transition temperature, electrical reliability, or a birefringence. The number of kind of the compound used is one, two, three, four, or five or more, in one embodiment, for example.

In a case where the improvement of Δε is important, the content is preferably set to be high, in a case where the solubility at a low temperature is important, the effect is high by setting the content to be great, and in a case where $T_{NI}$ is important, the effect is high by setting the content to be great. In a case of improving dropping marks or burning properties, the range of the content is preferably set to be moderate.

The preferable lower limit value of the content of the compound represented by formula (N-1-17) with respect to a total amount of the composition of the embodiment is equal to or greater than 5% by mass, equal to or greater than 10% by mass, equal to or greater than 13% by mass, equal to or greater than 15% by mass, equal to or greater than 17% by mass, or equal to or greater than 20% by mass. The preferable upper limit value of the content thereof with respect to a total amount of the composition of the embodiment is equal to or smaller than 35% by mass, equal to or smaller than 30% by mass, equal to or smaller than 28% by mass, equal to or smaller than 25% by mass, equal to or smaller than 23% by mass, equal to or smaller than 20% by mass, equal to or smaller than 18% by mass, equal to or smaller than 15% by mass, or equal to or smaller than 13% by mass.

The compound represented by general formula (N-1-18) is the following compound.

[Chem. 46]

(N-1-18)

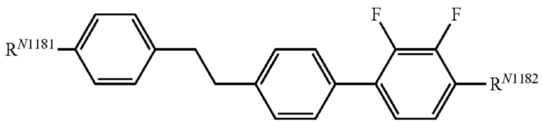

In the formula, $R^{N1181}$ and $R^{N1182}$ each independently represent the same meaning as $R^{N11}$ and $R^{N12}$ in general formula (N).

$R^{N1181}$ is preferably an alkyl group having 1 to 5 carbon atoms or an alkenyl group having 2 to 5 carbon atoms, and preferably a methyl group, an ethyl group, a propyl group, or a butyl group. $R^{N1182}$ is preferably an alkyl group having 1 to 5 carbon atoms, an alkenyl group having 4 or 5 carbon atoms, or an alkoxy group having 1 to 4 carbon atoms, and preferably an ethoxy group, a propoxy group, or a butoxy group.

The compound represented by general formula (N-1-18) can be used alone or a combination of two or more compounds can also be used. The kind of the compound which can be used in combination is not particularly limited, and compounds are suitably used in combination, in accordance with required performance such as solubility at a low temperature, a transition temperature, electrical reliability, or a birefringence. The number of kind of the compound used is one, two, three, four, or five or more, in one embodiment, for example.

In a case where the improvement of Δε is important, the content is preferably set to be high, in a case where the solubility at a low temperature is important, the effect is high by setting the content to be great, and in a case where $T_{NI}$ is important, the effect is high by setting the content to be great. In a case of improving dropping marks or burning properties, the range of the content is preferably set to be moderate.

The preferable lower limit value of the content of the compound represented by formula (N-1-18) with respect to a total amount of the composition of the embodiment is equal to or greater than 5% by mass, equal to or greater than 10% by mass, equal to or greater than 13% by mass, equal to or greater than 15% by mass, equal to or greater than 17% by mass, or equal to or greater than 20% by mass. The preferable upper limit value of the content thereof with respect to a total amount of the composition of the embodiment is equal to or smaller than 35% by mass, equal to or smaller than 30% by mass, equal to or smaller than 28% by mass, equal to or smaller than 25% by mass, equal to or smaller than 23% by mass, equal to or smaller than 20% by mass, equal to or smaller than 18% by mass, equal to or smaller than 15% by mass, or equal to or smaller than 13% by mass.

The compound represented by general formula (N-1-18) is preferably a compound selected from the compound group represented by formula (N-1-18.1) to formula (N-1-18.5), preferably a compound represented by formulae (N-1-18.1) to (N-1-18.3), and preferably a compound represented by formula (N-1-18.2) and formula (N-1-18.3).

[Chem. 47]

(N-1-18.1)

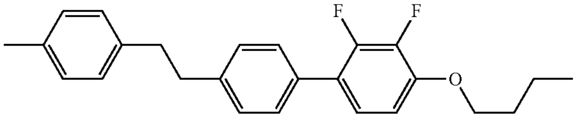

(N-1-18.2)

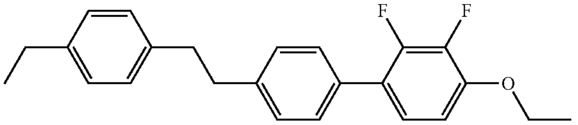

(N-1-18.3)

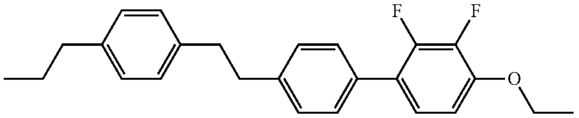

(N-1-18.4)

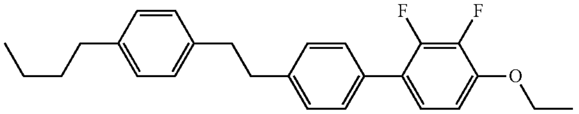

(N-1-18.5)

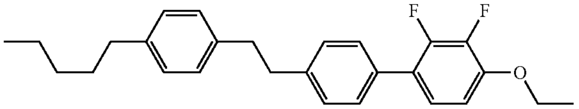

The compound represented by general formula (N-1-20) is the following compound.

[Chem. 48]

(N-1-20)

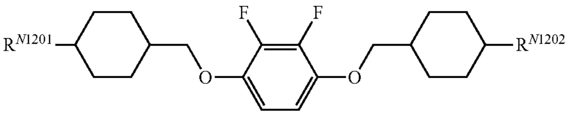

In the formula, $R^{N1201}$ and $R^{N1202}$ each independently represent the same meaning as $R^{N11}$ and $R^{N12}$ in general formula (N).

$R^{N1201}$ and $R^{N1202}$ are each independently preferably an alkyl group having 1 to 5 carbon atoms or an alkenyl group having 2 to 5 carbon atoms, and preferably an ethyl group, a propyl group, or a butyl group.

The compound represented by general formula (N-1-20) can be used alone or a combination of two or more compounds can also be used. The kind of the compound which can be used in combination is not particularly limited, and compounds are suitably used in combination, in accordance with required performance such as solubility at a low temperature, a transition temperature, electrical reliability, or a birefringence. The number of kind of the compound used is one, two, three, four, or five or more, in one embodiment, for example.

In a case where the improvement of Δε is important, the content is preferably set to be high, in a case where the solubility at a low temperature is important, the effect is high by setting the content to be great, and in a case where $T_{NI}$ is important, the effect is high by setting the content to be great. In a case of improving dropping marks or burning properties, the range of the content is preferably set to be moderate.

The preferable lower limit value of the content of the compound represented by formula (N-1-20) with respect to a total amount of the composition of the embodiment is equal to or greater than 5% by mass, equal to or greater than 10% by mass, equal to or greater than 13% by mass, equal to or greater than 15% by mass, equal to or greater than 17% by mass, or equal to or greater than 20% by mass. The preferable upper limit value of the content thereof with respect to a total amount of the composition of the embodiment is equal to or smaller than 35% by mass, equal to or smaller than 30% by mass, equal to or smaller than 28% by mass, equal to or smaller than 25% by mass, equal to or smaller than 23% by mass, equal to or smaller than 20% by mass, equal to or smaller than 18% by mass, equal to or smaller than 15% by mass, or equal to or smaller than 13% by mass.

The compound represented by general formula (N-1-21) is the following compound.

[Chem. 49]

(N-1-21)

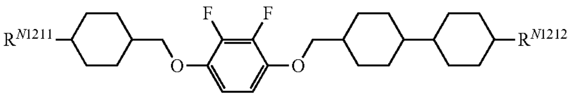

In the formula, $R^{N1211}$ and $R^{N1212}$ each independently represent the same meaning as $R^{N11}$ and $R^{N12}$ in general formula (N).

$R^{N121}$ and $R^{N1212}$ are each independently preferably an alkyl group having 1 to 5 carbon atoms or an alkenyl group having 2 to 5 carbon atoms, and preferably an ethyl group, a propyl group, or a butyl group.

The compound represented by general formula (N-1-21) can be used alone or a combination of two or more compounds can also be used. The kind of the compound which can be used in combination is not particularly limited, and compounds are suitably used in combination, in accordance with required performance such as solubility at a low temperature, a transition temperature, electrical reliability, or a birefringence. The number of kind of the compound used is one, two, three, four, or five or more, in one embodiment, for example.

In a case where the improvement of Δε is important, the content is preferably set to be high, in a case where the solubility at a low temperature is important, the effect is high by setting the content to be great, and in a case where $T_{NI}$ is important, the effect is high by setting the content to be great. In a case of improving dropping marks or burning properties, the range of the content is preferably set to be moderate.

The preferable lower limit value of the content of the compound represented by formula (N-1-21) with respect to a total amount of the composition of the embodiment is equal to or greater than 5% by mass, equal to or greater than 10% by mass, equal to or greater than 13% by mass, equal to or greater than 15% by mass, equal to or greater than 17% by mass, or equal to or greater than 20% by mass. The preferable upper limit value of the content thereof with respect to a total amount of the composition of the embodiment is equal to or smaller than 35% by mass, equal to or smaller than 30% by mass, equal to or smaller than 28% by mass, equal to or smaller than 25% by mass, equal to or smaller than 23% by mass, equal to or smaller than 20% by mass, equal to or smaller than 18% by mass, equal to or smaller than 15% by mass, or equal to or smaller than 13% by mass.

The compound represented by general formula (N-1-22) is the following compound.

[Chem. 50]

(N-1-22)

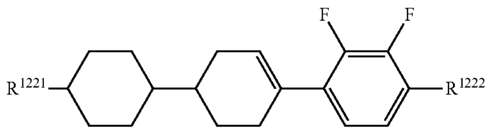

In the formula, $R^{N1221}$ and $R^{N1222}$ each independently represent the same meaning as $R^{N11}$ and $R^{N12}$ in general formula (N).

$R^{N1221}$ and $R^{N1222}$ are each independently preferably an alkyl group having 1 to 5 carbon atoms or an alkenyl group having 2 to 5 carbon atoms, and preferably an ethyl group, a propyl group, or a butyl group.

The compound represented by general formula (N-1-22) can be used alone, and two or more compounds can also be used in combination. The kind of the compound which can be used in combination is not particularly limited, and compounds are suitably used in combination, in accordance with required performance such as solubility at a low temperature, a transition temperature, electrical reliability, or a birefringence. The number of kind of the compound used is one, two, three, four, or five or more, in one embodiment, for example.

In a case where the improvement of Δε is important, the content is preferably set to be high, in a case where the solubility at a low temperature is important, the effect is high by setting the content to be great, and in a case where $T_{NI}$ is important, the effect is high by setting the content to be great. In a case of improving dropping marks or burning properties, the range of the content is preferably set to be moderate.

The preferable lower limit value of the content of the compound represented by formula (N-1-21) with respect to a total amount of the composition of the embodiment is equal to or greater than 1% by mass, equal to or greater than 5% by mass, equal to or greater than 10% by mass, equal to or greater than 13% by mass, equal to or greater than 15% by mass, equal to or greater than 17% by mass, or equal to or greater than 20% by mass. The preferable upper limit value of the content thereof with respect to a total amount of the composition of the embodiment is equal to or smaller than 35% by mass, equal to or smaller than 30% by mass, equal to or smaller than 28% by mass, equal to or smaller than 25% by mass, equal to or smaller than 23% by mass, equal to or smaller than 20% by mass, equal to or smaller than 18% by mass, equal to or smaller than 15% by mass, equal to or smaller than 13% by mass, equal to or smaller than 10% by mass, or equal to or smaller than 5% by mass.

The compound represented by general formula (N-1-22) is preferably a compound selected from the compound group represented by formula (N-1-22.1) to formula (N-1-22.12), preferably a compound represented by formulae (N-1-22.1) to (N-1-22.5), and preferably a compound represented by formulae (N-1-22.1) to (N-1-22.4).

[Chem. 51]

(N-1-22.1)

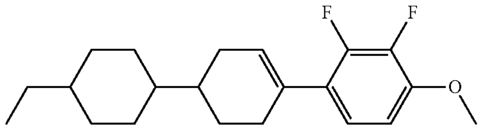

(N-1-22.2)

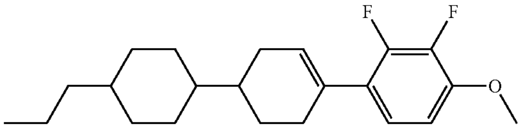

(N-1-22.3)

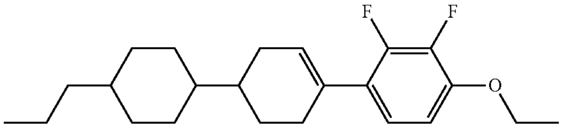

(N-1-22.4)

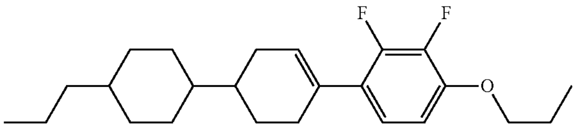

(N-1-22.5)

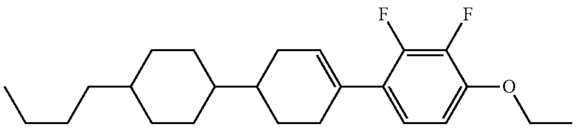

(N-1-22.6)

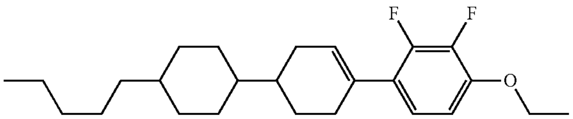

(N-1-22.11)

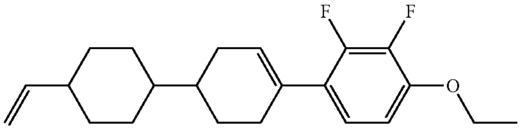

(N-1-22.12)

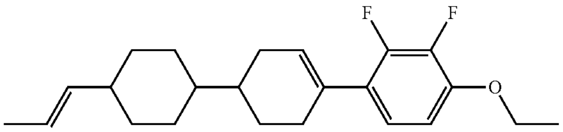

The compound represented by general formula (N-3) is preferably a compound selected from the compound group represented by general formula (N-3-2).

[Chem. 52]

(N-3-2)

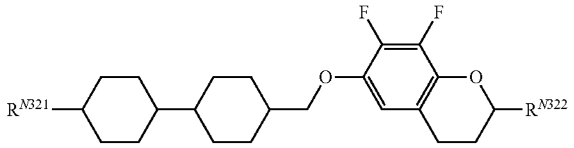

In the formula, $R^{N321}$ and $R^{N322}$ each independently represent the same meaning as $R^{N11}$ and $R^{N12}$ in general formula (N).

$R^{N321}$ and $R^{N322}$ are preferably an alkyl group having 1 to 5 carbon atoms or an alkenyl group having 2 to 5 carbon atoms, and preferably a propyl group or a pentyl group.

The compound represented by general formula (N-3-2) can be used alone, and two or more compounds can also be used in combination. The kind of the compound which can be used in combination is not particularly limited, and compounds are suitably used in combination, in accordance with required performance such as solubility at a low temperature, a transition temperature, electrical reliability, or a birefringence. The number of kind of the compound used is one, two, three, four, or five or more, in one embodiment, for example.

In a case where the improvement of Δε is important, the content is preferably set to be high, in a case where the solubility at a low temperature is important, the effect is high by setting the content to be great, and in a case where $T_{NI}$ is important, the effect is high by setting the content to be low. In a case of improving dropping marks or burning properties, the range of the content is preferably set to be moderate.

The preferable lower limit value of the content of the compound represented by formula (N-3-2) with respect to a total amount of the composition of the embodiment is equal to or greater than 3% by mass, equal to or greater than 5% by mass, equal to or greater than 10% by mass, equal to or greater than 13% by mass, equal to or greater than 15% by mass, equal to or greater than 17% by mass, equal to or greater than 20% by mass, equal to or greater than 23% by mass, equal to or greater than 25% by mass, equal to or greater than 27% by mass, equal to or greater than 30% by mass, equal to or greater than 33% by mass, or equal to or greater than 35% by mass. The preferable upper limit value of the content thereof with respect to a total amount of the composition of the embodiment is equal to or smaller than 50% by mass, equal to or smaller than 40% by mass, equal to or smaller than 38% by mass, equal to or smaller than 35% by mass, equal to or smaller than 33% by mass, equal to or smaller than 30% by mass, equal to or smaller than 28% by mass, equal to or smaller than 25% by mass, equal to or smaller than 23% by mass, equal to or smaller than 20% by mass, equal to or smaller than 18% by mass, equal to or smaller than 15% by mass, equal to or smaller than 13% by mass, equal to or smaller than 10% by mass, equal to or smaller than 8% by mass, equal to or smaller than 7% by mass, equal to or smaller than 6% by mass, or equal to or smaller than 5% by mass.

The compound represented by general formula (N-3-2) is preferably a compound selected from the compound group represented by formula (N-3-2.1) to formula (N-3-2.3).

[Chem. 53]

(N-3-2.1)

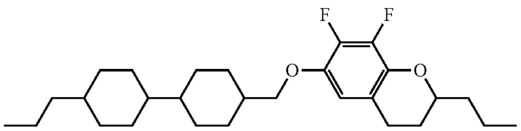

(N-3-2.2)

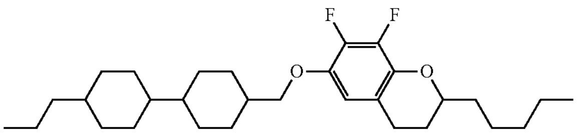

(N-3-2.3)

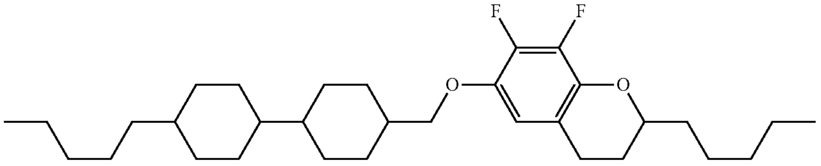

The liquid crystal composition may further include a compound represented by general formula (L):

[Chem. 54]

$$R^{L1}—A^{L1}—Z^{L1}—(A^{L2}—Z^{L2})_{nL1}—A^{L3}—R^{L2} \quad (L)$$

In formula (L), $R^{L1}$ and $R^{L2}$ each independently represent an alkyl group having 1 to 8 carbon atoms, one or two or more —$CH_2$—'s not adjacent to each other in the alkyl group each may be independently substituted with —CH═CH—, —C≡C—, —O—, —CO—, —COO—, or —OCO—, $n^{L1}$ represents 0, 1, 2, or 3, $A^{L1}$, $A^{L2}$, and $A^{L3}$ each independently represent a group selected from the group consisting of (a) a 1,4-cyclohexylene group (one —$CH_2$— or two or more —$CH_2$—'s not adjacent to each other present in this group may be substituted with —O—), (b) a 1,4-phenylene group (one —CH═ or two or more —CH═'s not adjacent to each other present in this group may be substituted with —N═), and (c) a naphthalene-2,6-diyl group, a 1,2,3,4-tetrahydronaphthalene-2,6-diyl group, or a decahydronaphthalene-2,6-diyl group (one —CH═ or two or more —CH═'s not adjacent to each other present in the naphthalene-2,6-diyl group or the 1,2,3,4-tetrahydronaphthalene-2,6-diyl group may be substituted with —N═), the group (a), the group (b), and the group (c) each may be independently substituted with a cyano group, a fluorine atom, or a chlorine atom, $Z^{L1}$ and $Z^{L2}$ each independently represent a single bond, $—CH_2CH_2—$, $—(CH_2)—$, $—OCH_2—$, $—CH_2O—$, —COO—, —OCO—, $—OCF_2—$, $—CF_2O—$, —CH═N—N═CH—, —CH═CH—, —CF═CF—, or —C≡C—, when $n^{L1}$ is 2 or 3 and a plurality of $A^{L2}$'s are present, these may be the same or different, and when $n^{L1}$ is 2 or 3 and a plurality of $Z^{L2}$'s are present, these may be the same or different, exclusive of compounds represented by general formula (N-1), (N-2), and (N-3).

The compound represented by general formula (L) corresponds to a compound (value of Δε is −2 to 2) which is substantially dielectrically neutral. The compound represented by general formula (L) can be used alone or in combination. The kind of the compound which can be used in combination is not particularly limited, and compounds are suitably used in combination, in accordance with desired performance such as solubility at a low temperature, a transition temperature, electrical reliability, or a birefringence. The number of kind of the compound used is one in one embodiment, for example. Alternatively, in another embodiment, the number thereof is one, two, three, four, five, six, seven, eight, nine, or ten or more.

In the composition of the embodiment, it is necessary that the content of the compound represented by general formula (L) is suitably adjusted in accordance with required performance such as solubility at a low temperature, a transition temperature, electrical reliability, a birefringence, process suitability, dropping marks, burning, or dielectric anisotropy.

The preferable lower limit value of the content of the compound represented by formula (L) with respect to a total amount of the composition of the embodiment is equal to or greater than 1% by mass, equal to or greater than 10% by mass, equal to or greater than 20% by mass, equal to or greater than 30% by mass, equal to or greater than 40% by mass, equal to or greater than 50% by mass, equal to or greater than 55% by mass, equal to or greater than 60% by mass, equal to or greater than 65% by mass, equal to or greater than 70% by mass, equal to or greater than 75% by mass, and equal to or greater than 80% by mass. The preferable upper limit value of the content thereof is equal to or smaller than 95% by mass, equal to or smaller than 85% by mass, equal to or smaller than 75% by mass, equal to or smaller than 65% by mass, equal to or smaller than 55% by mass, equal to or smaller than 45% by mass, equal to or smaller than 35% by mass, equal to or smaller than 25% by mass, and equal to or smaller than 20% by mass.

In a case where a viscosity of the composition of the embodiment is maintained to be low and a composition having a high response speed is necessary, it is preferable that the lower limit value is high and the upper limit value is high. In addition, in a case where Tni of the composition of the embodiment is maintained to be high and a composition having excellent temperature stability is necessary, it is preferable that the lower limit value is high and the upper limit value is high. In a case where it is desired to increase dielectric anisotropy for maintaining a driving voltage to be low, it is preferable that the lower limit value is low and the upper limit value is low.

In a case where the reliability is important, both of $R^{L1}$ and $R^{L2}$ are preferably an alkyl group, in a case where a decrease in volatility of the compound is important, both of $R^{L1}$ and $R^{L2}$ are preferably an alkoxy group, and in a case where a decrease in viscosity is important, at least one thereof is preferably an alkenyl group.

The number of halogen atoms present in a molecule is preferably 0, 1, 2, or 3, preferably 0 or 1, and in a case where compatibility with other liquid crystal molecules is important, the number thereof is preferably 1.

In a case where a ring structure, to which $R^{L1}$ and $R^{L2}$ are bonded, is a phenyl group (aromatic group), $R^{L1}$ and $R^{L2}$ are preferably a linear alkyl group having 1 to 5 carbon atoms, a linear alkoxy group having 1 to 4 carbon atoms, and an alkenyl group having 4 or 5 carbon atoms, and in a case where the structure, to which these are bonded, is a saturated ring structure of cyclohexane, pyran, and dioxane, $R^{L1}$ and $R^{L2}$ are preferably a linear alkyl group having 1 to 5 carbon atoms, a linear alkoxy group having 1 to 4 carbon atoms, and a linear alkenyl group having 2 to 5 carbon atoms. In order to stabilize a nematic phase, a total number of carbon atoms and oxygen atoms, in a case where oxygen atoms are present, is preferably equal to or smaller than 5 and the structure thereof is preferably linear.

The alkenyl group is preferably selected from groups represented by any of formula (R1) to formula (R5) (each black point in each formula represents atomic bonding).

[Chem. 55]

(R1)

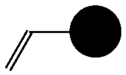

(R2)

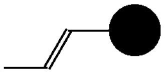

(R3)

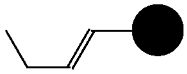

(R4)

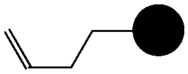

(R5)

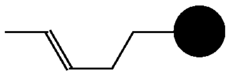

In a case where the response speed is important, $n^{L1}$ is preferably 0, in a case of improving the upper limit temperature of the nematic phase, $n^{L1}$ is preferably 2 or 3, and in a case of keeping a balance between these, $n^{L1}$ is preferably 1. In addition, in order to satisfy the properties required as the composition, a combination of compounds having different values is preferable.

$A^{L1}$, $A^{L2}$, and $A^{L3}$ are preferably an aromatic group, in a case where a value greater than Δn is required to obtain, and preferably an aliphatic group, in order to improve a response speed. $A^{L1}$, $A^{L2}$, and $A^{L3}$ each independently preferably represent a trans-1,4-cyclohexylene group, a 1,4-phenylene group, a 2-fluoro-1,4-phenylene group, a 3-fluoro-1,4-phenylene group, a 3,5-difluoro-1,4-phenylene group, a 1,4-cyclohexenylene group, a 1,4-bicyclo [2.2.2]octylene group, a piperidine-1,4-diyl group, a naphthalene-2,6-diyl group, a decahydronaphthalene-2,6-diyl group, or a 1,2,3,4-tetrahydronaphthalene-2,6-diyl group, more preferably represent the following structure:

[Chem. 56]

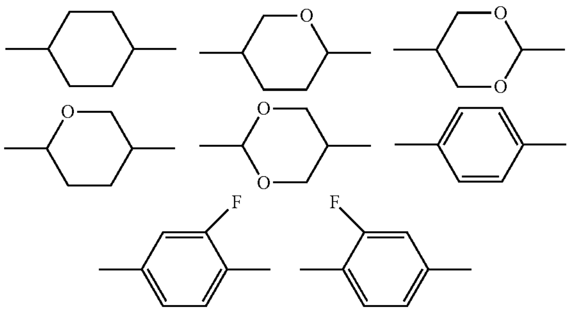

and more preferably represent a trans-1,4-cyclohexylene group or a 1,4-phenylene group.

In a case where the response speed is important, $Z^{L1}$ and $Z^{L2}$ are preferably a single bond.

The number of halogen atoms in a molecule of the compound represented by general formula (L) is preferably 0 or 1.

The compound represented by general formula (L) is preferably a compound selected from the compound group represented by general formula (L-1) to (L-7).

The compound represented by general formula (L-1) is the following compound.

[Chem. 57]

(L-1)

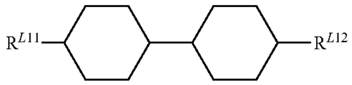

In the formula, $R^{L11}$ and $R^{L12}$ each independently represent the same meaning as $R^{L1}$ and $R^{L2}$ in general formula (L).

$R^{L11}$ and $R^{L12}$ are preferably a linear alkyl group having 1 to 5 carbon atoms, a linear alkoxy group having 1 to 4 carbon atoms, and a linear alkenyl group having 2 to 5 carbon atoms.

The compound represented by general formula (L-1) can be used alone, and two or more compounds can also be used in combination. The kind of the compound which can be used in combination is not particularly limited, and compounds are suitably used in combination, in accordance with required performance such as solubility at a low temperature, a transition temperature, electrical reliability, or a birefringence. The number of kind of the compound used is one, two, three, four, or five or more, in one embodiment, for example.

The preferable lower limit value of the content thereof with respect to a total amount of the composition of the embodiment is equal to or greater than 1% by mass, equal to or greater than 2% by mass, equal to or greater than 3% by mass, equal to or greater than 5% by mass, equal to or greater than 7% by mass, equal to or greater than 10% by mass, equal to or greater than 15% by mass, equal to or greater than 20% by mass, equal to or greater than 25% by mass, equal to or greater than 30% by mass, equal to or greater than 35% by mass, equal to or greater than 40% by mass, equal to or greater than 45% by mass, equal to or greater than 50% by mass, or equal to or greater than 55% by mass. The preferable upper limit value of the content thereof with respect to a total amount of the composition of the embodiment is equal to or smaller than 95% by mass, equal to or smaller than 90% by mass, equal to or smaller than 85% by mass, equal to or smaller than 80% by mass, equal to or smaller than 75% by mass, equal to or smaller than 70% by mass, equal to or smaller than 65% by mass, equal to or smaller than 60% by mass, equal to or smaller than 55% by mass, equal to or smaller than 50% by mass, equal to or smaller than 45% by mass, equal to or smaller than 40% by mass, equal to or smaller than 35% by mass, equal to or smaller than 30% by mass, or equal to or smaller than 25% by mass.

In a case where a viscosity of the composition of the embodiment is maintained to be low and a composition having a high response speed is necessary, it is preferable that the lower limit value is high and the upper limit value is high. In addition, in a case where Tni of the composition of the embodiment is maintained to be high and a composition having excellent temperature stability is necessary, it is preferable that the lower limit value is moderate and the upper limit value is moderate. In a case where it is desired to increase dielectric anisotropy for maintaining a driving voltage to be low, it is preferable that the lower limit value is low and the upper limit value is low.

The compound represented by general formula (L-1) is preferably a compound selected from the compound group represented by general formula (L-1-1).

[Chem. 58]

(L-1-1)

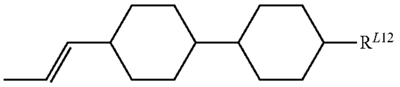

In the formula, $R^{L12}$ represents the same meaning as the meaning in general formula (L-1).

The compound represented by general formula (L-1-1) is preferably a compound selected from the compound group represented by formula (L-1-1.1) to formula (L-1-1.3), preferably a compound represented by formula (L-1-1.2) or formula (L-1-1.3), and preferably a compound represented by formula (L-1-1.3).

[Chem. 59]

(L-1-1.1)

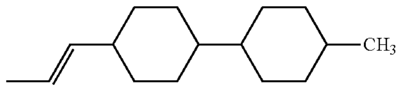

(L-1-1.2)

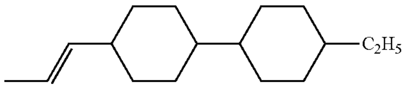

(L-1-1.3)

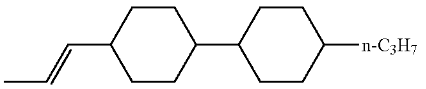

The preferable lower limit value of the content of the compound represented by formula (L-1-1.3) with respect to a total amount of the composition of the embodiment is equal to or greater than 1% by mass, equal to or greater than 2% by mass, equal to or greater than 3% by mass, equal to or greater than 5% by mass, equal to or greater than 7% by mass, or equal to or greater than 10% by mass. The preferable upper limit value of the content thereof with respect to a total amount of the composition of the embodiment is equal to or smaller than 20% by mass, equal to or smaller than 15% by mass, equal to or smaller than 13% by mass, equal to or smaller than 10% by mass, equal to or smaller than 8% by mass, equal to or smaller than 7% by mass, equal to or smaller than 6% by mass, equal to or smaller than 5% by mass, or equal to or smaller than 3% by mass.

The compound represented by general formula (L-1) is preferably a compound selected from the compound group represented by general formula (L-1-2).

[Chem. 60]

(L-1-2)

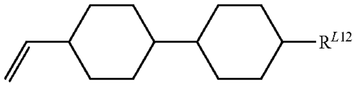

In the formula, $R^{L12}$ represents the same meaning as the meaning in general formula (L-1).

The preferable lower limit value of the content of the compound represented by formula (L-1-2) with respect to a total amount of the composition of the embodiment is equal to or greater than 1% by mass, equal to or greater than 5% by mass, equal to or greater than 10% by mass, equal to or greater than 15% by mass, equal to or greater than 17% by mass, equal to or greater than 20% by mass, equal to or greater than 23% by mass, equal to or greater than 25% by mass, equal to or greater than 27% by mass, equal to or greater than 30% by mass, or equal to or greater than 35% by mass. The preferable upper limit value of the content thereof with respect to a total amount of the composition of the embodiment is equal to or smaller than 60% by mass, equal to or smaller than 55% by mass, equal to or smaller than 50% by mass, equal to or smaller than 45% by mass, equal to or smaller than 42% by mass, equal to or smaller than 40% by mass, equal to or smaller than 38% by mass, equal to or smaller than 35% by mass, equal to or smaller than 33% by mass, or equal to or smaller than 30% by mass.

The compound represented by general formula (L-1-2) is preferably a compound selected from the compound group represented by formula (L-1-2.1) to formula (L-1-2.4), and preferably a compound represented by formula (L-1-2.2) to formula (L-1-2.4). Particularly, the compound represented by formula (L-1-2.2) is preferable, in order to particularly improve the response speed of the composition of the embodiment. In addition, in a case of obtaining Tni higher than the response speed, the compound represented by formula (L-1-2.3) or formula (L-1-2.4) is preferably used. The content of the compound represented by formula (L-1-2.3) and formula (L-1-2.4) set to be equal to or greater than 30% by mass is not preferable, in order to improve solubility at a low temperature.

[Chem. 61]

(L-1-2.1)

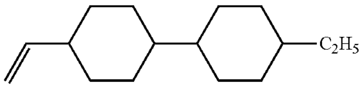

(L-1-2.2)

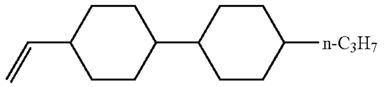

(L-1-2.3)

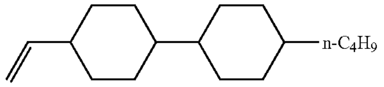

(L-1-2.4)

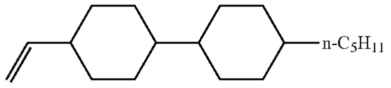

The preferable lower limit value of the content of the compound represented by formula (L-1-2.2) with respect to a total amount of the composition of the embodiment is equal to or greater than 10% by mass, equal to or greater than 15% by mass, equal to or greater than 18% by mass, equal to or greater than 20% by mass, equal to or greater than 23% by mass, equal to or greater than 25% by mass, equal to or greater than 27% by mass, equal to or greater than 30% by mass, equal to or greater than 33% by mass, equal to or greater than 35% by mass, equal to or greater than 38% by mass, or equal to or greater than 40% by mass. The preferable upper limit value of the content thereof with respect to a total amount of the composition of the embodiment is equal to or smaller than 60% by mass, equal to or smaller than 55% by mass, equal to or smaller than 50% by mass, equal to or smaller than 45% by mass, equal to or smaller than 43% by mass, equal to or smaller than 40% by mass, equal to or smaller than 38% by mass, equal to or smaller than 35% by mass, equal to or smaller than 32% by mass, equal to or smaller than 30% by mass, equal to or smaller than 27% by mass, equal to or smaller than 25% by mass, or equal to or smaller than 22% by mass.

The preferable lower limit value of the content of a total of the compound represented by formula (L-1-1.3) and the compound represented by formula (L-1-2.2) with respect to a total amount of the composition of the embodiment is equal to or greater than 10% by mass, equal to or greater than 15% by mass, equal to or greater than 20% by mass, equal to or greater than 25% by mass, equal to or greater than 27% by mass, equal to or greater than 30% by mass, equal to or greater than 35% by mass, or equal to or greater than 40% by mass. The preferable upper limit value of the content thereof with respect to a total amount of the composition of the embodiment is equal to or smaller than 60% by mass, equal to or smaller than 55% by mass, equal to or smaller than 50% by mass, equal to or smaller than 45% by mass, equal to or smaller than 43% by mass, equal to or smaller than 40% by mass, equal to or smaller than 38% by mass, equal to or smaller than 35% by mass, equal to or smaller than 32% by mass, equal to or smaller than 30% by mass, equal to or smaller than 27% by mass, equal to or smaller than 25% by mass, or equal to or smaller than 22% by mass.

The compound represented by general formula (L-1) is preferably a compound selected from the compound group represented by general formula (L-1-3).

[Chem. 62]

(L-1-3)

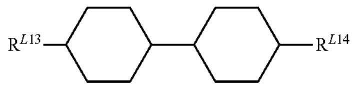

In the formula, $R^{L13}$ and $R^{L14}$ each independently represent an alkyl group having 1 to 8 carbon atoms or an alkoxy group having 1 to 8 carbon atoms.

$R^{L13}$ and $R^{L14}$ are preferably a linear alkyl group having 1 to 5 carbon atoms, a linear alkoxy group having 1 to 4 carbon atoms, and a linear alkenyl group having 2 to 5 carbon atoms.

The preferable lower limit value of the content of the compound represented by formula (L-1-3) with respect to a total amount of the composition of the embodiment is equal to or greater than 1% by mass, equal to or greater than 5% by mass, equal to or greater than 10% by mass, equal to or greater than 13% by mass, equal to or greater than 15% by mass, equal to or greater than 17% by mass, equal to or greater than 20% by mass, equal to or greater than 23% by mass, equal to or greater than 25% by mass, or equal to or greater than 30% by mass. The preferable upper limit value of the content thereof with respect to a total amount of the composition of the embodiment is equal to or smaller than 60% by mass, equal to or smaller than 55% by mass, equal to or smaller than 50% by mass, equal to or smaller than 45% by mass, equal to or smaller than 40% by mass, equal to or smaller than 37% by mass, equal to or smaller than 35% by mass, equal to or smaller than 33% by mass, equal to or smaller than 30% by mass, equal to or smaller than 27% by mass, equal to or smaller than 25% by mass, equal to or smaller than 23% by mass, equal to or smaller than 20% by mass, equal to or smaller than 17% by mass, equal to or smaller than 15% by mass, equal to or smaller than 13% by mass, or equal to or smaller than 10% by mass.

The compound represented by general formula (L-1-3) is preferably a compound selected from the compound group represented by formula (L-1-3.1) to formula (L-1-3.13), and preferably a compound represented by formula (L-1-3.1), formula (L-1-3.3), or formula (L-1-3.4). Particularly, the compound represented by formula (L-1-3.1) is preferable, in order to particularly improve the response speed of the composition of the embodiment. In addition, in a case of obtaining Tni higher than the response speed, the compound represented by formula (L-1-3.3), formula (L-1-3.4), formula (L-1-3.11), and formula (L-1-3.12) is preferably used. All of the content of the compound represented by formula (L-1-3.3), formula (L-1-3.4), formula (L-1-3.11), and formula (L-1-3.12) set to be equal to or greater than 20% is not preferable, in order to improve solubility at a low temperature.

[Chem. 63]

(L-1-3.1)

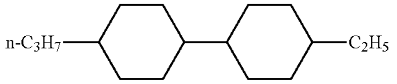

(L-1-3.2)

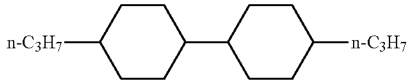

-continued (L-1-3.3)

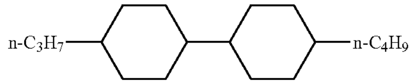

(L-1-3.4)

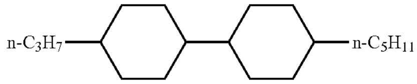

(L-1-3.11)

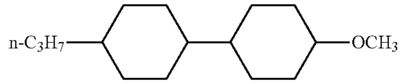

(L-1-3.12)

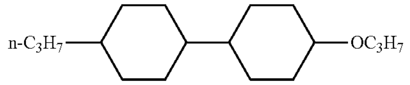

(L-1-3.13)

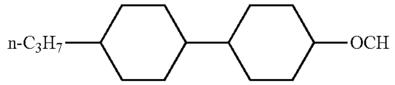

The preferable lower limit value of the content of the compound represented by formula (L-1-3.1) with respect to a total amount of the composition of the embodiment is equal to or greater than 1% by mass, equal to or greater than 2% by mass, equal to or greater than 3% by mass, equal to or greater than 5% by mass, equal to or greater than 7% by mass, equal to or greater than 10% by mass, equal to or greater than 13% by mass, equal to or greater than 15% by mass, equal to or greater than 18% by mass, or equal to or greater than 20% by mass. The preferable upper limit value of the content thereof with respect to a total amount of the composition of the embodiment is equal to or smaller than 20% by mass, equal to or smaller than 17% by mass, equal to or smaller than 15% by mass, equal to or smaller than 13% by mass, equal to or smaller than 10% by mass, equal to or smaller than 8% by mass, equal to or smaller than 7% by mass, or equal to or smaller than 6% by mass.

The compound represented by general formula (L-1) is preferably a compound selected from the compound group represented by general formula (L-1-4) and/or (L-1-5).

[Chem. 64]

(l-1-4)

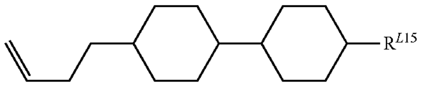

(l-1-5)

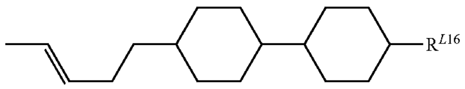

In the formula, $R^{L15}$ and $R^{L16}$ each independently represent an alkyl group having 1 to 8 carbon atoms or an alkoxy group having 1 to 8 carbon atoms.

$R^{L15}$ and $R^{L16}$ are preferably a linear alkyl group having 1 to 5 carbon atoms, a linear alkoxy group having 1 to 4 carbon atoms, and a linear alkenyl group having 2 to 5 carbon atoms.

The preferable lower limit value of the content of the compound represented by formula (L-1-4) with respect to a total amount of the composition of the embodiment is equal to or greater than 1% by mass, equal to or greater than 5% by mass, equal to or greater than 10% by mass, equal to or greater than 13% by mass, equal to or greater than 15% by mass, equal to or greater than 17% by mass, or equal to or greater than 20% by mass. The preferable upper limit value of the content thereof with respect to a total amount of the composition of the embodiment is equal to or smaller than 25% by mass, equal to or smaller than 23% by mass, equal to or smaller than 20% by mass, equal to or smaller than 17% by mass, equal to or smaller than 15% by mass, equal to or smaller than 13% by mass, or equal to or smaller than 10% by mass.

The preferable lower limit value of the content of the compound represented by formula (L-1-5) with respect to a total amount of the composition of the embodiment is equal to or greater than 1% by mass, equal to or greater than 5% by mass, equal to or greater than 10% by mass, equal to or greater than 13% by mass, equal to or greater than 15% by mass, equal to or greater than 17% by mass, or equal to or greater than 20% by mass. The preferable upper limit value of the content thereof with respect to a total amount of the composition of the embodiment is equal to or smaller than 25% by mass, equal to or smaller than 23% by mass, equal to or smaller than 20% by mass, equal to or smaller than 17% by mass, equal to or smaller than 15% by mass, equal to or smaller than 13% by mass, or equal to or smaller than 10% by mass.

The compound represented by general formulae (L-1-4) and (L-1-5) is preferably a compound selected from the compound group represented by formula (L-1-4.1) to formula (L-1-4.3) and formula (L-1-5.1) to formula (L-1-5.3), and preferably a compound represented by formula (L-1-4.2) or formula (L-1-5.2).

[Chem. 63]

(L-1-4.1)

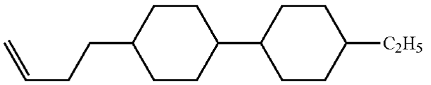

(L-1-4.2)

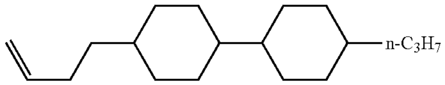

(L-1-4.3)

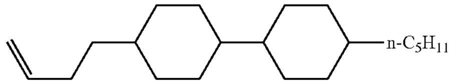

(L-1-5.1)

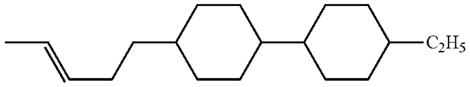

(L-1-5.2)

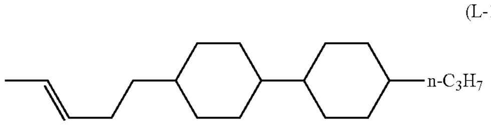

(L-1-5.3)

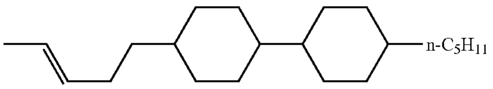

The preferable lower limit value of the content of the compound represented by formula (L-1-4.2) with respect to a total amount of the composition of the embodiment is equal to or greater than 1% by mass, equal to or greater than 2% by mass, equal to or greater than 3% by mass, equal to or greater than 5% by mass, equal to or greater than 7% by mass, equal to or greater than 10% by mass, equal to or greater than 13% by mass, equal to or greater than 15% by mass, equal to or greater than 18% by mass, or equal to or greater than 20% by mass. The preferable upper limit value of the content thereof with respect to a total amount of the composition of the embodiment is equal to or smaller than 20% by mass, equal to or smaller than 17% by mass, equal to or smaller than 15% by mass, equal to or smaller than 13% by mass, equal to or smaller than 10% by mass, equal to or smaller than 8% by mass, equal to or smaller than 7% by mass, or equal to or smaller than 6% by mass.

A combination of two or more kinds of compounds selected from the compounds represented by formula (L-1-1.3), formula (L-1-2.2), formula (L-1-3.1), formula (L-1-3.3), formula (L-1-3.4), formula (L-1-3.11), And formula (L-1-3.12) is preferable, and a combination of two or more kinds of compounds selected from the compounds represented by formula (L-1-1.3), formula (L-1-2.2), formula (L-1-3.1), formula (L-1-3.3), formula (L-1-3.4), formula (L-1-4.2). The preferable lower limit value of the content of a total content of these compounds with respect to a total amount of the composition of the embodiment is equal to or greater than 1% by mass, equal to or greater than 2% by mass, equal to or greater than 3% by mass, equal to or greater than 5% by mass, equal to or greater than 7% by mass, equal to or greater than 10% by mass, equal to or greater than 13% by mass, equal to or greater than 15% by mass, equal to or greater than 18% by mass, equal to or greater than 20% by mass, equal to or greater than 23% by mass, equal to or greater than 25% by mass, equal to or greater than 27% by mass, equal to or greater than 30% by mass, equal to or greater than 33% by mass, or equal to or greater than 35% by mass. The preferable upper limit value of the content thereof with respect to a total amount of the composition of the embodiment is equal to or smaller than 80% by mass, equal to or smaller than 70% by mass, equal to or smaller than 60% by mass, equal to or smaller than 50% by mass, equal to or smaller than 45% by mass, equal to or smaller than 40% by mass, equal to or smaller than 37% by mass, equal to or smaller than 35% by mass, equal to or smaller than 33% by mass, equal to or smaller than 30% by mass, equal to or smaller than 28% by mass, equal to or smaller than 25% by mass, equal to or smaller than 23% by mass, or equal to or smaller than 20% by mass.

In a case where the reliability is important, a combination of two or more kinds of compounds selected from the compounds represented by formula (L-1-3.1), formula (L-1-3.3), and formula (L-1-3.4) is preferable, and in a case where the response speed of the composition is important, a combination of two or more kinds of compounds selected from the compounds represented by formula (L-1-1.3) and formula (L-1-2.2) is preferable.

The compound represented by general formula (L-1) is preferably a compound selected from the compound group represented by general formula (L-1-6).

[Chem. 66]

(L-1-6)

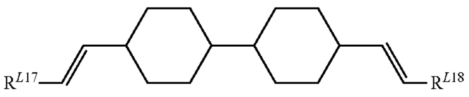

In the formula, $R^{L17}$ and $R^{L18}$ each independently represent a methyl group or a hydrogen atom.

The preferable lower limit value of the content of the compound represented by formula (L-1-6) with respect to a total amount of the composition of the embodiment is equal to or greater than 1% by mass, equal to or greater than 5% by mass, equal to or greater than 10% by mass, equal to or greater than 15% by mass, equal to or greater than 17% by mass, equal to or greater than 20% by mass, equal to or greater than 23% by mass, equal to or greater than 25% by mass, equal to or greater than 27% by mass, equal to or greater than 30% by mass, or equal to or greater than 35% by mass. The preferable upper limit value of the content thereof with respect to a total amount of the composition of the embodiment is equal to or smaller than 60% by mass, equal to or smaller than 55% by mass, equal to or smaller than 50% by mass, equal to or smaller than 45% by mass, equal to or smaller than 42% by mass, equal to or smaller than 40% by mass, equal to or smaller than 38% by mass, equal to or smaller than 35% by mass, equal to or smaller than 33% by mass, or equal to or smaller than 30% by mass.

The compound represented by general formula (L-1-6) is preferably a compound selected from the compound group represented by formula (L-1-6.1) to formula (L-1-6.3).

[Chem. 67]

(L-1-6.1)

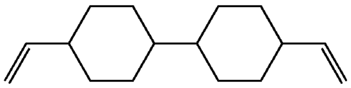

(L-1-6.2)

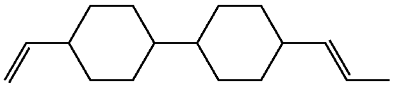

(L-1-6.3)

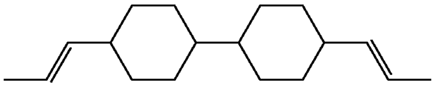

The compound represented by general formula (L-2) is the following compound.

[Chem. 68]

(L-2)

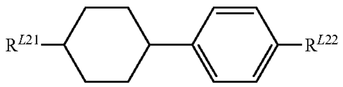

In the formula, $R^{L21}$ and $R^{L22}$ each independently represent the same meaning as $R^{L1}$ and $R^{L2}$ in general formula (L).

$R^{L21}$ is preferably an alkyl group having 1 to 5 carbon atoms or an alkenyl group having 2 to 5 carbon atoms, and $R^{L22}$ is preferably an alkyl group having 1 to 5 carbon atoms, an alkenyl group having 4 or 5 carbon atoms, or an alkoxy group having 1 to 4 carbon atoms.

The compound represented by general formula (L-1) can be used alone, and two or more compounds can also be used in combination. The kind of the compound which can be used in combination is not particularly limited, and compounds are suitably used in combination, in accordance with required performance such as solubility at a low temperature, a transition temperature, electrical reliability, or a birefringence. The number of kind of the compound used is one, two, three, four, or five or more, in one embodiment, for example.

In a case where the solubility at a low temperature is important, the effect is high by setting the content to be great, and in contrast, in a case where the response speed is important, the effect is high by setting the content to be low. In a case of improving dropping marks or burning properties, the range of the content is preferably set to be moderate.

The preferable lower limit value of the content of the compound represented by formula (L-2) with respect to a total amount of the composition of the embodiment is equal to or greater than 1% by mass, equal to or greater than 2% by mass, equal to or greater than 3% by mass, equal to or greater than 5% by mass, equal to or greater than 7% by mass, or equal to or greater than 10% by mass. The preferable upper limit value of the content thereof with respect to a total amount of the composition of the embodiment is equal to or smaller than 20% by mass, equal to or smaller than 15% by mass, equal to or smaller than 13% by mass, equal to or smaller than 10% by mass, equal to or smaller than 8% by mass, equal to or smaller than 7% by mass, equal to or smaller than 6% by mass, equal to or smaller than 5% by mass, or equal to or smaller than 3% by mass.

The compound represented by general formula (L-2) is preferably a compound selected from the compound group represented by formula (L-2.1) to formula (L-2.6), and preferably a compound represented by formula (L-2.1), formula (L-2.3), formula (L-2.4), and formula (L-2.6).

[Chem. 69]

(L-2.1)

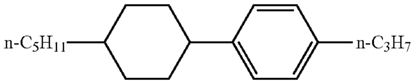

(L-2.2)

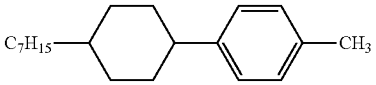

(L-2.3)

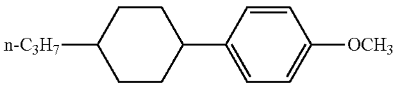

(L-2.4)

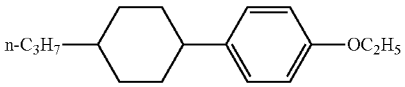

(L-2.5)

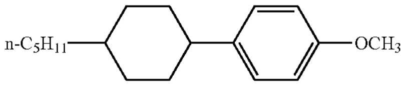

(L-2.6)

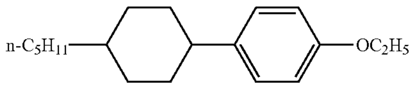

The compound represented by general formula (L-3) is the following compound.

[Chem. 70]

(L-3)

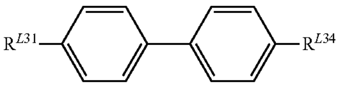

In the formula, $R^{L31}$ and $R^{L32}$ each independently represent the same meaning as $R^{L1}$ and $R^{L2}$ in general formula (L).

$R^{L31}$ and $R^{L32}$ are each independently preferably an alkyl group having 1 to 5 carbon atoms, an alkenyl group having 4 or 5 carbon atoms, or an alkoxy group having 1 to 4 carbon atoms.

The compound represented by general formula (L-3) can be used alone, and two or more compounds can also be used in combination. The kind of the compound which can be used in combination is not particularly limited, and compounds are suitably used in combination, in accordance with required performance such as solubility at a low temperature, a transition temperature, electrical reliability, or a birefringence. The number of kind of the compound used is one, two, three, four, or five or more, in one embodiment, for example.

The preferable lower limit value of the content of the compound represented by formula (L-3) with respect to a total amount of the composition of the embodiment is equal to or greater than 1% by mass, equal to or greater than 2% by mass, equal to or greater than 3% by mass, equal to or greater than 5% by mass, equal to or greater than 7% by mass, or equal to or greater than 10% by mass. The preferable upper limit value of the content thereof with respect to a total amount of the composition of the embodiment is equal to or smaller than 20% by mass, equal to or smaller than 15% by mass, equal to or smaller than 13% by mass, equal to or smaller than 10% by mass, equal to or smaller than 8% by mass, equal to or smaller than 7% by mass, equal to or smaller than 6% by mass, equal to or smaller than 5% by mass, or equal to or smaller than 3% by mass.

In a case of obtaining a high birefringence, the effect is high by setting the content to be great, and in contrast, in a case where a high Tni is important, the effect is high by setting the content to be low. In a case of improving dropping marks or burning properties, the range of the content is preferably set to be moderate.

The compound represented by general formula (L-3) is preferably a compound selected from the compound group represented by formula (L-3.1) to formula (L-3.7), and preferably a compound represented by formula (L-3.2) to formula (L-3.7).

[Chem. 71]

(L-3.1)

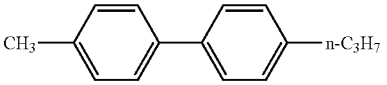

(L-3.2)

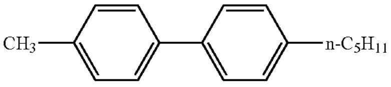

(L-3.3)

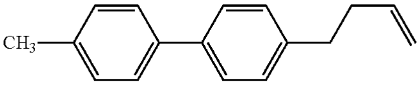

-continued (L-3.4)

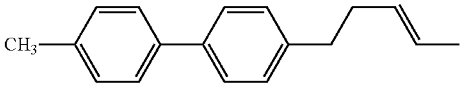

(L-3.6)

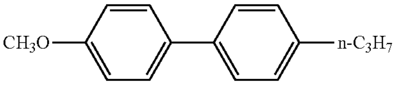

(L-3.7)

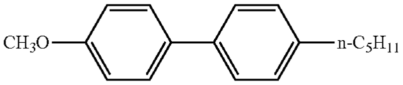

The compound represented by general formula (L-4) is the following compound.

[Chem. 72]

(L-4)

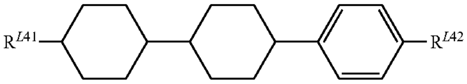

In the formula, $R^{L41}$ and $R^{L42}$ each independently represent the same meaning as $R^{L1}$ and $R^{L2}$ in general formula (L).

$R^{L41}$ is preferably an alkyl group having 1 to 5 carbon atoms or an alkenyl group having 2 to 5 carbon atoms, and $R^{L42}$ is preferably an alkyl group having 1 to 5 carbon atoms, an alkenyl group having 4 or 5 carbon atoms, or an alkoxy group having 1 to 4 carbon atoms.

The compound represented by general formula (L-4) can be used alone, and two or more compounds can also be used in combination. The kind of the compound which can be used in combination is not particularly limited, and compounds are suitably used in combination, in accordance with required performance such as solubility at a low temperature, a transition temperature, electrical reliability, or a birefringence. The number of kind of the compound used is one, two, three, four, or five or more, in one embodiment, for example.

In the composition of the embodiment, it is necessary that the content of the compound represented by general formula (L-4) is suitably adjusted in accordance with required performance such as solubility at a low temperature, a transition temperature, electrical reliability, a birefringence, process suitability, dropping marks, burning, or dielectric anisotropy.

The preferable lower limit value of the content of the compound represented by formula (L-4) with respect to a total amount of the composition of the embodiment is equal to or greater than 1% by mass, equal to or greater than 2% by mass, equal to or greater than 3% by mass, equal to or greater than 5% by mass, equal to or greater than 7% by mass, equal to or greater than 10% by mass, equal to or greater than 14% by mass, equal to or greater than 16% by mass, equal to or greater than 20% by mass, equal to or greater than 23% by mass, equal to or greater than 26% by mass, equal to or greater than 30% by mass, equal to or greater than 35% by mass, or equal to or greater than 40% by mass. The preferable upper limit value of the content of the compound represented by formula (L-4) with respect to a total amount of the composition of the embodiment is equal to or smaller than 50% by mass, equal to or smaller than 40% by mass, equal to or smaller than 35% by mass, equal to or smaller than 30% by mass, equal to or smaller than 20% by mass, equal to or smaller than 15% by mass, equal to or smaller than 10% by mass, or equal to or smaller than 5% by mass.

The compound represented by general formula (L-4) is preferably, for example, a compound represented by formula (L-4.1) to formula (L-4.3).

[Chem. 73]

(L-4.1)

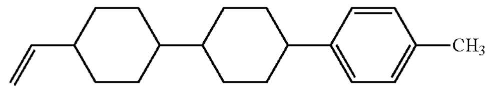

(L-4.2)

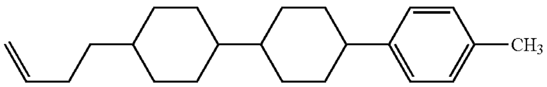

(L-4.3)

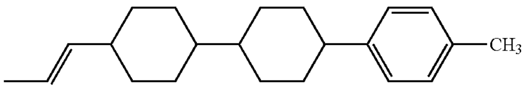

In accordance with required performance such as solubility at a low temperature, a transition temperature, electrical reliability, or a birefringence, a compound represented by formula (L-4.1) may be included, a compound represented by formula (L-4.2) may be included, both of a compound represented by formula (L-4.1) and a compound represented by formula (L-4.2) may be included, or all of compounds represented by formula (L-4.1) to formula (L-4.3) may be included.

The preferable lower limit value of the content of the compound represented by formula (L-4.1) or formula (L-4.2) with respect to a total amount of the composition of the embodiment is equal to or greater than 3% by mass, equal to or greater than 5% by mass, equal to or greater than 7% by mass, equal to or greater than 9% by mass, equal to or greater than 11% by mass, equal to or greater than 12% by mass, equal to or greater than 13% by mass, equal to or greater than 18% by mass, or equal to or greater than 21% by mass. The preferable upper limit value of the content thereof is equal to or smaller than 45% by mass, equal to or smaller than 40% by mass, equal to or smaller than 35% by mass, equal to or smaller than 30% by mass, equal to or smaller than 25% by mass, equal to or smaller than 23% by mass, equal to or smaller than 20% by mass, equal to or smaller than 18% by mass, equal to or smaller than 15% by mass, equal to or smaller than 13% by mass, equal to or smaller than 10% by mass, or equal to or smaller than 8% by mass.

In a case where both of a compound represented by formula (L-4.1) and a compound represented by formula (L-4.2) are included, the preferable lower limit value of the content of both compounds with respect to a total amount of the composition of the embodiment is equal to or greater than 15% by mass, equal to or greater than 19% by mass, equal to or greater than 24% by mass, or equal to or greater than 30% by mass. The preferable upper limit value of the content thereof is equal to or smaller than 45% by mass, equal to or smaller than 40% by mass, equal to or smaller than 35% by mass, equal to or smaller than 30% by mass, equal to or smaller than 25% by mass, equal to or smaller than 23% by mass, equal to or smaller than 20% by mass, equal to or smaller than 18% by mass, equal to or smaller than 15% by mass, or equal to or smaller than 13% by mass.

The compound represented by general formula (L-4) is preferably, for example, a compound represented by formula (L-4.4) to formula (L-4.6), and preferably a compound represented by formula (L-4.4).

[Chem. 74]

(L-4.4)

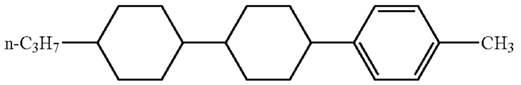

(L-4.5)

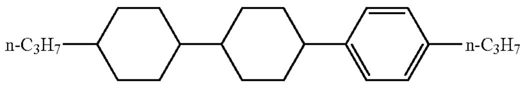

(L-4.6)

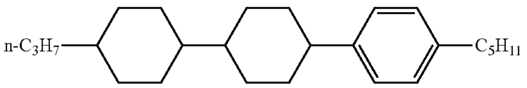

In accordance with required performance such as solubility at a low temperature, a transition temperature, electrical reliability, or a birefringence, a compound represented by formula (L-4.4) may be included, a compound represented by formula (L-4.5) may be included, or both of a compound represented by formula (L-4.4) and a compound represented by formula (L-4.5) may be included.

The preferable lower limit value of the content of the compound represented by formula (L-4.4) or formula (L-4.5) with respect to a total amount of the composition of the embodiment is equal to or greater than 3% by mass, equal to or greater than 5% by mass, equal to or greater than 7% by mass, equal to or greater than 9% by mass, equal to or greater than 11% by mass, equal to or greater than 12% by mass, equal to or greater than 13% by mass, equal to or greater than 18% by mass, or equal to or greater than 21% by mass. The preferable upper limit value of the content thereof is equal to or smaller than 45% by mass, equal to or smaller than 40% by mass, equal to or smaller than 35% by mass, equal to or smaller than 30% by mass, equal to or smaller than 25% by mass, equal to or smaller than 23% by mass, equal to or smaller than 20% by mass, equal to or smaller than 18% by mass, equal to or smaller than 15% by mass, equal to or smaller than 13% by mass, equal to or smaller than 10% by mass, or equal to or smaller than 8% by mass.

In a case where both of a compound represented by formula (L-4.4) and a compound represented by formula (L-4.5) are included, the preferable lower limit value of the content of both compounds with respect to a total amount of the composition of the embodiment is equal to or greater than 15% by mass, equal to or greater than 19% by mass, equal to or greater than 24% by mass, or equal to or greater than 30% by mass, and the preferable upper limit value thereof is equal to or smaller than 45% by mass, equal to or smaller than 40% by mass, equal to or smaller than 35% by mass, equal to or smaller than 30% by mass, equal to or smaller than 25% by mass, equal to or smaller than 23% by mass, equal to or smaller than 20% by mass, equal to or smaller than 18% by mass, equal to or smaller than 15% by mass, or equal to or smaller than 13% by mass.

The compound represented by general formula (L-4) is preferably a compound represented by formula (L-4.7) to formula (L-4.10), and particularly preferably a compound represented by formula (L-4.9).

[Chem. 75]

(L-4.7)

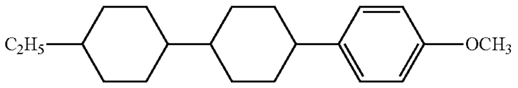

(L-4.8)

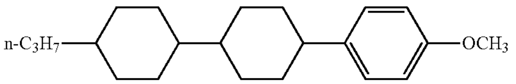

(L-4.9)

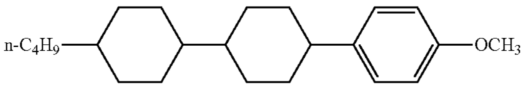

(L-4.10)

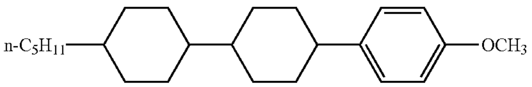

The compound represented by general formula (L-5) is the following compound.

[Chem. 76]

(L-5)

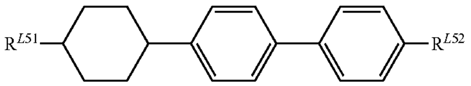

In the formula, $R^{L51}$ and $R^{L52}$ each independently represent the same meaning as $R^{L1}$ and $R^{L2}$ in general formula (L).

$R^{L51}$ is preferably an alkyl group having 1 to 5 carbon atoms or an alkenyl group having 2 to 5 carbon atoms, and $R^{L52}$ is preferably an alkyl group having 1 to 5 carbon atoms, an alkenyl group having 4 or 5 carbon atoms, or an alkoxy group having 1 to 4 carbon atoms.

The compound represented by general formula (L-5) can be used alone, and two or more compounds can also be used in combination. The kind of the compound which can be used in combination is not particularly limited, and compounds are suitably used in combination, in accordance with required performance such as solubility at a low temperature, a transition temperature, electrical reliability, or a birefringence. The number of kind of the compound used is one, two, three, four, or five or more, in one embodiment, for example.

In the composition of the embodiment, it is necessary that the content of the compound represented by general formula (L-5) is suitably adjusted in accordance with required performance such as solubility at a low temperature, a transition temperature, electrical reliability, a birefringence, process suitability, dropping marks, burning, or dielectric anisotropy.

The preferable lower limit value of the content of the compound represented by formula (L-5) with respect to a total amount of the composition of the embodiment is equal to or greater than 1% by mass, equal to or greater than 2% by mass, equal to or greater than 3% by mass, equal to or greater than 5% by mass, equal to or greater than 7% by mass, equal to or greater than 10% by mass, equal to or greater than 14% by mass, equal to or greater than 16% by mass, equal to or greater than 20% by mass, equal to or greater than 23% by mass, equal to or greater than 26% by mass, equal to or greater than 30% by mass, equal to or greater than 35% by mass, or equal to or greater than 40% by mass. The preferable upper limit value of the content of the compound represented by formula (L-5) with respect to a total amount of the composition of the embodiment is equal to or smaller than 50% by mass, equal to or smaller than 40% by mass, equal to or smaller than 35% by mass, equal to or smaller than 30% by mass, equal to or smaller than 20% by mass, equal to or smaller than 15% by mass, equal to or smaller than 10% by mass, or equal to or smaller than 5% by mass.

The compound represented by general formula (L-5) is preferably a compound represented by formula (L-5.1) or formula (L-5.2), and particularly preferably a compound represented by formula (L-5.1).

[Chem. 77]

(L-5.1)

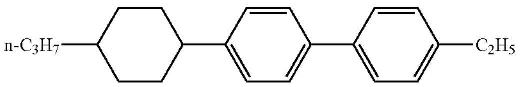

(L-5.2)

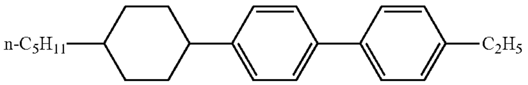

The preferable lower limit value of the content of these compounds with respect to a total amount of the composition of the embodiment is equal to or greater than 1% by mass, equal to or greater than 2% by mass, equal to or greater than 3% by mass, equal to or greater than 5% by mass, or equal to or greater than 7% by mass. The preferable upper limit value of the content of these compounds is equal to or smaller than 20% by mass, equal to or smaller than 15% by mass, equal to or smaller than 13% by mass, equal to or smaller than 10% by mass, or equal to or smaller than 9% by mass.

The compound represented by general formula (L-5) is preferably a compound selected from the compound group represented by formula (L-5.3) or formula (L-5.4).

[Chem. 78]

(L-5.3)

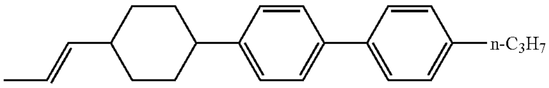

(L-5.4)

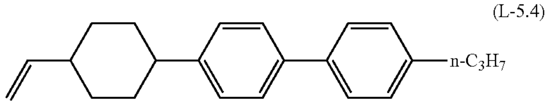

The preferable lower limit value of the content of these compounds with respect to a total amount of the composition of the embodiment is equal to or greater than 1% by mass, equal to or greater than 2% by mass, equal to or greater than 3% by mass, equal to or greater than 5% by mass, or equal to or greater than 7% by mass. The preferable upper limit value of the content of these compounds is equal to or smaller than 20% by mass, equal to or smaller than 15% by mass, equal to or smaller than 13% by mass, equal to or smaller than 10% by mass, or equal to or smaller than 9% by mass.

The compound represented by general formula (L-5) is preferably a compound selected from the compound group represented by formula (L-5.5) to formula (L-5.7), and particularly preferably a compound represented by formula (L-5.7).

[Chem. 79]

(L-5.5)

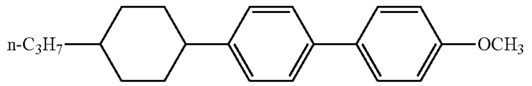

(L-5.6)

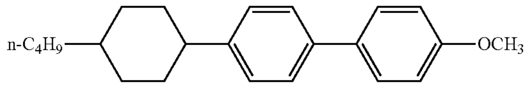

(L-5.7)

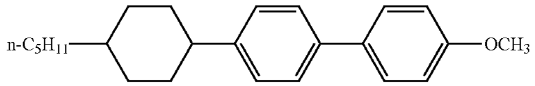

The preferable lower limit value of the content of these compounds with respect to a total amount of the composition of the embodiment is equal to or greater than 1% by mass, equal to or greater than 2% by mass, equal to or greater than 3% by mass, equal to or greater than 5% by mass, or equal to or greater than 7% by mass. The preferable upper limit value of the content of these compounds is equal to or smaller than 20% by mass, equal to or smaller than 15% by mass, equal to or smaller than 13% by mass, equal to or smaller than 10% by mass, or equal to or smaller than 9% by mass.

The compound represented by general formula (L-6) is the following compound.

[Chem. 80]

(L-6)

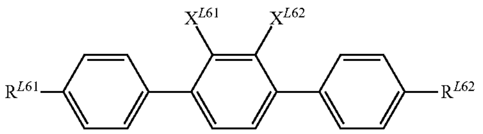

In the formula, $R^{L61}$ and $R^{L62}$ each independently represent the same meaning as $R^{L1}$ and $R^{L2}$ in general formula (L), and $R^{L61}$ and $R^{L62}$ each independently represent a hydrogen atom or a fluorine atom.

$R^{L61}$ and $R^{L62}$ are each independently an alkyl group having 1 to 5 carbon atoms or an alkenyl group having 2 to 5 carbon atoms, and one of $X^{L61}$ and $X^{L62}$ is a fluorine atom, and the other one is preferably a hydrogen atom.

The compound represented by general formula (L-6) can be used alone, and two or more compounds can also be used in combination. The kind of the compound which can be used in combination is not particularly limited, and compounds are suitably used in combination, in accordance with required performance such as solubility at a low temperature, a transition temperature, electrical reliability, or a birefringence. The number of kind of the compound used is one, two, three, four, or five or more, in one embodiment, for example.

The preferable lower limit value of the content of the compound represented by formula (L-6) with respect to a total amount of the composition of the embodiment is equal to or greater than 1% by mass, equal to or greater than 2% by mass, equal to or greater than 3% by mass, equal to or greater than 5% by mass, equal to or greater than 7% by mass, equal to or greater than 10% by mass, equal to or greater than 14% by mass, equal to or greater than 16% by mass, equal to or greater than 20% by mass, equal to or greater than 23% by mass, equal to or greater than 26% by mass, equal to or greater than 30% by mass, equal to or greater than 35% by mass, or equal to or greater than 40% by mass. The preferable upper limit value of the content of the compound represented by formula (L-6) with respect to a total amount of the composition of the embodiment is equal to or smaller than 50% by mass, equal to or smaller than 40% by mass, equal to or smaller than 35% by mass, equal to or smaller than 30% by mass, equal to or smaller than 20% by mass, equal to or smaller than 15% by mass, equal to or smaller than 10% by mass, or equal to or smaller than 5% by mass. In a case where an increase in Δn is important, it is preferable to increase the content thereof, and in a case where precipitation at a low temperature is important, it is preferable to decrease the content thereof.

The compound represented by general formula (L-6) is preferably a compound represented by formula (L-6.1) to formula (L-6.9).

[Chem. 81]

(L-6.1)

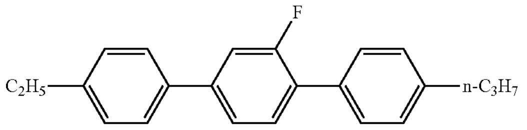

(L-6.2)

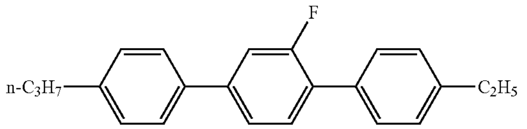

(L-6.3)

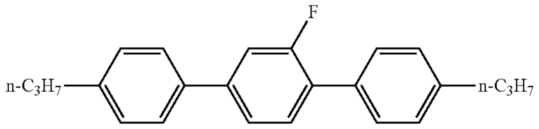

(L-6.4)

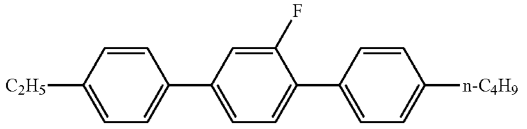

-continued (L-6.5)

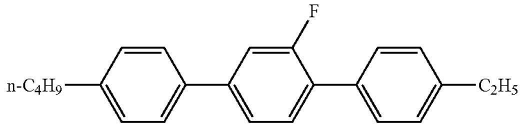

(L-6.6)

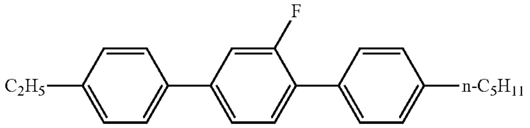

(L-6.7)

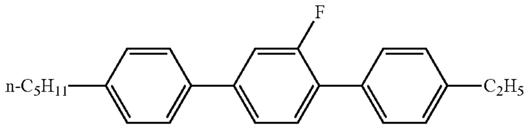

(L-6.8)

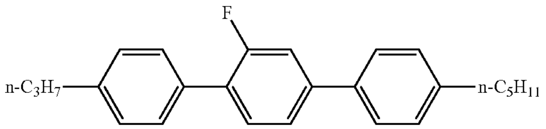

(L-6.9)

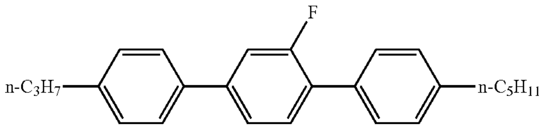

The kind of the compound which can be used in combination is not particularly limited. One to three kinds of compounds are preferably included or one to four kinds of compounds are more preferably included from these compounds. A wide molecular weight distribution of the compound to be selected is also effective to the solubility, for example, one kind of compound is selected from the compound represented by formula (L-6.1) or (L-6.2), one kind of compound is selected from the compound represented by formula (L-6.4) or (L-6.5), one kind of compound is selected from the compound represented by formula (L-6.6) or (L-6.7), one kind of compound is selected from the compound represented by formula (L-6.8) or (L-6.9), and these are preferably suitably combined. Among these, the compounds represented by formula (L-6.1), formula (L-6.3), formula (L-6.4), formula (L-6.6), and formula (L-6.9) are preferably included.

The compound represented by general formula (L-6) is, for example, preferably a compound represented by formula (L-6.10) to formula (L-6.17), and is preferably a compound represented by formula (L-6.11) among those.

[Chem. 82]

(L-6.10)

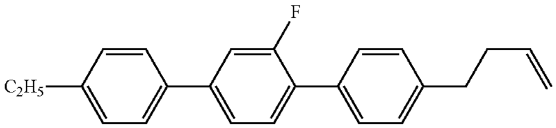

-continued (L-6.11)

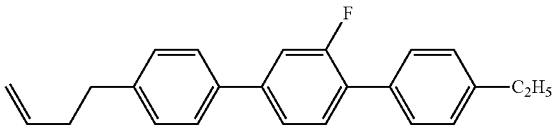

(L-6.12)

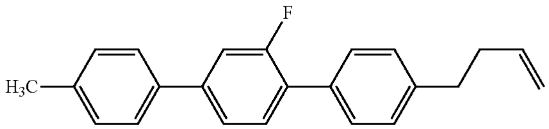

(L-6.13)

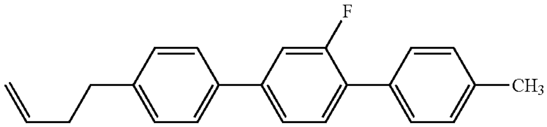

(L-6.14)

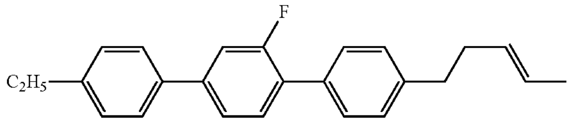

(L-6.15)

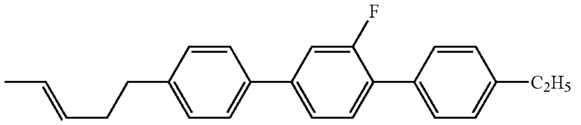

(L-6.16)

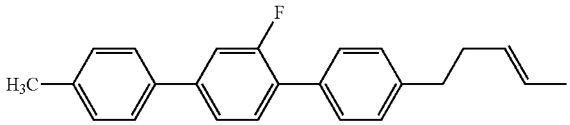

(L-6.17)

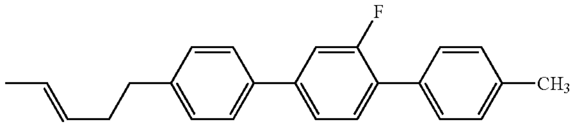

The preferable lower limit value of the content of these compounds with respect to a total amount of the composition of the embodiment is equal to or greater than 1% by mass, equal to or greater than 2% by mass, equal to or greater than 3% by mass, equal to or greater than 5% by mass, or equal to or greater than 7% by mass. The preferable upper limit value of the content of these compounds is equal to or smaller than 20% by mass, equal to or smaller than 15% by mass, equal to or smaller than 13% by mass, equal to or smaller than 10% by mass, or equal to or smaller than 9% by mass.

The compound represented by general formula (L-7) is the following compound.

[Chem. 83]

(L-7)

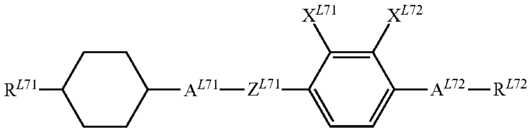

In the formula, $R^{L71}$ and $R^{L72}$ each independently represent the same meaning as $R^{L1}$ and $R^{L2}$ in general formula (L), $A^{L71}$ and $A^{L72}$ each independently represent the same meaning as $A^{L2}$ and $A^{L3}$ in general formula (L), hydrogen atoms on $A^{L71}$ and $A^{L72}$ each may be independently substituted with fluorine atoms, $Z^{L71}$ represents the same meaning as $Z^{L2}$ in general formula (L), and $X^{L71}$ and $X^{L72}$ each independently represent a fluorine atom or a hydrogen atom.

In the formula, $R^{L71}$ and $R^{L72}$ are each independently preferably an alkyl group having 1 to 5 carbon atoms, an alkenyl group having 2 to 5 carbon atoms, or an alkoxy group having 1 to 4 carbon atoms, $A^{L71}$ and $A^{L72}$ are each independently preferably a 1,4-cyclohexylene group or a 1,4-phenylene group, hydrogen atoms on $A^{L71}$ and $A^{L72}$ each may be independently substituted with fluorine atoms, $Z^{L71}$ is preferably a single bond or COO— and preferably a single bond, and $X^{L71}$ and $X^{L72}$ are preferably a hydrogen atom.

The kind of the compound which can be used in combination is not particularly limited, and compounds are combined, in accordance with required performance such as solubility at a low temperature, a transition temperature, electrical reliability, or a birefringence. The number of kind of the compound used is one, two, three, or four, in one embodiment, for example.

In the composition of the embodiment, it is necessary that the content of the compound represented by general formula (L-7) is suitably adjusted in accordance with required performance such as solubility at a low temperature, a transition temperature, electrical reliability, a birefringence, process suitability, dropping marks, burning, or dielectric anisotropy.

The preferable lower limit value of the content of the compound represented by formula (L-7) with respect to a total amount of the composition of the embodiment is equal to or greater than 1% by mass, equal to or greater than 2% by mass, equal to or greater than 3% by mass, equal to or greater than 5% by mass, equal to or greater than 7% by mass, equal to or greater than 10% by mass, equal to or greater than 14% by mass, equal to or greater than 16% by mass, or equal to or greater than 20% by mass. The preferable upper limit value of the content of the compound represented by formula (L-7) with respect to a total amount of the composition of the embodiment is equal to or smaller than 30% by mass, equal to or smaller than 25% by mass, equal to or smaller than 23% by mass, equal to or smaller than 20% by mass, equal to or smaller than 18% by mass, equal to or smaller than 15% by mass, equal to or smaller than 10% by mass, or equal to or smaller than 5% by mass.

In a case where the embodiment of the composition of the embodiment having a high Tni is desired, it is preferable to increase the content of the compound represented by formula (L-7), and in a case where the embodiment thereof having a low viscosity is desired, it is preferable to decrease the content thereof.

The compound represented by general formula (L-7) is preferably a compound represented by formula (L-7.1) to formula (L-7.4) and preferably a compound represented by formula (L-7.2).

[Chem. 84]

(L-7.1)

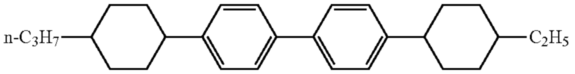

(L-7.2)

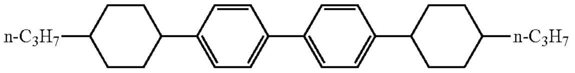

(L-7.3)

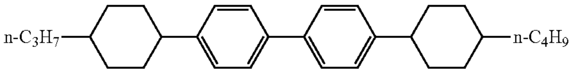

(L-7.4)

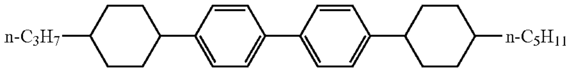

The compound represented by general formula (L-7) is preferably a compound represented by formula (L-7.11) to formula (L-7.13), and preferably a compound represented by formula (L-7.11).

[Chem. 85]

(L-7.11)

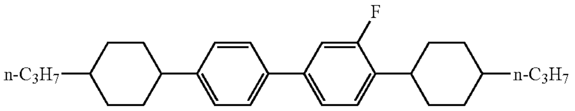

(L-7.12)

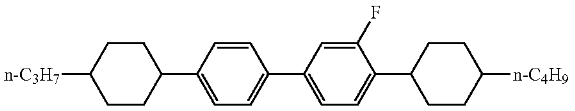

(L-7.13)

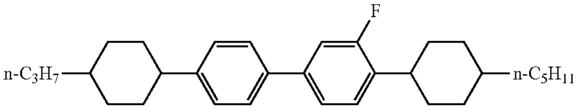

The compound represented by general formula (L-7) is a compound represented by formula (L-7.21) to formula (L-7.23). The compound is preferably a compound represented by formula (L-7.21).

[Chem. 86]

(L-7.21)

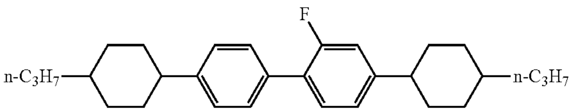

-continued (L-7.22)

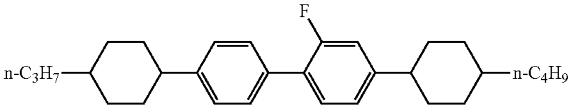

(L-7.23)

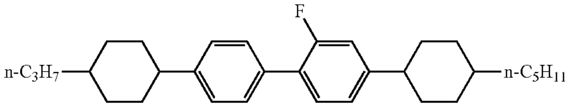

The compound represented by general formula (L-7) is preferably a compound represented by formula (L-7.31) to formula (L-7.34), and preferably a compound represented by formula (L-7.31) and/or formula (L-7.32).

[Chem. 87]

(L-7.31)

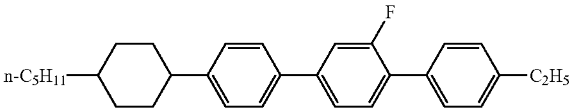

(L-7.32)

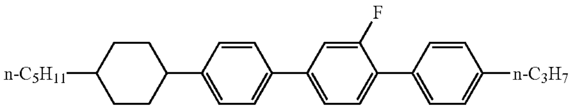

(L-7.33)

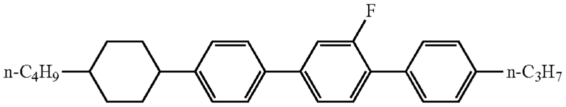

(L-7.34)

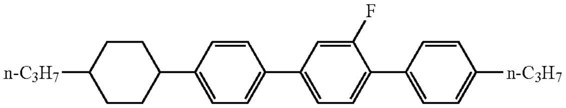

The compound represented by general formula (L-7) is preferably a compound represented by formula (L-7.41) to formula (L-7.44), and preferably a compound represented by formula (L-7.41) and/or formula (L-7.42).

[Chem. 88]

(L-7.41)

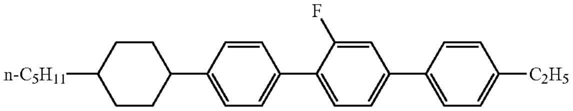

(L-7.42)

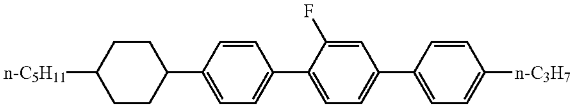

(L-7.43)

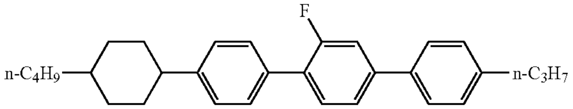

(L-7.44)

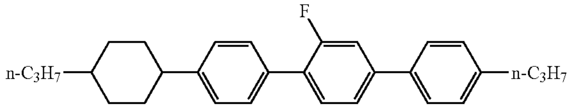

The compound represented by general formula (L-7) is preferably a compound represented by formula (L-7.51) to formula (L-7.53).

[Chem. 89]

(L-7.51)

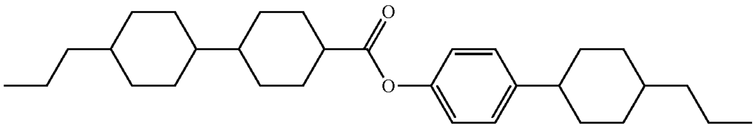

(L-7.52)

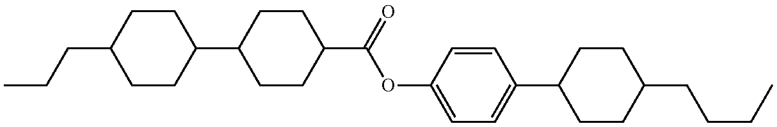

(L-7.53)

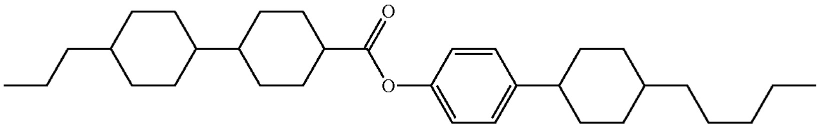

The liquid crystal composition further includes a polymerizable compound. The polymerizable compound may be a well-known polymerizable compound used for the liquid crystal composition. As an example of the polymerizable compound, a compound represented by general formula (P):

[Chem. 90]

(P)

$$(R^{P1}-Sp^{P1})_{mP1}(M^{P1})_{mP2}(L^{P1}-M^{P2})_{mP3}(L^{P2}-M^{P3})_{mP4}(Z^{P1})_{mP5}$$

is used.

In the formula (P), $Z^{P1}$ represents a fluorine atom, a cyano group, a hydrogen atom, an alkyl group having 1 to 15 carbon atoms, in which a hydrogen atom may be substituted with a halogen atom, an alkoxy group having 1 to 15 carbon atoms, in which a hydrogen atom may be substituted with a halogen atom, an alkenyl group having 1 to 15 carbon atoms, in which a hydrogen atom may be substituted with a halogen atom, an alkenyloxy group having 1 to 15 carbon atoms, in which a hydrogen atom may be substituted with a halogen atom, or $-SP^{P2}-R^{P2}$, $R^{P1}$ and $R^{P2}$ represent any of formula (R-I) to formula (R-IX):

[Chem. 91]

(R-I)

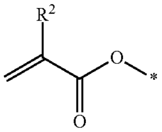

(R-II)

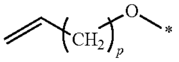

(R-III)

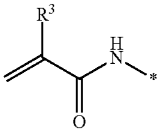

(R-IV)

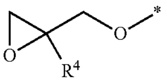

(R-V)

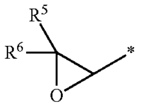

(R-VI)

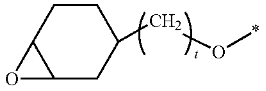

(R-VII)

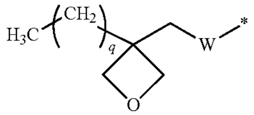

-continued (R-VIII)

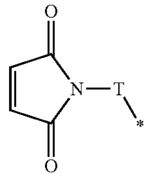

(R-IX)

HS—*

In the formulae, bonding to $Sp^{P1}$ is performed at *, $R^2$ to $R^6$ each independently represent a hydrogen atom, an alkyl group having 1 to 5 carbon atoms, or a halogenated alkyl group having 1 to 5 carbon atoms, W represents a single bond, —O—, or a methylene group, T represents a single bond or —COO—, p, t, and q each independently represent 0, 1, or 2), $Sp^{P1}$ and $Sp^{P2}$ represent a spacer group, $L^{P1}$ and $L^{P2}$ each independently represent a single bond, —O—, —S—, $—CH_2—$, $—OCH_2—$, $—CH_2O—$, —CO—, $—C_2H_4—$, —COO—, —OCO—, $—OCOOCH_2—$, $—CH_2OCOO—$, $—OCH_2CH_2O—$, $—CO—NR^a—$, $—NR^a—CO—$, $—SCH_2—$, $—CH_2S—$, $—CH{=}CR^a—COO—$, $—CH{=}CR^a—OCO—$, $—COO—CR^a{=}CH—$, $—OCO—CR^a{=}CH—$, $—COO—CR^a{=}CH—COO—$, $—COO—CR^a{=}CH—OCO—$, $—OCO—CR^a{=}CH—COO—$, $—OCO—CR^a{=}CH—OCO—$, $—(CH_2)_z—C({=}O)—O—$, $—(CH_2)_z—O—(C{=}O)—$, $—O—(C{=}O)—(CH_2)_z—$, $—(C{=}O)—O—(CH_2)_z—$, —CH═CH—, —CF═CF—, —CF═CH—, —CH═CF—, $—CF_2—$, $—CF_2O—$, $—OCF_2—$, $—CF_2CH_2—$, $—CH_2CF_2—$, $—CF_2CF_2—$, or —C≡C— (in the formulae, $R^a$'s each independently represent a hydrogen atom or an alkyl group having 1 to 4 carbon atoms, and z represents an integer of 1 to 4), $M^{P2}$ represents a 1,4-phenylene group, a 1,4-cyclohexylene group, anthracene-2,6-diyl group, a phenanthrene-2,7-diyl group, a pyridine-2,5-diyl group, a pyrimidine-2,5-diyl group, a naphthalene-2,6-diyl group, an indane-2,5-diyl group, a 1,2,3,4-tetrahydronaphthalene-2,6-diyl group, a 1,3-dioxane-2,5-diyl group, or a single bond, $M^{P2}$ may be unsubstituted or substituted with an alkyl group having 1 to 12 carbon atoms, a halogenated alkyl group having 1 to 12 carbon atoms, an alkoxy group having 1 to 12 carbon atoms, a halogenated alkoxy group having 1 to 12 carbon atoms, a halogen atom, a cyano group, a nitro group, or $—R^{P1}$, $M^{P1}$ represents any of the following formulae (i-11) to (ix-11):

[Chem. 92]

(i-11)

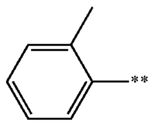

(ii-11)

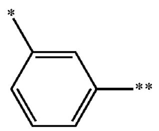

(iii-11)

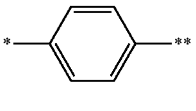

-continued (iv-11)

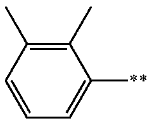

(v-11)

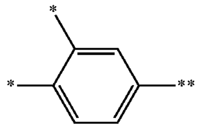

(vi-11)

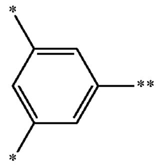

(vii-11)

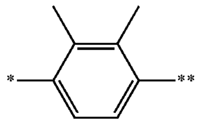

(viii-11)

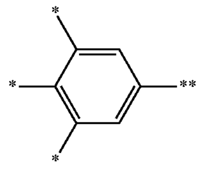

(ix-11)

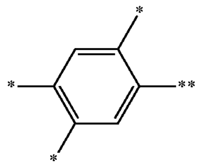

In the formulae, bonding to $SP^{P1}$ is performed at * and bonding to $L^{P1}$, $L^{P2}$, or $Z^{P1}$ is performed at **), any hydrogen atom on $M^{P1}$ may be substituted with an alkyl group having 1 to 12 carbon atoms, a halogenated alkyl group having 1 to 12 carbon atoms, an alkoxy group having 1 to 12 carbon atoms, a halogenated alkoxy group having 1 to 12 carbon atoms, a halogen atom, a cyano group, a nitro group, or —$R^{P1}$, $M^{P3}$ represents any of formulae (i-13) to (ix-13):

[Chem. 93]

(i-13)

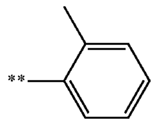

(ii-13)

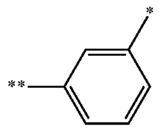

-continued (iii-13)

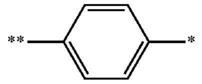

(iv-13)

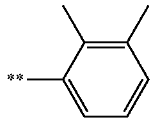

(v-13)

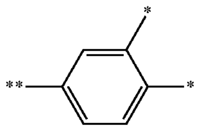

(vi-13)

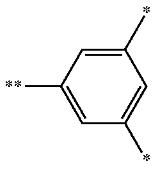

(vii-13)

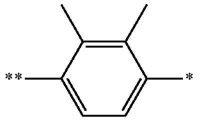

(viii-13)

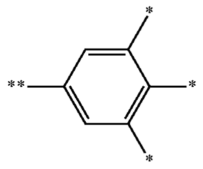

(ix-13)

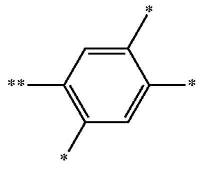

In the formulae, bonding to $Z^{P1}$ is performed at * and bonding to $L^{P2}$ is performed at **), any hydrogen atom on $M^{P3}$ may be substituted with an alkyl group having 1 to 12 carbon atoms, a halogenated alkyl group having 1 to 12 carbon atoms, an alkoxy group having 1 to 12 carbon atoms, a halogenated alkoxy group having 1 to 12 carbon atoms, a halogen atom, a cyano group, a nitro group, or —$R^{P1}$, $m^{P2}$ to $m^4$ each independently represent 0, 1, 2, or 3, $m^{P1}$ and $m^{P5}$ each independently represent 1, 2, or 3, when a plurality of $Z^{P1}$'s are present, these may be the same or different, when a plurality of $R^{P1}$'s are present, these may be the same or different, when a plurality of $R^{P2}$'s are present, these may be the same or different, when a plurality of $Sp^{P1}$'s are present, these may be the same or different, when a plurality of $Sp^{P2}$'s are present, these may be the same or different, when a plurality of $L^{P1}$'s are present, these may be the same or different, and when a plurality of $M^{P2}$'s are present, these may be the same or different.

In a case where the liquid crystal composition of the embodiment further includes the polymerizable compound, in addition to the compound (i), a pretilt angle of the liquid crystal molecule can be suitably formed.

It is preferable that the composition of the embodiment does not include a compound having a structure in which oxygen atoms are not bonded to each other, such as a peroxy acid (—CO—OO—) structure in a molecule.

In a case where the reliability and long-term stability of the composition are important, the content of the compound having a carbonyl group with respect to a total mass of the composition is preferably equal to or smaller than 5% by mass, more preferably equal to or smaller than 3% by mass, even more preferably equal to or smaller than 1% by mass, and most preferably substantially no compound is included.

In a case where stability due to UV irradiation is important, the content of the compound in which a chlorine atom is substituted, with respect to a total mass of the composition is preferably equal to or smaller than 15% by mass, preferably equal to or smaller than 10% by mass, preferably equal to or smaller than 8% by mass, preferably equal to or smaller than 5% by mass, preferably equal to or smaller than 3% by mass, and preferably substantially no compound is included.

An increase in content of the compound in which all ring structures in the molecule are 6-membered rings, is preferable, and the content of the compound in which all ring structures in the molecule are 6-membered rings, with respect to a total mass of the composition is preferably equal to or greater than 80% by mass, more preferably equal to or greater than 90% by mass, even more preferably equal to or greater than 95% by mass, and most preferably the composition is substantially configured with only the compound in which all ring structures in the molecule are 6-membered rings.

In order to prevent a deterioration due to oxidation of the composition, a decrease in content of the compound having a cyclohexenylene group as the ring structure is preferable, and the content of the compound having a cyclohexenylene group with respect to a total mass of the composition is preferably equal to or smaller than 10% by mass, preferably equal to or smaller than 8% by mass, preferably equal to or smaller than 5% by mass, preferably equal to or smaller than 3% by mass, and more preferably substantially no compound is included.

In a case where the improvement of viscosity and the improvement of Tni are important, a decrease in content of the compound having a 2-methylbenzene-1,4-diyl group, in which a hydrogen atom may be substituted with halogen, in a molecule is preferable, and the content of the compound having a 2-methylbenzene-1,4-diyl group in a molecule with respect to a total mass of the composition is preferably equal to or smaller than 10% by mass, preferably equal to or smaller than 8% by mass, preferably equal to or smaller than 5% by mass, preferably equal to or smaller than 3% by mass, and more preferably substantially no compound is included.

The expression that substantially no compound is included in the specification means that no compound is included excluding substances which are unintentionally included (inevitable impurities).

A lower limit value of an average elastic coefficient ($K_{AVG}$) of the liquid crystal composition is preferably equal to or greater than 10, preferably equal to or greater than 10.5, preferably equal to or greater than 11, preferably equal to or greater than 11.5, preferably equal to or greater than 12, preferably equal to or greater than 12.3, preferably equal to or greater than 12.5, preferably equal to or greater than 12.8, preferably equal to or greater than 13 preferably equal to or greater than 13.3, preferably equal to or greater than 13.5, preferably equal to or greater than 13.8, preferably equal to or greater than 14, preferably equal to or greater than 14.3, preferably equal to or greater than 14.5, preferably equal to or greater than 14.8, preferably equal to or greater than 15, preferably equal to or greater than 15.3, preferably equal to or greater than 15.5, preferably equal to or greater than 15.8, preferably equal to or greater than 16, preferably equal to or greater than 16.3, preferably equal to or greater than 16.5, preferably equal to or greater than 16.8, preferably equal to or greater than 17, preferably equal to or greater than 17.3, preferably equal to or greater than 17.5, preferably equal to or greater than 17.8, or preferably equal to or greater than 18. The upper limit value of the average elastic coefficient ($K_{AVG}$) of the liquid crystal composition is preferably equal to or smaller than 25, preferably equal to or smaller than 24.5, preferably equal to or smaller than 24, preferably equal to or smaller than 23.5, preferably equal to or smaller than 23, preferably equal to or smaller than 22.8, preferably equal to or smaller than 22.5, preferably equal to or smaller than 22.3, preferably equal to or smaller than 22, preferably equal to or smaller than 21.8, preferably equal to or smaller than 21.5, preferably equal to or smaller than 21.3, preferably equal to or smaller than 21, preferably equal to or smaller than 20.8, preferably equal to or smaller than 20.5, preferably equal to or smaller than 20.3, preferably equal to or smaller than 20, preferably equal to or smaller than 19.8, preferably equal to or smaller than 19.5, preferably equal to or smaller than 19.3, preferably equal to or smaller than 19, preferably equal to or smaller than 18.8, preferably equal to or smaller than 18.5, preferably equal to or smaller than 18.3, preferably equal to or smaller than 18, preferably equal to or smaller than 17.8, preferably equal to or smaller than 17.5, preferably equal to or smaller than 17.3, or preferably equal to or smaller than 17. In a case where power consumption reduction is important, it is effective to prevent a light intensity of a backlight, and it is preferable to improve transmittance of light of the liquid crystal display element. Accordingly, a value of $K_{AVG}$ is preferably set to be low. In a case where the improvement of response speed is important, the value of $K_{AVG}$ is preferably set to be high.

(Liquid Crystal Display Element)

The liquid crystal composition of the embodiment is applied to the liquid crystal display element. Hereinafter, an example of the liquid crystal display element according to the embodiment will be described suitably with reference to FIGS. 1 and 2.

FIG. 1 is a view schematically showing a configuration of a liquid crystal display element. In FIG. 1, for the convenience of description, the constituent elements are shown to be separated from each other. As shown in FIG. 1, a liquid crystal display element 1 according to the embodiment includes a first substrate 2 and a second substrate 3 disposed to face each other, a liquid crystal layer 4 provided between the first substrate 2 and the second substrate 3, and the liquid crystal layer 4 is configured of the liquid crystal composition of the embodiment described above.

A pixel electrode layer 5 is formed on a surface of the first substrate 2 on a side of the liquid crystal layer 4. A common electrode layer 6 is provided on the second substrate 3 on a side of the liquid crystal layer 4. The first substrate 2 and the second substrate 3 may be interposed between a pair of polarizing plates 7 and 8. A color filter 9 may be further provided on the second substrate 3 on a side of the liquid crystal layer 4.

That is, the liquid crystal display element 1 according to the embodiment has a configuration in which the first polarizing plate 7, the first substrate 2, the pixel electrode layer 5, the liquid crystal layer 4 including the liquid crystal composition, the common electrode layer 6, the color filter 9, the second substrate 3, and the second polarizing plate 8 are laminated in this order.

The first substrate 2 and the second substrate 3 are formed of, for example, a material having flexibility such as glass or plastic. At least one of the first substrate 2 and the second substrate 3 is formed of a transparent material, and the other one thereof may be formed of a transparent material or may be formed of an opaque material such as metal or silicon. The first substrate 2 and the second substrate 3 are bonded to each other with a sealing material such as an epoxy-based thermosetting composition disposed in a peripheral region, and in order to maintain a distance between the substrates, for example, a particulate spacer such as glass particles, plastic particles, or alumina particles, or a spacer column formed of a resin formed by a photolithographic method may be disposed therebetween.

Regarding the first polarizing plate 7 and the second polarizing plate 8, a polarizing axis of each polarizing plate can be adjusted to adjust a viewing angle or contrast to be excellent, and the polarizing plates preferably have transmission axes orthogonal to each other, so that the transmission axes are operated in a normally black mode. Particularly, any one of the first polarizing plate 7 and the second polarizing plate 8 is preferably disposed so as to have a transmission axis parallel to an alignment direction of liquid crystal molecules, in a case where no voltage is applied.

Regarding the color filter 9, from a viewpoint of preventing leakage of light, a black matrix is preferably formed, and a black matrix (not shown) is preferably formed on a portion corresponding to a thin film transistor.

The black matrix may be installed on a substrate on a side opposite to an array substrate with the color filter, may be installed on the array substrate side with the color filter, or the black matrix may be installed on the array substrate and the color filter may be provided the other substrate, separately. In addition, the black matrix may be installed separately from the color filter, and transmittance may be decreased by overlapping each color of the color filter.

Figure 2:
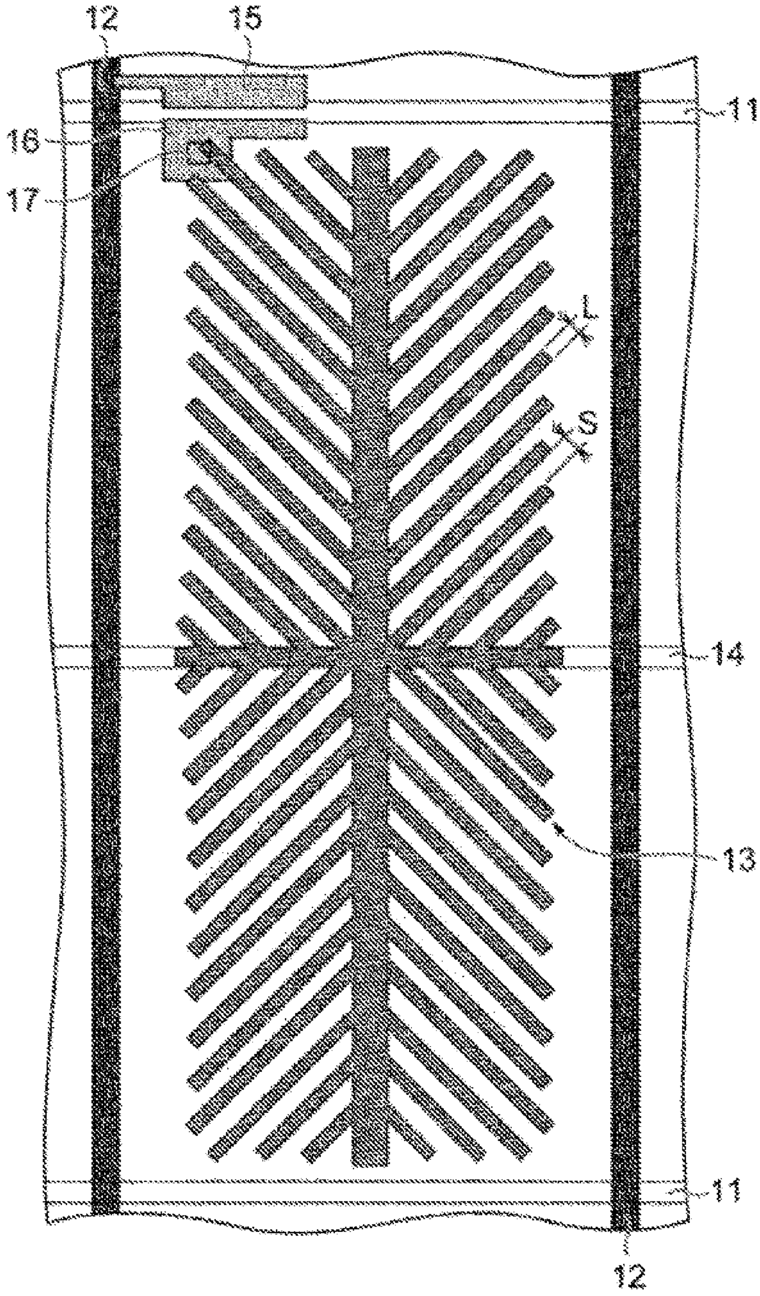
FIG. 2 is an enlarged plan view of a region surrounded with a line I of FIG. 1.

FIG. 2 is an enlarged plan view of a region surrounded with a line I which is a portion of the pixel electrode layer 5 formed on the first substrate 2 of FIG. 1. As shown in FIG. 2, in the pixel electrode layer 5 including a thin film transistor formed on the surface of the first substrate 2, a plurality of gate bus lines 11 for supplying a scanning signal and a plurality of data bus lines 12 for supplying a display signal are disposed in matrix so as to intersect each other. FIG. 2 only shows a pair of gate bus lines 11 and 11 and a pair of data bus lines 12 and 12.

A unit pixel of the liquid crystal display element is formed by the region surrounded by the plurality of gate bus lines 11 and the plurality of data bus lines 12, and a pixel electrode 13 is formed in the unit pixel. The pixel electrode 13 has a so-called fishbone structure including two stem portions orthogonal to each other to form a cross shape, and a plurality of branch portions extending from each stem portion. A Cs electrode 14 is provided substantially in parallel to the gate bus line 11 between the pair of the gate bus lines 11 and 11. In addition, a thin film transistor including a source electrode 15 and a drain electrode 16 is provided in the vicinity of an intersection where the gate bus line 11 and the data bus line 12 intersect each other. In the drain electrode 16, a contact hole 17 is provided.

Each of the gate bus line 11 and the data bus line 12 is preferably formed of a metal film, more preferably formed of Al, Cu, Au, Ag, Cr, Ta, Ti, Mo, W, Ni, or an alloy thereof, and even more preferably formed of Mo, Al, or an alloy thereof.

The pixel electrode 13 is preferably a transparent electrode, in order to improve transmittance. The transparent electrode is formed of an oxide semiconductor (ZnO, InGaZnO, SiGe, GaAs, IZO (Indium Zinc Oxide), ITO (Indium Tin Oxide), SnO, TiO, AZTO (AlZnSnO), or the like) by sputtering or the like. In this case, a film thickness of the transparent electrode may be 10 to 200 nm. In addition, in order to decrease electrical resistance, the transparent electrode can also be formed as a polycrystal ITO film, by firing an amorphous ITO film.

In the liquid crystal display element of the embodiment, for example, a wiring can be formed on the first substrate 2 and the second substrate 3 by sputtering a metal material such as Al or an alloy thereof, and the pixel electrode layer 5 and the common electrode layer 6 can be respectively formed. In addition, the color filter 9 can be formed, for example, by a pigment dispersion method, a printing method, an electrodeposition method, or a dyeing method. As an example of a forming method of the color filter by the pigment dispersion method, a curable colored composition for a color filter is applied on the transparent substrate, subjected to a patterning treatment, and cured by heating or light irradiation. By performing this step with respect to each of three colors of red, green, blue, a pixel portion for the color filter can be formed. In addition, the color filter 9 may be installed on a side of a substrate including a TFT or the like.

The first substrate 2 and the second substrate 3 face each other so that the pixel electrode layer 5 and the common electrode layer 6 respectively become the inner side thereof, and in this case, the interval between the first substrate 2 and the second substrate 3 may be adjusted through a spacer. In this case, a thickness of the liquid crystal layer 4 is preferably adjusted, for example, to be 1 to 100 μm.

In a case of using the polarizing plates 7 and 8, the sum of a refractive index anisotropy Δn of the liquid crystal layer 4 and the thickness of the liquid crystal layer 4 are preferably adjusted so that the contrast becomes the maximum. In addition, in a case where two polarizing plates 7 and 8 are present, the polarizing axis of each polarizing plate can be adjusted so as to adjust a viewing angle or contrast to be excellent. Further, a retardation film for increasing the viewing angle can also be used. After that, a sealing agent such as an epoxy-based thermosetting composition is screen-printed on the substrates, in a state where a liquid crystal injection port is provided, the substrates are bonded to each other and heated for heat curing of the sealing agent.

As the method for interposing the composition between the two substrates 2 and 3, a typical vacuum injection method or a one drop fill (ODF) method can be used. In the vacuum injection method, dropping marks are not generated, but marks of injection remain. In the embodiment, a display element manufactured by the ODF method can be suitably used. In the manufacturing step of the liquid crystal display element of the ODF method, a sealing agent such as an epoxy-based thermosetting composition is drawn on any one substrate of a back plane and a front plane in a closed loop back shape, a predetermined amount of the composition is added dropwise therein under deaeration, and the front plane and the back plane are bonded to each other, and accordingly, the liquid crystal display element can be manufactured. In the embodiment, the generation of dropping marks in a case where the liquid crystal composition is added dropwise on the substrate can be prevented in the ODF method. The dropping mark is defined as a phenomenon in which a white mark of the dropped liquid crystal composition is generated in a case of black display.

In the manufacturing step of the liquid crystal display element by the ODF method, it is necessary that the optimal liquid crystal injection amount is added dropwise in accordance with a size of the liquid crystal display element, but regarding the liquid crystal composition of the embodiment, the liquid crystal can be can be continuously stably added dropwise for a long period of time, without an effect with respect to rapid pressure change or impact in a dropping device occurring in a case of liquid crystal dropping, for example, and accordingly, it is also possible to maintain a high yield of the liquid crystal display element. Particularly, a small liquid crystal display element widely used for a smart phone which is the latest trend has a small degree of optimal liquid crystal injection amount, and accordingly, it is difficult to prevent a shift from the optimal value in a certain range. However, by using the liquid crystal composition of the embodiment, a stable discharge amount of a liquid crystal material can be realized even in the small liquid crystal display element.

In a case where the liquid crystal composition of the embodiment includes the polymerizable compound, as a method of polymerizing the polymerizable compound, a method of performing the polymerization by emitting an active energy ray such as an ultraviolet ray or an electron ray singly, in combination, or in order is preferable, because a suitable polymerization speed is desired for obtaining excellent alignment performance of the liquid crystal. In a case of using an ultraviolet ray, a polarizing light source may be used or a non-polarizing light source may be used. In a case of performing the polarization in a state where the polymerizable compound-containing composition is interposed between the two substrates, it is necessary that at least the substrate on the irradiated surface side applies suitable transparency to the active energy ray. A method of polymerizing only a specific portion using a mask in a case of the light irradiation, changing the alignment state of the non-polymerized portion by changing the conditions such as an electric field, a magnetic field, or a temperature, and further emitting the active energy ray for the polymerization may be used. Particularly, in a case of the ultraviolet light exposure, the ultraviolet light exposure is preferably performed while applying an AC electric field to the polymerizable compound-containing composition. Regarding the AC electric field to be applied, AC is preferable at a frequency of 10 Hz to 10 kHz and more preferable at a frequency of 60 Hz to 10 kHz, and a voltage is selected depending on a desired pretilt angle of the liquid crystal display element. That is, it is possible to control the pretilt angle of the liquid crystal display element by the voltage to be applied. In a horizontal field type MVA mode liquid crystal display element, the pretilt angle is preferably controlled to be 80 degrees to 89.9 degrees, from viewpoints of alignment stability and contrast.

A temperature of the irradiation is preferably in a temperature range in which the liquid crystal state of the composition of the embodiment is maintained. The polymerization is preferably performed at a temperature close to the room temperature, that is, typically a temperature of 15° C. to 35° C. As a lamp for generating the ultraviolet ray, a metal halide lamp, a high pressure mercury lamp, or a super high pressure mercury lamp can be used. In addition, regarding the wavelength of the ultraviolet ray to be emitted, the ultraviolet ray in a wavelength region which is not in an absorption wavelength region of the composition is preferably emitted, and the ultraviolet ray is preferably cut and used, if necessary. An intensity of the ultraviolet ray to be emitted is preferably 0.1 mW/cm$^2$ to 100 mW/cm$^2$, and more preferably 2 mW/cm$^2$ to 50 mW/cm$^2$. The energy amount of the ultraviolet ray to be emitted can be suitably adjusted, and is preferably 10 mJ/cm$^2$ to 500 J/cm$^2$, and more preferably 100 mJ/cm$^2$ to 200 J/cm$^2$. In a case of emitting the ultraviolet ray, the intensity may be changed. The time for emitting the ultraviolet ray is suitably selected in accordance with the intensity of the ultraviolet ray, and is preferably 10 seconds to 3, 600 seconds and more preferably 10 seconds to 600 seconds.

In the liquid crystal composition of the embodiment, the compound (i) does not inhibit the polymerization reaction of the polymerizable compound, and accordingly, the polymerizable compounds can be suitably polymerized and the generation of the unreacted polymerizable compound remaining in the liquid crystal composition can be prevented.

In a case where the compound (ii) is used as the polymerizable compound, the liquid crystal display element 1 to be obtained includes the two substrate 2 and 3, and the liquid crystal layer 4 including the liquid crystal composition provided between the two substrates 2 and 3 and the polymer of the compound represented by general formula (ii). In this case, the polymer of the compound represented by general formula (ii) is considered to be unevenly distributed on the sides of the substrates 2 and 3 in the liquid crystal layer 4.

The liquid crystal display element 1 may be a liquid crystal display element for active matrix driving. The liquid crystal display element 1 may be a PSA type, PSVA type, VA type, IPS type, FFS type, or ECB type liquid crystal display element, and is preferably a PSA type liquid crystal display element.

In the liquid crystal display element of the embodiment, the liquid crystal composition including the compound (i) is used, and accordingly, it is not necessary to provide an alignment film such as a polyimide alignment film on the liquid crystal layer 4 side of the first substrate 2 and the second substrate 3. That is, the liquid crystal display element of the embodiment can have a configuration in which at least one of the two substrates is not provided with any alignment film such as a polyimide alignment film.

EXAMPLES

Hereinafter, the invention is further described in detail with reference to examples, but the invention is not limited to the examples.

Example 1

50 g of 5-bromosalicylaldehyde, 75 g of (2,2-dimethyl ethyl-1,3-dioxane-5-yl) methyl mesylate, 35 g of potassium carbonate, and 500 ml of N, N-dimethylformamide were added to a reaction vessel including a stirring device, a cooling device, and a thermometer, and a reaction was carried out at 90° C. for 5 hours. After completing the reaction, the resultant material was cooled, 1 L of ethyl acetate was added, an organic layer was washed with water or a saturated saline solution, a solvent was distilled, and 67 g of a compound represented by (1) was obtained.

[Chem. 94]

(1)

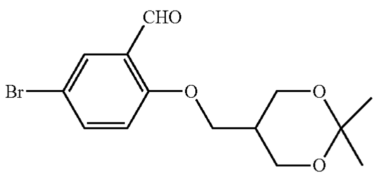

Next, 59 g of 4-(8-octyloxy)-3-fluorophenylboronic acid, 60 g of the compound (1), 42 g of potassium carbonate, 1.8 g of tetrakistriphenyl phosphine palladium, 200 mL of tetrahydrofuran, and 100 ml of water were added to a reaction vessel including a stirring device, a cooling device, and a thermometer, and a reaction was carried out at 70° C. for 5 hours. After completing the reaction, the resultant material was cooled, a 10% hydrochloric acid was added, and a target material was extracted by ethyl acetate. The organic layer was washed with water or a saturated saline solution, and the solvent was distilled. After that, dispersion washing with toluene and purification with an alumina column were performed, and 74 g of a compound represented by formula (2) was obtained.

[Chem. 95]

(2)

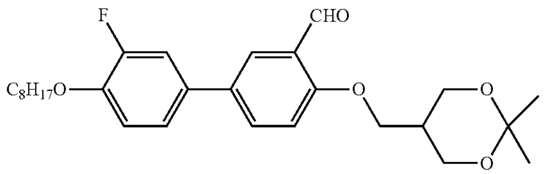

2 g of sodium borohydride and 20 ml of ethanol were added to a reaction vessel including a stirring device, a cooling device, and a thermometer, and the reaction vessel was cooled approximately at 10° C. After that, a THF solution (200 ml) of 47 g of the compound (2) was slowly added dropwise. After completing the reaction, a saturated aqueous ammonium chloride solution was slowly added, and washing was performed with 400 ml of ethyl acetate, water, or a saturated saline solution. By distilling the solvent and performing the purification with an alumina column, 42 g of a compound represented by (3) was obtained.

[Chem. 96]

(3)

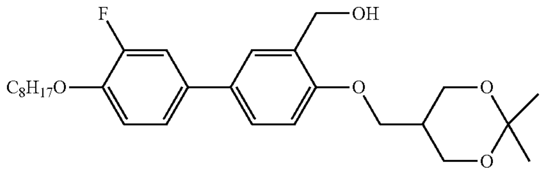

Next, 42 g of the compound (3), 12 g of triethylamine, and 300 ml of dichloromethane were added to a reaction vessel including a stirring device, a cooling device, and a thermometer, and the reaction vessel was cooled to 10° C. or lower. After that, 12 g of methacryloyl chloride was slowly added dropwise. After completing the dropwise addition, the temperature of the reaction vessel was returned to room temperature, and the reaction was carried out for 3 hours. After completing the reaction, water was slowly added, and washing was carried out with 400 ml of dichloromethane, water, or a saturated saline solution. By distilling the solvent and performing the purification with an alumina column, 38 g of a compound represented by (4) was obtained.

[Chem. 97]

(4)

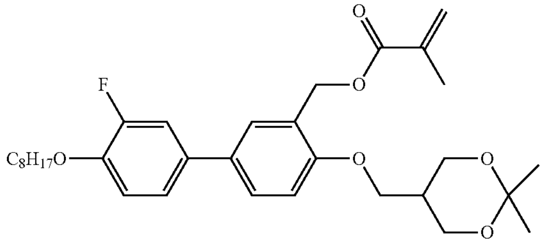

After that, the compound (4) and 100 ml of THF were added to a reaction vessel including a stirring device and a thermometer, and 20 ml of a 10% hydrochloric acid was slowly added dropwise. After completing the reaction, the resultant material was cooled and a target material was extracted by ethyl acetate. The organic layer was washed with water or a saturated saline solution, and the solvent was distilled. After that, dispersion washing with toluene and purification with an alumina column were performed, and 31 g of a compound represented by formula (5) was obtained.

[Chem. 98]

(5)

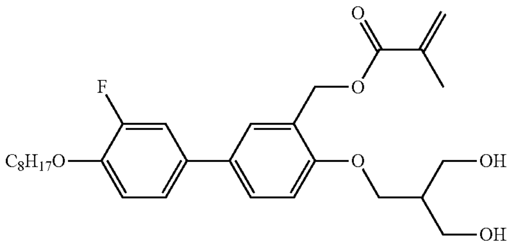

31 g of the compound (5) and 400 ml of dichloromethane were added to a reaction vessel including a stirring device and a thermometer, and the reaction vessel was cooled to 10° C. or lower. Next, 14 g of ethyl chloroformate was slowly added dropwise. After completing the dropwise addition, the resultant material was stirred for 30 minutes. Then, 18 g of triethylamine was added dropwise. After completing the reaction, the organic layer was washed with water or a saturated saline solution, and the solvent was distilled. Then, the purification with a silica column was performed, 26 g of a target compound represented by a compound (6) was obtained.

[Chem. 99]

(6)

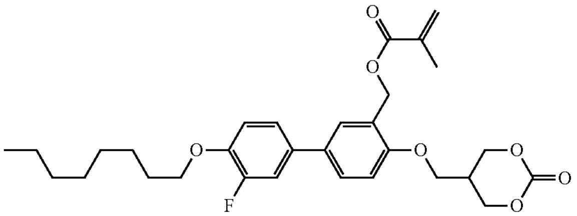

(Physical Properties)

Melting point: 81° C.

$^1$H-NMR (solvent:heavy chloroform): δ: 0.88 (t, 3H), 1.29-1.31 (m, 6H), 1.44-1.49 (m, 2H), 1.56 (s, 3H), 1.83 (q, 2H), 1.97 (s, 2H), 2.69-2.76 (m, 1H), 4.05 (t, 2H), 4.16 (d, 2H), 4.35-4.38 (m, 2H), 4.59-4.62 (m, 2H), 5.28 (s, 2H), 5.60 (s, 1H), 6.14 (s, 1H), 6.90 (d, 1H), 7.01 (t, 1H), 7.21-7.29 (m, 2H), 7.46 (dd, 1H), 7.53 (d, 1H)

$^{13}$C-NMR (solvent:heavy chloroform): δ: 14.9, 17.3, 22.7, 25.9, 27.9, 29.6, 31.8, 64.0, 68.7, 68.8, 72.8, 114.7, 122.3, 125.6, 128.4, 135.5, 138.6, 151.0, 158.3, 166.0

Example 2

16 g of 3-(3,4-bis (methacryloyloxy) phenyl) propionic acid, 15 g of 4'-((2,2-dimethyl-1,3-dioxane-5-yl) methoxy)-[1,1'-biphenyl]-4-ol, 500 mg of dimethylaminopyridine, and 200 ml of dichloromethane were added to a reaction vessel including a stirring device, a cooling device, and a thermometer, and the reaction vessel was cooled to 10° C. or lower. After that, 8 g of diisopropylcarbodiimide was slowly added dropwise. After completing the dropwise addition, the reaction was carried out at room temperature for 5 hours. After completing the reaction, the organic layer was washed with water or a saturated saline solution, and the solvent was distilled. Then, 150 ml of tetrahydrofuran (THF) was added, and 20 ml of a 10% hydrochloric acid was slowly added dropwise. After completing the reaction, the resultant material was cooled and a target material was extracted by ethyl acetate. The organic layer was washed with water or a saturated saline solution, and the solvent was distilled. After that, dispersion washing with toluene and purification with an alumina column were performed, and 21 g of a compound represented by formula (7) was obtained.

[Chem. 100]

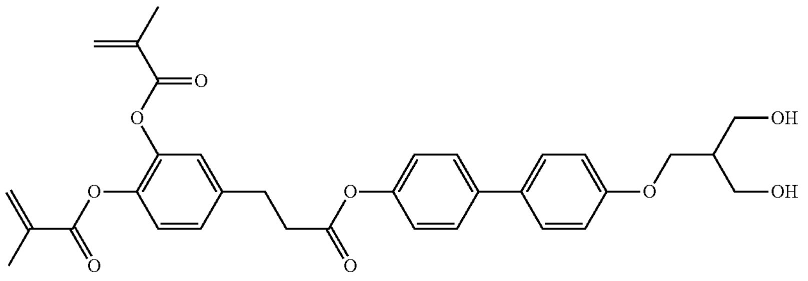
(7)

(Physical Properties)
Melting point: 121° C.

Example 3

10 g of the compound (7) and 300 ml of dichloromethane were added to a reaction vessel including a stirring device, a cooling device, and a thermometer, and the reaction vessel was cooled to 10° C. or lower. Then, 5.6 g of ethyl chloroformate was slowly added dropwise. After completing the dropwise addition, the resultant material was stirred for 30 minutes. Then, 5.7 g of triethylamine was added dropwise. After completing the reaction, the organic layer was washed with water or a saturated saline solution, and the solvent was distilled. After that, the purification with a silica column was performed, 8.5 g of a target compound represented by a compound (8) was obtained.

[Chem. 101]

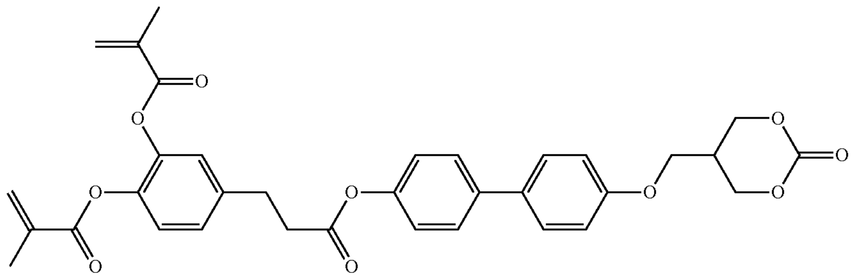
(8)

(Physical Properties)

Melting point: 102° C.

$^1$H-NMR (solvent:heavy chloroform): δ: 1.56 (s, 3H), 1.95 (t, 2H), 2.20 (t, 2H), 2.69-2.76 (m, 1H), 4.05 (m, 2H), 4.16 (m, 4H), 5.60 (s, 2H), 6.14 (s, 2H), 6.87-6.99 (m, 3H), 7.05 (s, 1H), 7.21-7.29 (m, 3H), 7.43 (d, 2H), 7.55 (d, 2H)

$^{13}$C-NMR (solvent:heavy chloroform): δ: 17.3, 27.9, 29.6, 68.7, 68.8, 72.8, 109.5, 114.7, 122.3, 125.6, 128.4, 128.3, 129.4, 135.5, 138.6, 151.0, 158.3, 159.7, 166.0

Example 4

10 g of 5-bromosalicylaldehyde, 1 g of pyridinium para-toluenesulfonate, and 100 ml of dichloromethane were added to a reaction vessel including a stirring device, a cooling device, and a thermometer, 20 ml of a dichloromethane solution of 10 g of 3,4-dihydro-2H pyran was added dropwise at room temperature, and a reaction was carried out for 5 hours. After completing the reaction, the organic layer was washed with water or a saturated saline solution, the solvent was distilled, and 12 g of a compound represented by formula (9) was obtained.

[Chem. 102]

(9)

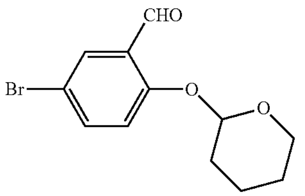

Then, a compound represented by Compound formula (10) shown below was obtained by the same method as in Example 1.

[Chem. 103]

(10)

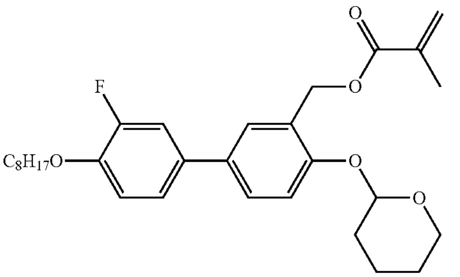

10 g of the compound (10) and 100 ml of THF were added to a reaction vessel including a stirring device and a thermometer, and 5 ml of a 10% hydrochloric acid/5 ml of methanol was slowly added dropwise. After completing the reaction, a target material was extracted by ethyl acetate. The organic layer was washed with water or a saturated saline solution, and the solvent was distilled. After that, dispersion washing with toluene and purification with an alumina column were performed, and 8 g of a compound represented by formula (11) was obtained.

[Chem. 104]

(11)

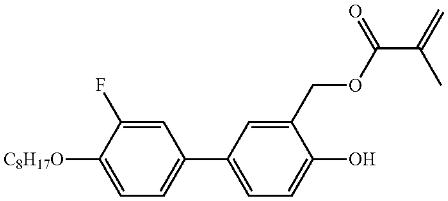

15 g of sesamol, 14 g of 2-chloroethanol, 28 g of triphenylphosphine, and 200 ml of THF were added to a reaction vessel including a stirring device, a cooling device, and a thermometer, and the reaction vessel was cooled to 10° C. or lower. 22 g of diisopropyl azodicarboxylate was slowly added dropwise. After completing the dropwise addition, the temperature of the reaction vessel was returned to room temperature, and the reaction was carried out for 5 hours. After completing the reaction, the resultant material was cooled, 200 ml of ethyl acetate was added, the organic layer was washed with water or a saturated saline solution, the solvent was distilled, and 17 g of a compound represented by formula (12) was obtained.

[Chem. 105]

(12)

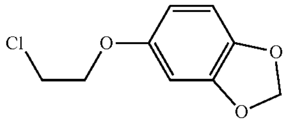

17 g of the compound (12), 57 g of gallic acid tertiary butyl ester, 50 g of potassium carbonate, and 500 ml of N, N-dimethylformamide were added to a reaction vessel including a stirring device, a cooling device, and a thermometer, and a reaction was carried out at 90° C. for 5 hours. After completing the reaction, the resultant material was cooled, 400 ml of ethyl acetate was added, the organic layer was washed with water or a saturated saline solution, and the solvent was distilled. The obtained compound was dissolved with 200 ml of dichloromethane and 200 ml of formic acid, and a reaction was carried out with heating and refluxing for 5 hours. The reaction vessel was cooled to room temperature, 300 ml of pure water was added, and crystals were precipitated. The precipitated crystal was dissolved in 200 ml of THF and 400 ml of ethyl acetate, the organic layer water or a saturated saline solution, the solvent was distilled, and 42 g of a compound represented by formula (13) was obtained.

[Chem. 106]

(13)

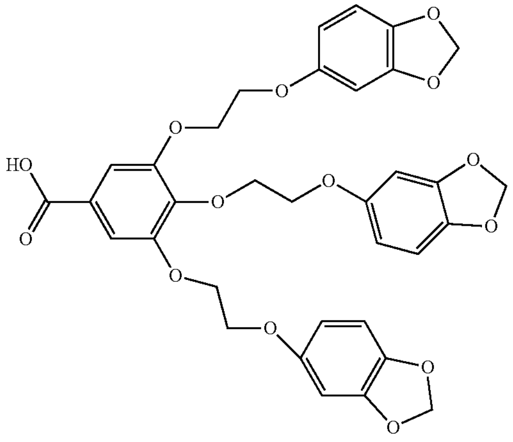

8 g of the compound (11), 12.8 g of the compound (13), 200 mg of dimethylaminopyridine, and 200 ml of dichloromethane were added to a reaction vessel including a stirring device, a cooling device, and a thermometer, and the reaction vessel was cooled approximately at 10° C. After that, 2.6 g of diisopropylcarbodiimide was slowly added dropwise. After completing the dropwise addition, the reaction was carried out at room temperature for 5 hours. After completing the reaction, the organic layer was washed with water or a saturated saline solution, and the solvent was distilled. After that, the purification with a silica gel column was performed, and 16 g of a target compound represented by Compound (14) was obtained.

$^{13}$C-NMR (solvent:heavy chloroform): δ: 17.3, 62.9, 68.7, 68.8, 72.8, 101.4, 109.5, 114.7, 122.3, 125.6, 128.4, 128.3, 135.5, 138.6, 158.3, 159.7, 166.0

Example 5

20 g of 3-bromo-4'-(dodecyloxy)-3'-fluoro-(1,1'-biphenyl)-4-ol, 0.5 g of pyridinium paratoluenesulfonate, and 100 ml of dichloromethane were added to a reaction vessel including a stirring device, a cooling device, and a thermometer, 20 ml of a dichloromethane solution of 8 g of 3,4-dihydro-2H pyran were added dropwise at room temperature, and the reaction was carried out for 5 hours. After completing the reaction, the organic layer was washed with water or a saturated saline solution, the solvent was distilled, and 28 g of a compound represented by formula (15) was obtained.

[Chem. 108]

(15)

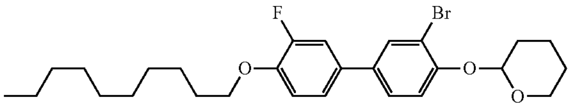

Then, 28 g of the compound (15), 1 g of copper iodide, 3 g of tetrakistriphenylphosphine palladium, 200 ml of tetrahydrofuran, and 100 ml of pure water were added to a reaction vessel including a stirring device, a cooling device, and a thermometer, and the resultant material was stirred at room temperature. After that, 33 g of 2-ethanolamine was

[Chem. 107]

(14)

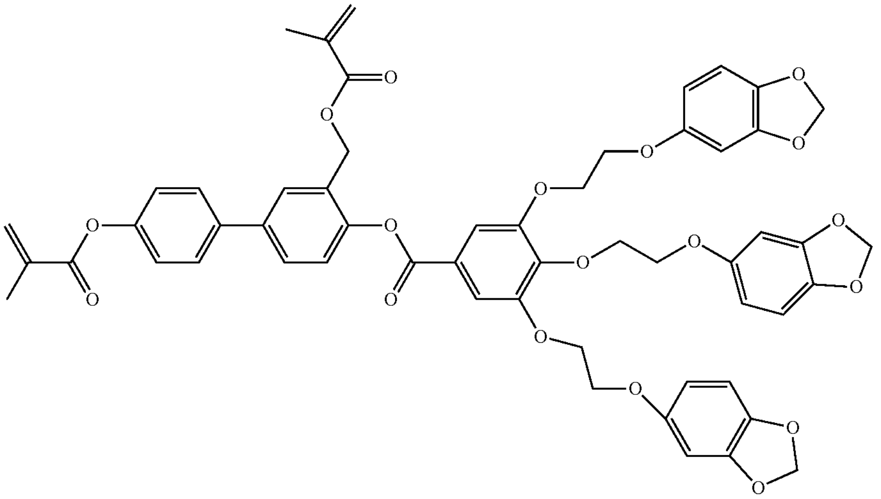

(Physical Properties)

Oily Compound

1H-NMR (solvent:heavy chloroform): δ: 1.76 (s, 6H), 4.12 (t, 12H), 4.84 (s, 2H), 5.47 (s, 3H), 5.60 (s, 1H), 6.14 (s, 1H), 6.90-7.02 (m, 9H), 7.15-7.29 (m, 4H), 7.35 (s, 1H), 7.65-7.82 (m, 4H)

added dropwise, the reaction vessel was heated to 60° C., and 5 g of propargyl alcohol was slowly added dropwise. After completing the reaction, the resultant material was cooled, 300 ml of toluene was added to the reaction solution, washing was performed with a saturated aqueous ammonium chloride solution or a saturated saline solution, and the solvent was distilled. Then, the resultant material was dissolved in dichloromethane, the purification with an alumina column and recrystallization with methanol were performed, and 21 g of a compound represented by formula (16) was obtained.

[Chem. 109]

(16)

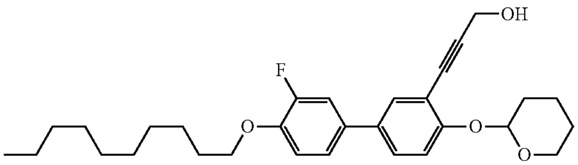

21 g of the compound (16), 1 g of 5% palladium carbon, 100 ml of tetrahydrofuran, and 20 ml of ethanol were added to an autoclave vessel including a stirring device, a reduction reaction (room temperature, 8 hours) was carried out with hydrogen of 0.3 MPa. After filtering the reaction solution, the reaction solvent was distilled, and 20 g of a compound represented by formula (17) was obtained.

[Chem. 110]

(17)

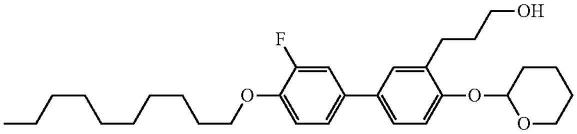

Then, 20 g of the compound represented by formula (17), 4.6 g of triethylamine, and 100 ml of dichloromethane were added to a reaction vessel including a stirring device, a cooling device, and a thermometer, and the reaction vessel was cooled to 5° C. or lower under a nitrogen gas atmosphere. Then, 5 g of methacrylic acid chloride was slowly added dropwise. After completing the dropwise addition, the reaction was carried out at a temperature of 20° C. or lower for 3 hours. After completing the reaction, dichloromethane was added, and the organic layer was washed with pure water or a saturated saline solution. After distilling the solvent, the resultant material was dissolved in 100 ml of tetrahydrofuran. The tetrahydrofuran solution was moved to the reaction vessel including a stirring device, 10 ml of a methanol solution to which 0.5 ml of hydrochloric acid was slowly added, and the reaction was carried out for 2 hours. After completing the reaction, the resultant material was washed with 400 ml of ethyl acetate, water, or a saturated saline solution. After distilling the solvent, 16 g of a compound represented by formula (18) was obtained by the purification with a silica gel column.

[Chem. 111]

(18)

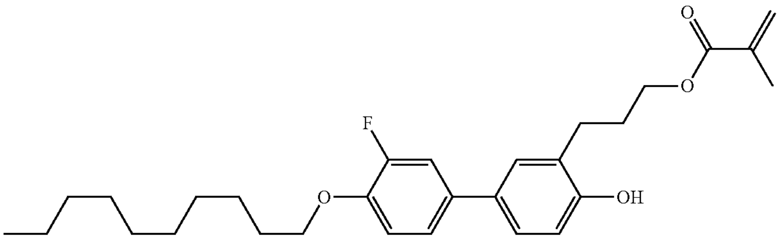

16 g of the compound represented by formula (18), 11 g of triphenylphosphine, 5 g of 5-(hydroxymethyl)-1, 3-dioxane-2-one, and 100 ml of dichloromethane were added to a reaction vessel including a stirring device, a cooling device, and a thermometer, and the reaction vessel was cooled to 5° C. or lower. After that, 8.2 g of diisopropyl diazocarboxylate (DIAD) was added dropwise. After completing the dropwise addition, the resultant material was stirred at room temperature for 5 hours, and the reaction was completed. After completing the reaction, 200 ml of dichloromethane was added, and the organic layer was washed with pure water or a saturated saline solution. After distilling the solvent, 13 g of a target compound represented by Compound (19) was obtained by the purification with a silica gel column and the recrystallization with methanol.

[Chem. 112]

(19)

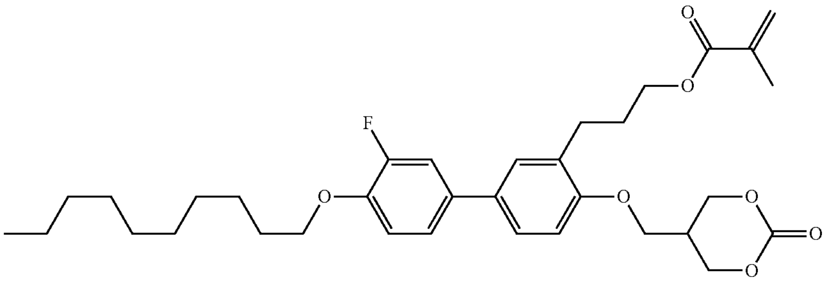

(Physical Properties)

Melting point: 55° C.

$^1$H-NMR (solvent:heavy chloroform): δ: 0.88 (t, 3H), 1.44-1.49 (m, 2H), 1.51-1.56 (m, 2H), 1.81-1.85 (m, 2H), 1.98 (s, 3H), 2.02-2.03 (m, 2H), 2.73-2.78 (m, 3H), 4.05 (t, 2H), 4.12 (d, 2H), 4.21 (t, 2H), 4.47 (m, 2H), 4.59 (m, 2H), 5.56 (s, 1H), 6.09 (s, 1H), 6.83 (d, 1H), 7.02 (t, 1H), 7.19-7.27 (m, 4H), 7.32 (d, 1H), 7.34 (m, 1H)

$^{13}$C-NMR (solvent:heavy chloroform): δ: 14.1, 18.3, 22.6, 25.9, 27.0, 28.9, 29.2, 29.3, 31.8, 64.2, 64.4, 69.0, 69.5, 111.2, 114.5, 115.1, 122.1, 125.4, 128.7, 130.4, 136.4, 138.6, 147.0, 149.5, 155.0, 167.0

Example 6

18.5 g of 4-octylphenol, 12 g of ethylene glycol monotertiary butyl ether, 35 g of triphenylphosphine, and 300 ml of dichloromethane were added to a reaction vessel including a stirring device, a cooling device, and a thermometer, and the reaction vessel was cooled to 5° C. or lower. After that, 22 g of DIAD was added dropwise. After completing the dropwise addition, the resultant material was stirred at room temperature for 5 hours, and the reaction was completed. After completing the reaction, 200 ml of dichloromethane was added, and the organic layer was washed with pure water or a saturated saline solution. After distilling the solvent, 23 g of a compound represented by formula (20) was obtained by the purification with a silica gel column.

[Chem. 113]

(20)

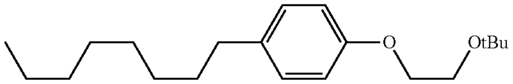

23 g of the compound represented by formula (20) and 100 ml of methylene chloride were added to a reaction vessel including a stirring device, a cooling device, and a thermometer, the reaction vessel was maintained at a temperature of 5° C. or lower in a cooling bath, and 50 ml of trifluoroacetic acid was slowly added dropwise. After completing the dropwise addition, the temperature of the reaction vessel was returned to room temperature, and the reaction was carried out for 1 hour. After completing the reaction, the reaction solution was cooled to 10° C. or lower, and 50 ml of pure water was slowly added. 150 ml of methylene chloride was added, the organic layer was washed with pure water, or a saturated sodium hydrogen carbonate 5% aqueous hydrochloric acid solution, further washed with a saturated saline solution, and the organic layer was dried with anhydrous sodium sulfate. The solvent was distilled, and 18 g of a compound represented by formula (21) was obtained.

[Chem. 114]

(21)

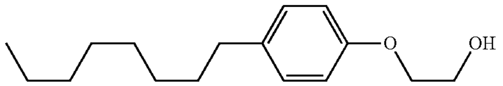

Then, 9 g of the compound represented by formula (21), 18 g of 3,5-Difluoro-3'-iodo-4'-((2,2,5-trimethyl-1,3-dioxane-5-yl)-(1,1'-biphenyl)-4-ol, 12 g of triphenylphosphine, and 200 ml of dichloromethane were added to a reaction vessel including a stirring device, a cooling device, and a thermometer, and the reaction vessel was cooled to 5° C. After that, 9 g of DIAD was added dropwise. After completing the dropwise addition, the resultant material was stirred at room temperature for 5 hours, the reaction was completed. After completing the reaction, 200 ml of dichloromethane was added, and the organic layer was washed with pure water or a saturated saline solution. After distilling the solvent, 22 g of a compound represented by formula (22) was obtained by the purification with an alumina column.

[Chem. 115]

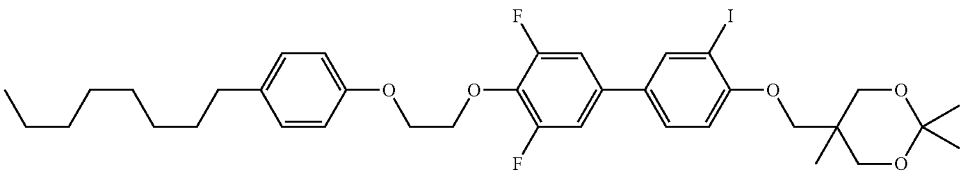

(22)

Then, 22 g of the compound (22), 0.5 g of copper iodide, 1.5 g of tetrakistriphenylphosphine palladium, 200 ml of tetrahydrofuran, and 100 ml of pure water were added to a reaction vessel including a stirring device, a cooling device, and a thermometer, and the resultant material was stirred at room temperature. After that, 18 g of 2-ethanolamine was added dropwise, the reaction vessel was heated to 60° C., and 2 g of propargyl alcohol was slowly added dropwise. After completing the reaction, the resultant material was cooled, 300 ml of toluene was added to a reaction solution, washed with a saturated aqueous ammonium chloride solution or a saturated saline solution, and the solvent was distilled. After that, the resultant material was dissolved in dichloromethane, and the purification with an alumina column and the recrystallization with methanol were performed. 1 g of 5% palladium carbon, 200 ml of tetrahydrofuran, and 40 ml of ethanol were added to an autoclave vessel including a stirring device, and a reduction reaction (40° C., 8 hours) was carried out with hydrogen of 0.3 MPa. After filtering the reaction solution, the reaction solvent was distilled, and 15.7 g of a compound represented by formula (23) was obtained.

[Chem. 116]

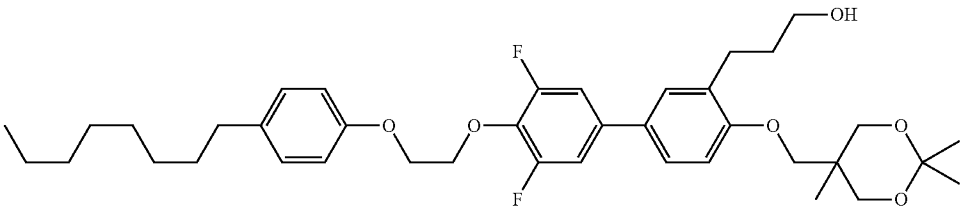

(23)

15.7 g of the compound represented by formula (23), 3 g of methacrylic acid, 150 mg of dimethylaminopyridine, 150 mg of dimethylaminopyridine, and 100 ml of methylene chloride were added to a reaction vessel including a stirring device, a cooling device, and a thermometer, and the reaction vessel was maintained at a temperature of 5° C. or lower in a cooling bath, and 3.8 g of diisopropylcarbodiimide was slowly added dropwise under the nitrogen gas atmosphere. After completing the dropwise addition, the temperature of the reaction vessel was returned to room temperature, and the reaction was carried out for 5 hours. After filtering the reaction solution, the filtrate was concentrated, dissolved by adding 100 ml of tetrahydrofuran, and added to a reaction vessel including a stirring device, and 15 ml of 10% aqueous hydrochloric acid was added and stirred for 30 minutes. After that, the resultant material was washed with 400 ml of ethyl acetate, water, or a saturated saline solution, the solvent was distilled, and 12.5 g of a target compound represented by Compound (24) was obtained by the purification with a silica gel column.

[Chem. 117]

(24)

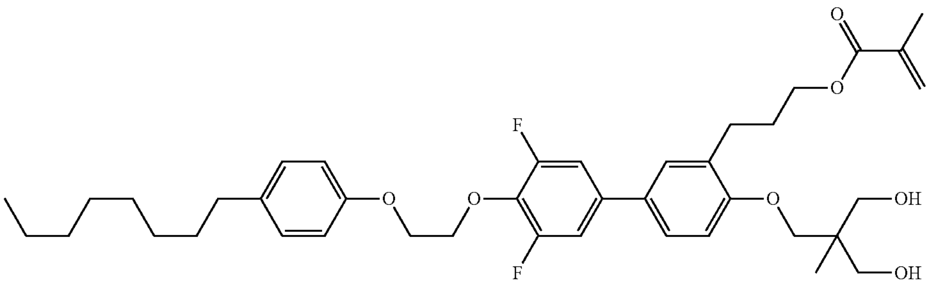

(Physical Properties)

Oily Compound $^{1}$H-NMR (solvent:heavy chloroform): δ: 0.88 (t, 6H), 1.26-1.49 (m, 10H), 1.63 (m, 2H), 1.98 (s, 3H), 2.02-2.03 (m, 2H), 2.63-2.70 (m, 4H), 3.38-3.41 (m, 4H), 3.80 (s, 2H), 4.21 (t, 2H), 4.22 (m, 2H), 4.47-4.50 (m, 4H), 5.56 (s, 1H), 6.09 (s, 1H), 6.83 (d, 2H), 7.02 (t, 1H), 7.19-7.27 (m, 4H), 7.62 (m, 2H)

$^{13}$C-NMR (solvent:heavy chloroform): δ: 14.1, 14.8, 18.3, 22.7, 26.3, 28.9, 29.3, 31.8, 34.2, 35.7, 41.4, 65.5, 67.4, 69.0, 70.2, 111.2, 114.5, 115.0, 124.9, 127.0, 129.6, 133.4, 136.0, 147.0, 149.5, 155.0, 167.0

Example 7

Adjustment of Liquid Crystal Composition

In a case where the content of the composition configured with the following compounds at a mixing ratio:

[Chem. 118]

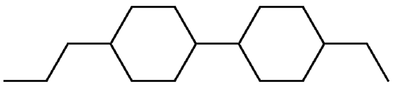

20 wt%

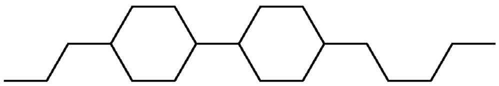

5 wt%

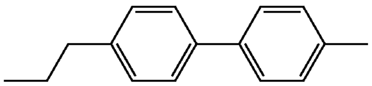

9 wt%

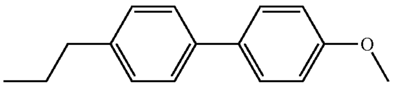

6 wt%

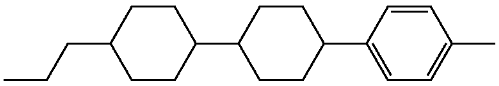

7 wt%

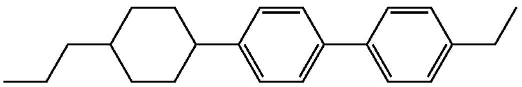

6 wt%

-continued

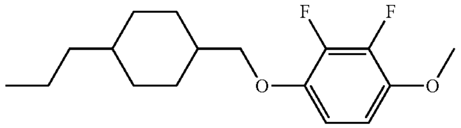

6 wt%

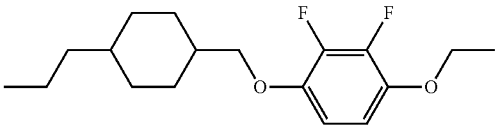

8 wt%

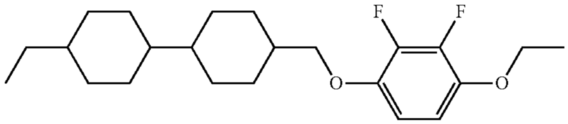

6 wt%

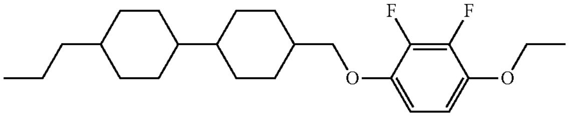

8 wt%

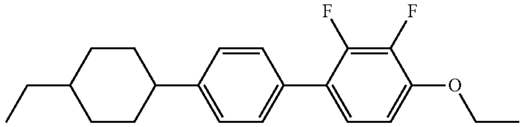

7 wt%

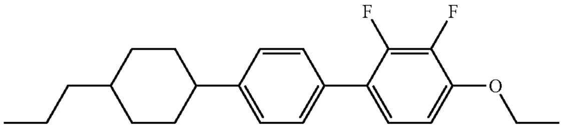

6 wt%

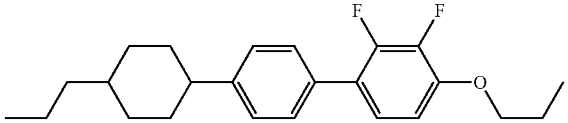

6 wt% was set as 100% by weight, a composition, to which 0.3% by weight of the following polymerizable compound (R-1-0) was added, was set as LC-1.

[Chem. 119]

(R-1-0)

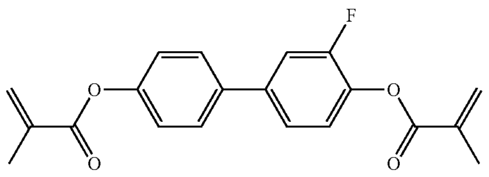

A nematic phase-isotropic liquid phase transition temperature (TNI) of LC-1 was set as 75° C., a solid phase-nematic phase transition temperature (TCN) was 33° C., a refractive index anisotropy (Δn) was 0.11, a dielectric anisotropy (Δε) was −2.8, and a rotational viscosity (γ1) was 98 mPa·s. All of the refractive index anisotropy (Δn), the dielectric anisotropy (Δε), and the rotational viscosity (γ1) are measurement results obtained at 25° C. (the same applies hereinafter).

0.3% by weight of a compound (P-J-1) corresponding to the compound (i):

[Chem. 120]

(P-J-1)

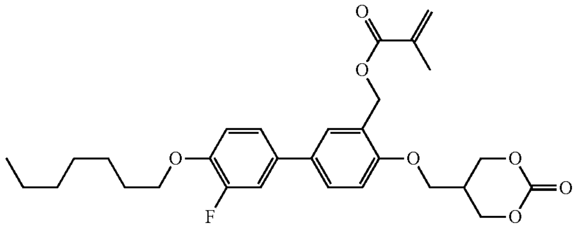

was added to 100% by weight of LC-1100, and a liquid crystal composition was prepared.

Examples 8 to 24

A liquid crystal composition was prepared in the same manner as in Example 7, except that the following compounds were added to LC-1 with the added amount shown in Table 1, instead of the compound (P-J-1) with the added amount of 0.3% by weight.

[Chem. 121]

(P-J-2)

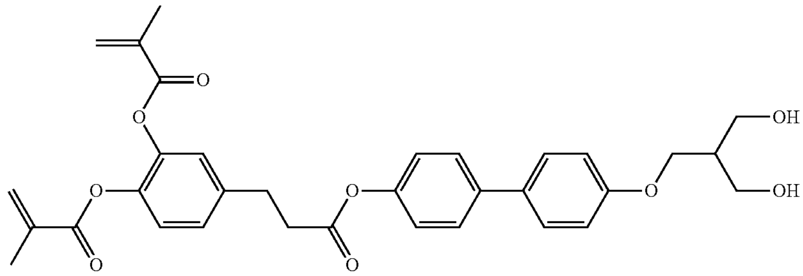

(P-J-3)

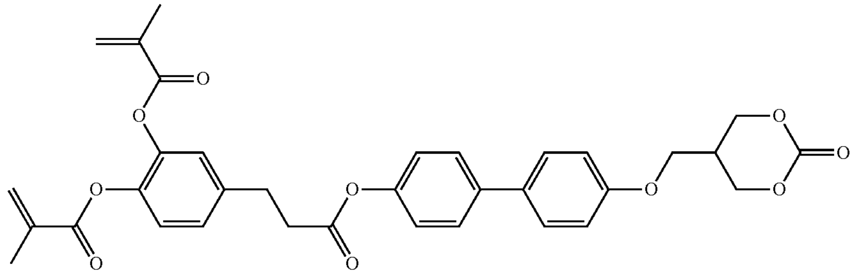

-continued
(P-J-4)
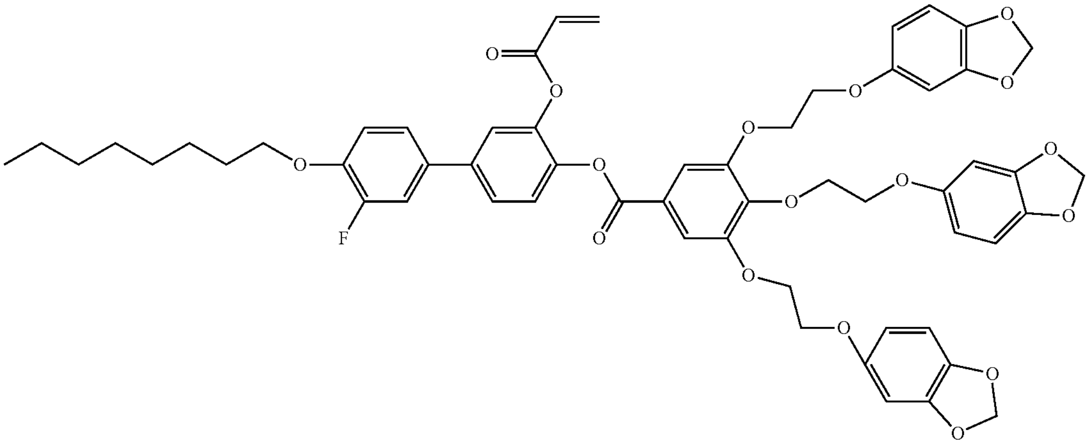
(P-J-5)
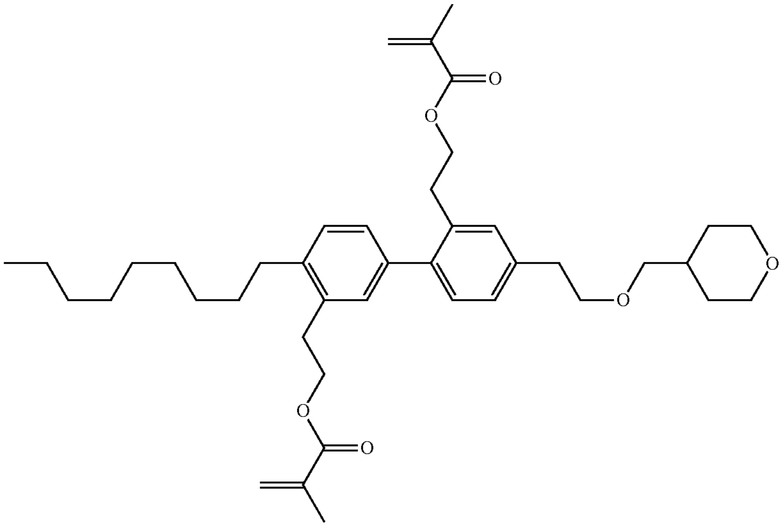
(P-J-6)
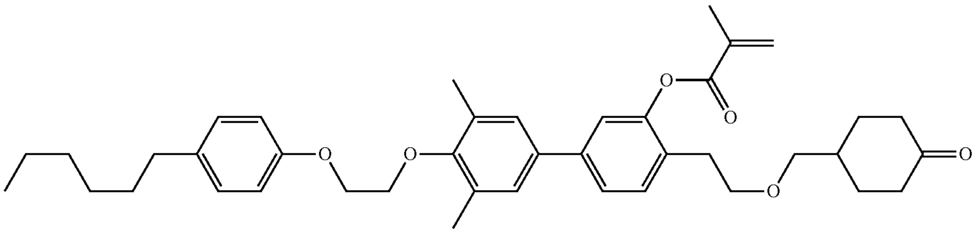
[Chem. 122]
(P-J-7)
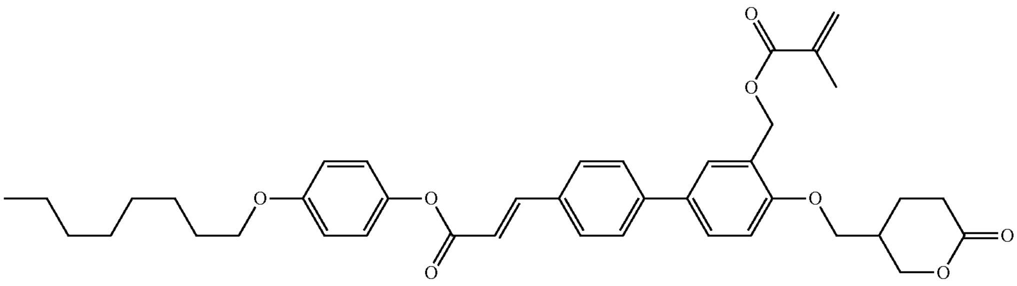

-continued (P-J-8)

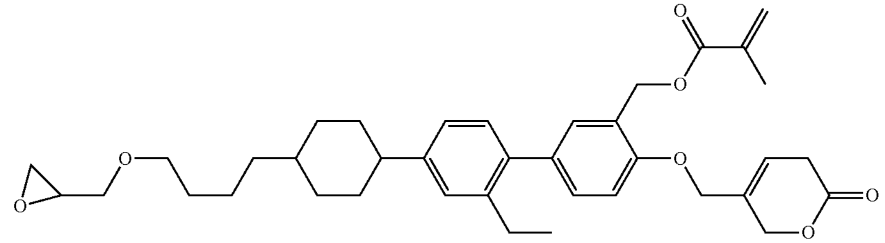

(P-J-9)

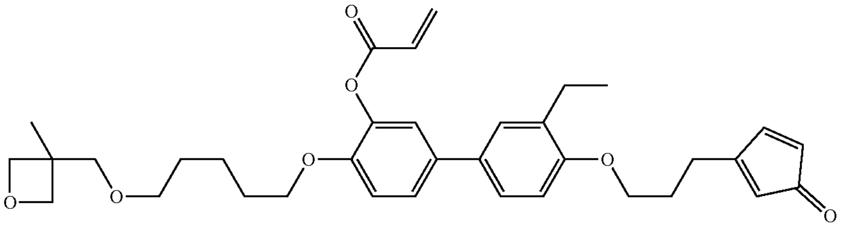

Example 25

A liquid crystal composition was prepared in the same manner as in Example 7, except that a composition LC-2, to which 0.3% by weight of the polymerizable compound (R-1-0) was added, in a case where the content of the composition configured with the following compounds at a mixing ratio:

[Chem. 123]

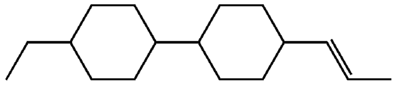

20 wt%

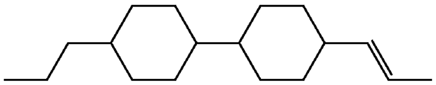

14.5 wt%

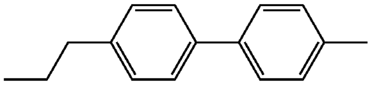

9.5 wt%

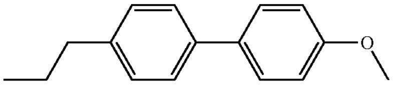

3 wt%

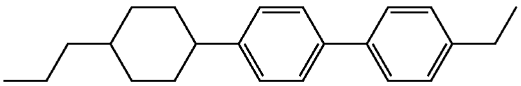

5.5 wt%

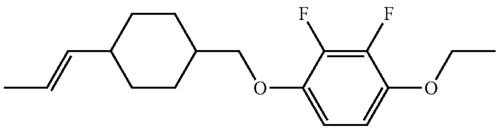

9 wt%

-continued

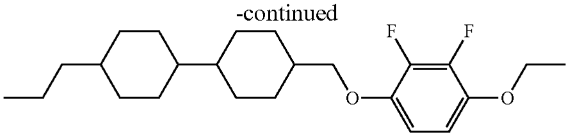

20.5 wt%

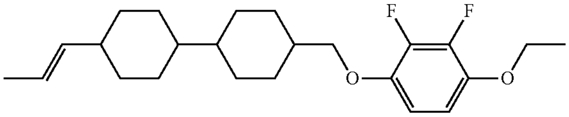

8 wt%

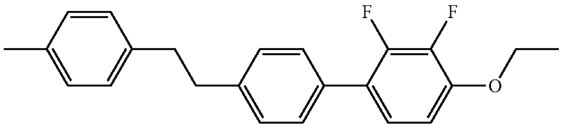

5 wt%

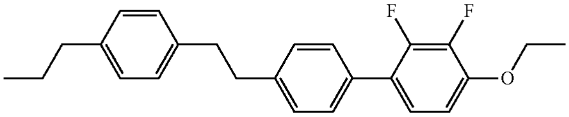

5 wt% was set as 100% by weight, was used, instead of the composition LC-1.

$T_{NI}$ of LC-2 was 81° C., $T_{CN}$ was −54° C., Δn was 0.11, Δε was −3.0, and $\gamma_1$ was 95 mPa·s.

Examples 26 to 41

A liquid crystal composition was prepared in the same manner as in Example 25, except that additive compounds shown in Table 1 or Table 3 shown below were added to LC-2 with the added amount shown in Table 1 or Table 3, instead of the compound (P-J-1) with the added amount of 0.3% by weight in Example 25.

Examples 42 to 137

A liquid crystal composition was prepared in the same manner as in Example 7, except that additive compounds shown in Table 3, Table 5, Table 7, or Table 9 shown below were respectively added with the added amount corresponding to Table 3, Table 5, Table 7, or Table 9, instead of the compound (P-J-1) with the added amount of 0.3% by weight in Example 7.

Examples 138 to 151

A liquid crystal composition was prepared in the same manner as in Example 8, except that the amount of the additive compound 1 was set as the added amount shown in Table 12 and amount of the additive compound 2 shown in Table 12 was set as the added amount shown in Table 12, instead of the compound (P-J-1) with the added amount of 0.3% by weight in Example 8.

[Chem. 124]

(P-J-10)

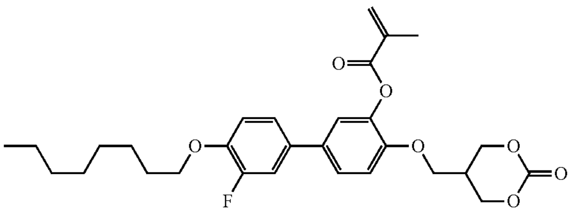

(P-J-11)

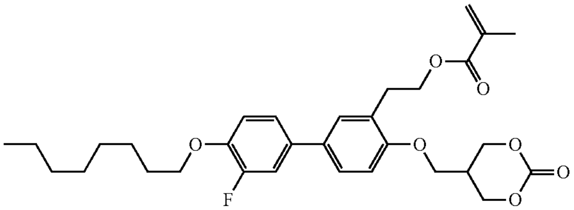

(P-J-12)

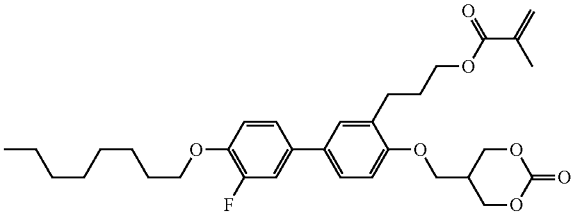

(P-J-13)

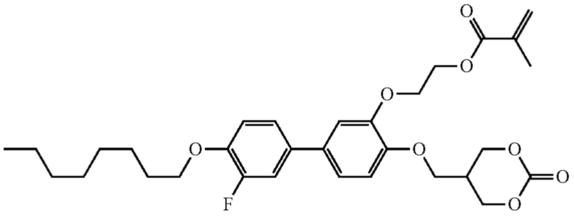

(P-J-14)

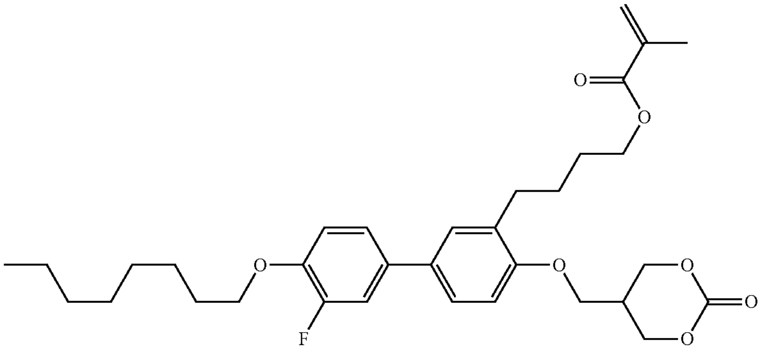

[Chem. 125]

(P-J-15)

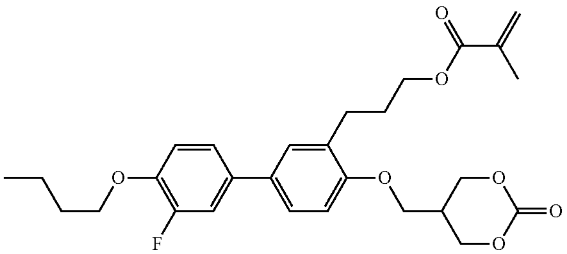

(P-J-16)

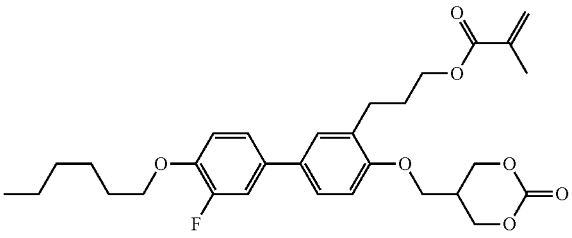

-continued
(P-J-17)
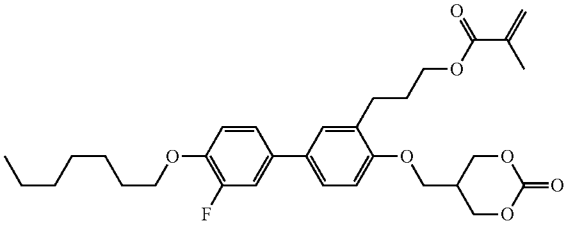
(P-J-18)
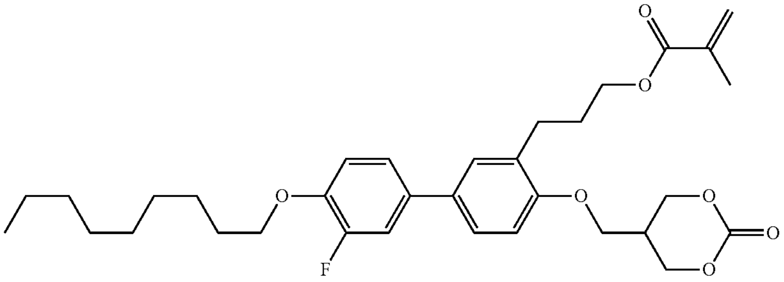
(P-J-19)
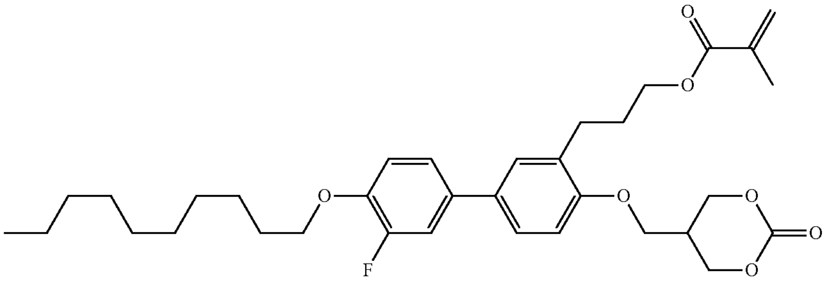
(P-J-20)
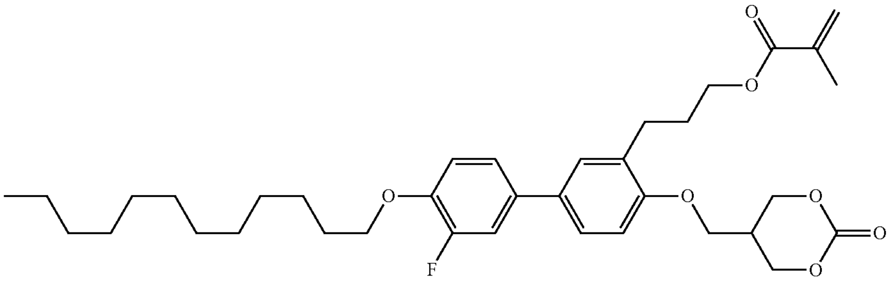
[Chem. 126]
(P-J-21)
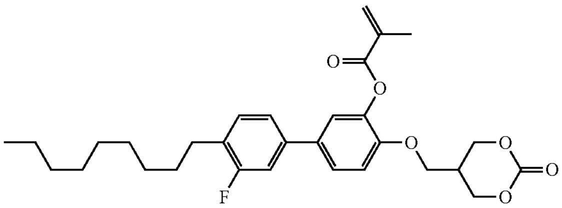
(P-J-22)
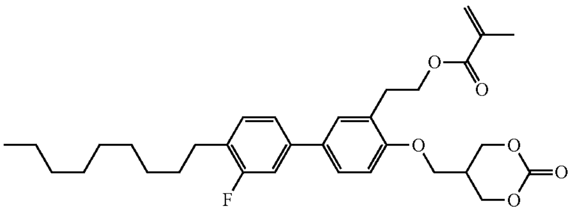
(P-J-23)
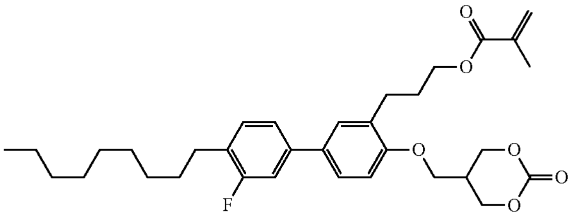
(P-J-24)
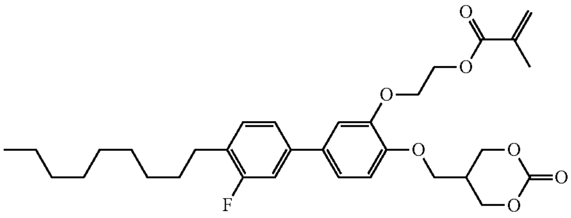

-continued
[Chem. 127]
(P-J-25)
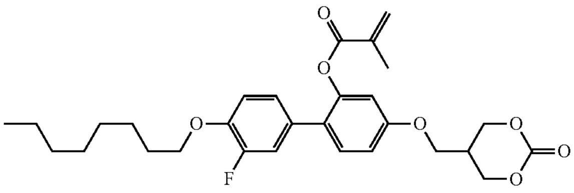
(P-J-26)
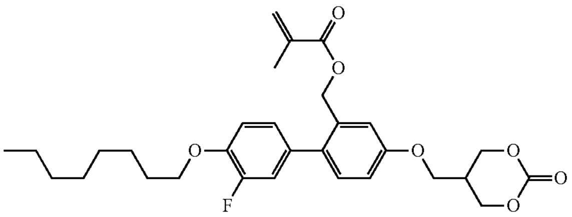
(P-J-27)
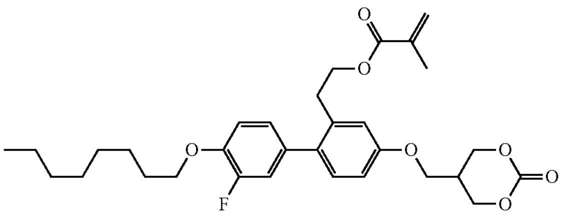
(P-J-28)
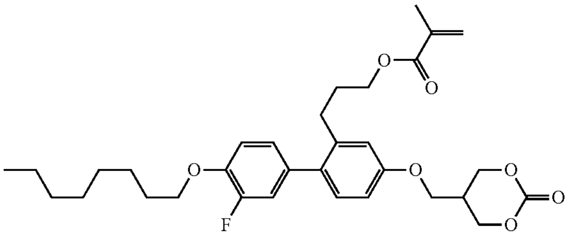
(P-J-29)
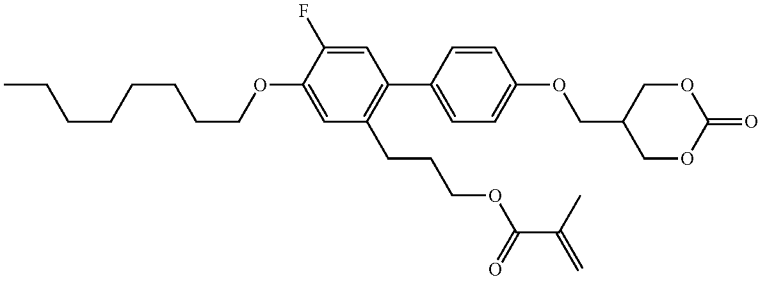
[Chem. 128]
(P-J-30)
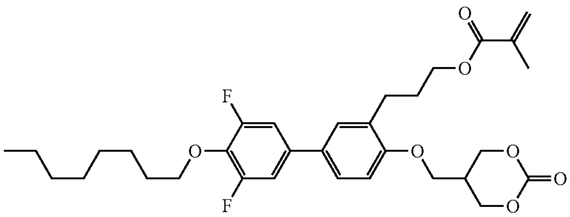
(P-J-31)
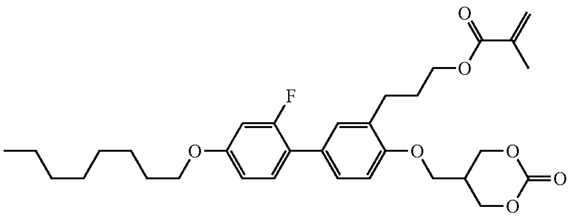
(P-J-32)
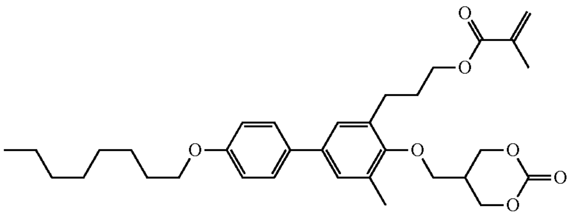
(P-J-33)
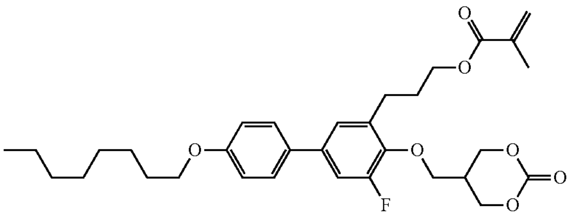
(P-J-34)
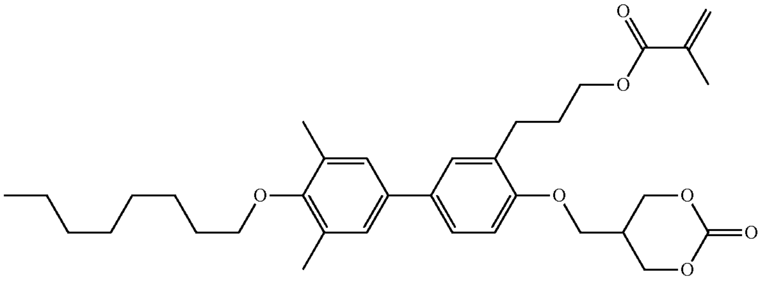

-continued
[Chem. 129]
(P-J-35)
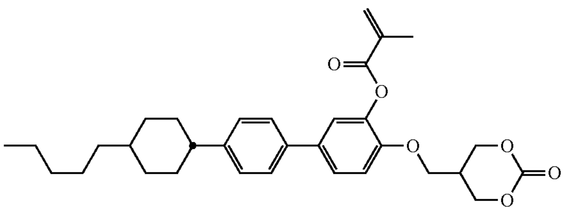
(P-J-36)
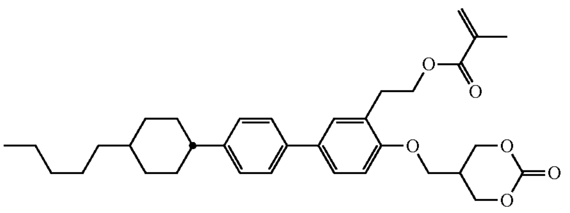
(P-J-37)
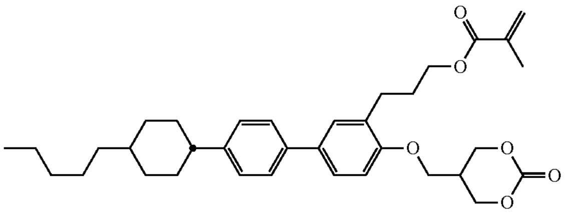
(P-J-38)
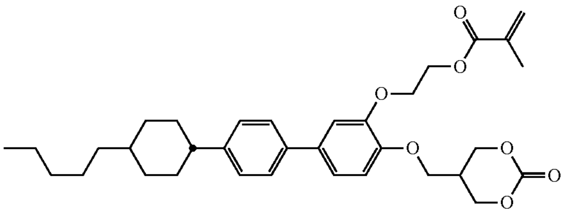
[Chem. 130]
(P-J-39)
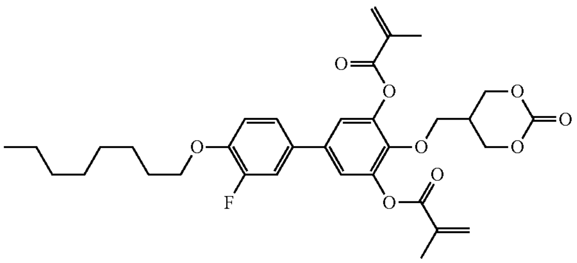
(P-J-40)
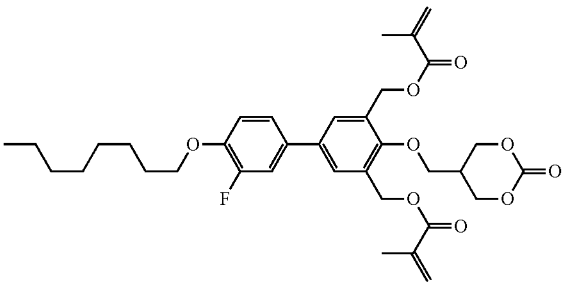
(P-J-41)
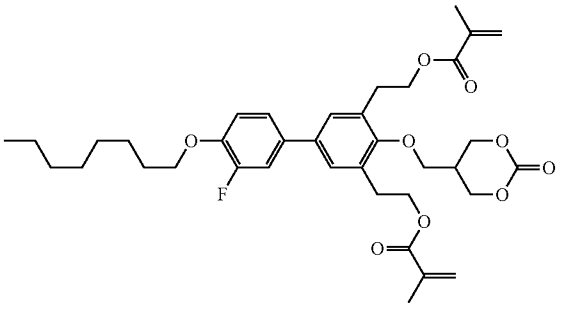
(P-J-42)
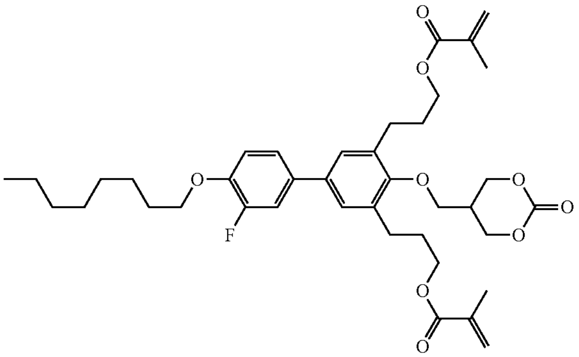
[Chem. 131]
(P-J-43)
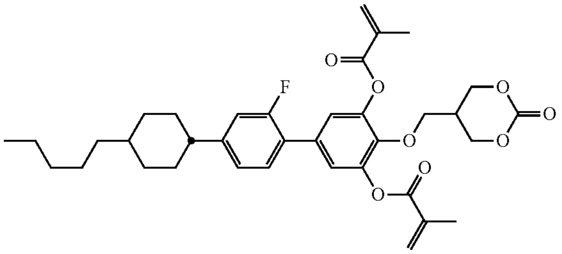
(P-J-44)
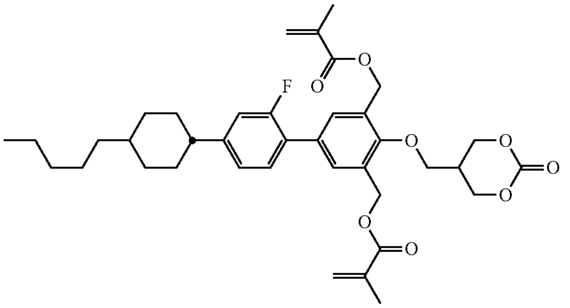

-continued
(P-J-45)
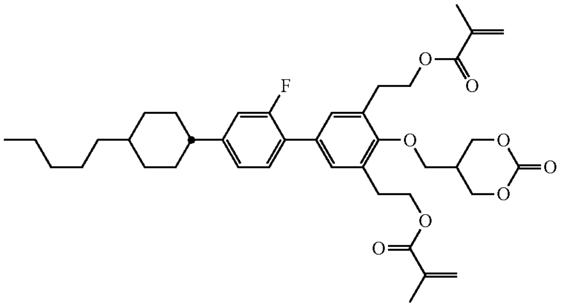
(P-J-46)
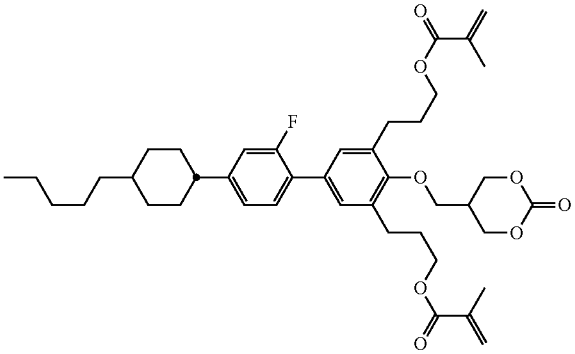
[Chem. 132]
(P-J-47)
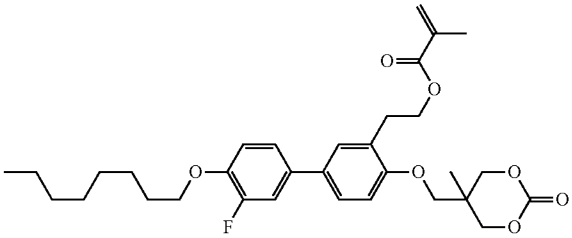
(P-J-48)
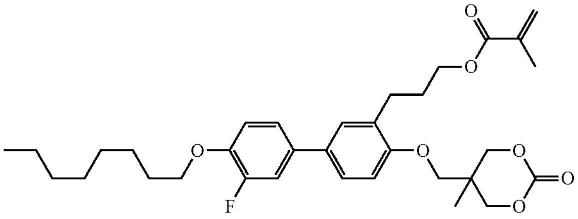
(P-J-49)
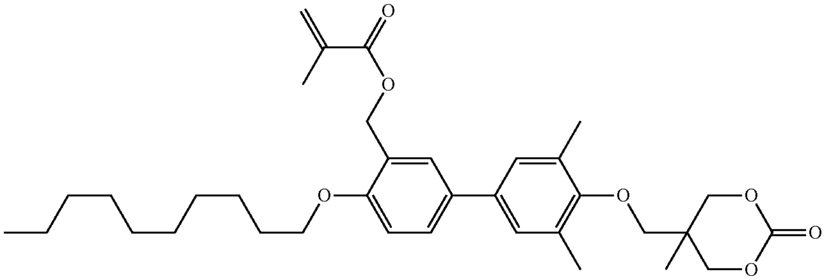
(P-J-50)
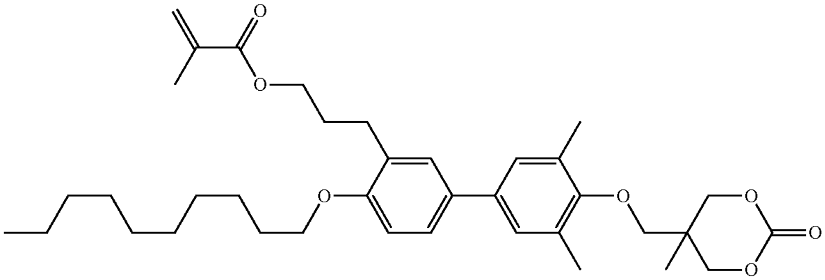
[Chem. 133]
(P-J-51)
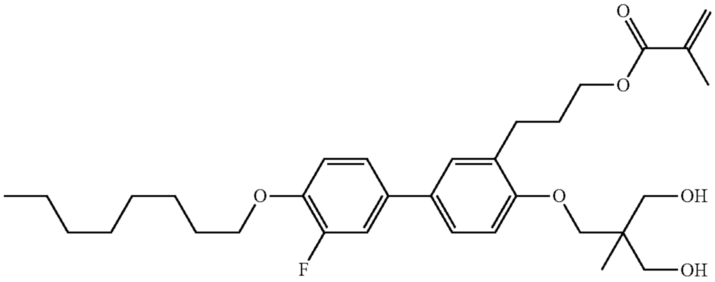

-continued
(P-J-52)
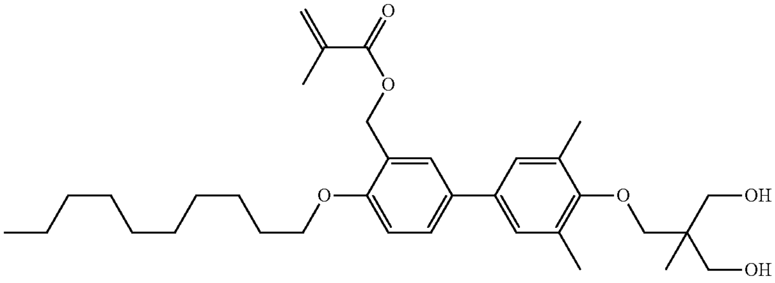
(P-J-53)
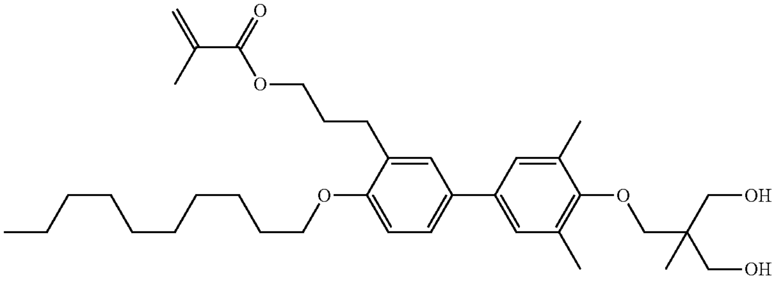
(P-J-54)
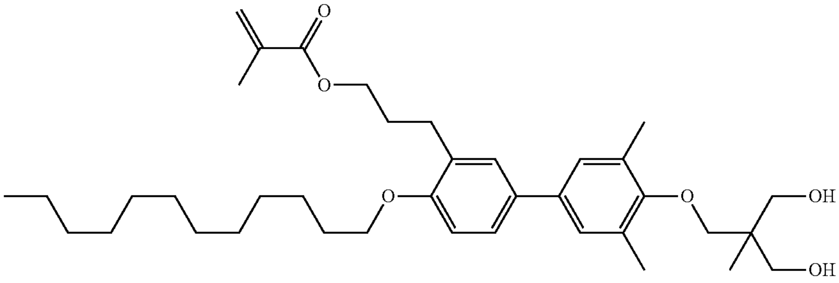
(P-J-55)
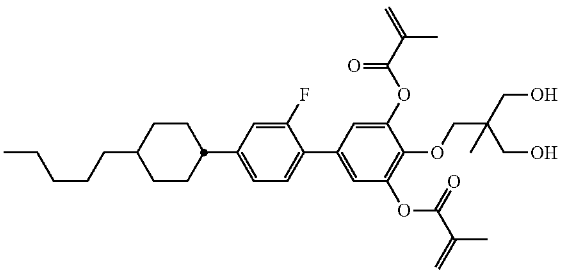
(P-J-56)
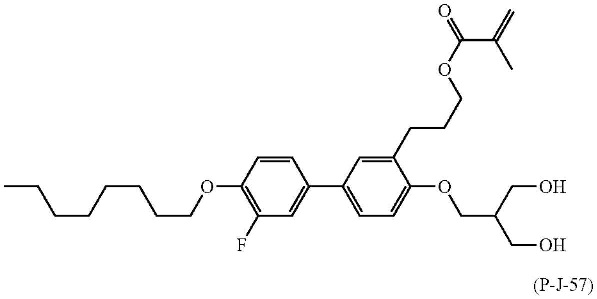
(P-J-57)
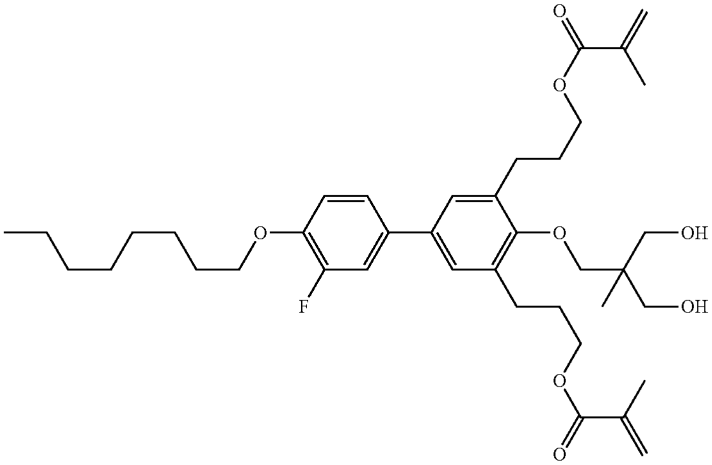

Comparative Example 1

A liquid crystal composition was prepared in the same manner as in Example 7, except that the compound (P-J-1) was not used.

Comparative Examples 2 to 11

A liquid crystal composition was prepared in the same manner as in Example 7, except that the following compound was added to LC-1 or LC-2 with the added amount shown in Table 13, instead that 0.3% by weight of the compound (P-J-1) was added in Example 7.

transparent pixel electrode driven with an active element and does not include an alignment film were prepared. The liquid crystal composition was added dropwise on the first substrate, and interposed on the second substrate, the sealing material was cured at normal pressure under condition at 110° C. for 2 hours, and a liquid crystal cell having a cell gap 3.2 μm was obtained. The vertical alignment and alignment unevenness such as dropping marks in this case were observed with a polarization microscope, and evaluated with four levels shown below.

A: Evenly vertically aligned over the entire surface including the end portions and the like.

[Chem. 134]

(Ref-1)

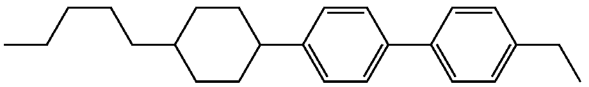

(Ref-2)

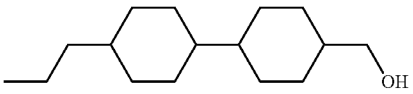

(Ref-3)

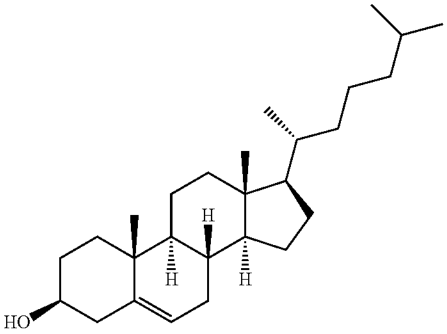

(Ref-4)

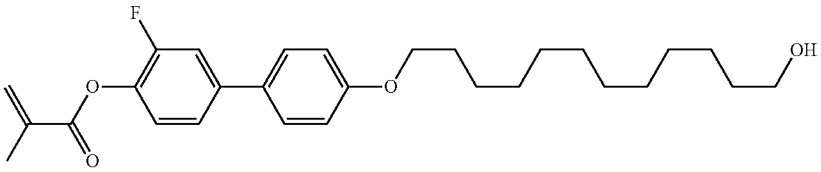

Regarding each liquid crystal composition of the examples and the comparative examples, the following evaluation tests were performed. The result of each evaluation test of each liquid crystal composition was shown in Table 2, Table 4, Table 6, Table 8, Table 10, and Table 12.

(Evaluation Test of Low-Temperature Stability)

The liquid crystal composition was filtered with a membrane filter (PTFE 13 mm-0.2 μm manufactured by Agilent Technologies), and left for 15 minutes under vacuum reduced pressure condition, and the removal of dissolved air was performed. This was washed with acetone, and 0.5 g thereof was weighed on a sufficiently dried vial, and left under a low temperature environment at −25° C. for 10 days. After that, the precipitate was visually observed and determined with two levels shown below.

A: Precipitate cannot be observed.

B: Precipitate can be observed.

(Evaluation Test 1 of Vertical Alignment)

A first substrate (common electrode substrate) which includes a transparent electrode layer formed of a transparent common electrode and a color filter and does not include an alignment film, and a second substrate (pixel electrode substrate) which includes a pixel electrode layer including a B: Extremely slight alignment defect is obtained, but in an acceptable level.

C: A large number of alignment defect including the end portions and the like, and in an unacceptable level.

D: Alignment defect is significantly deteriorated.

(Evaluation Test of Pretilt Angle Formation)

While applying a rectangular AC wave at 10 V and 100 Hz to a liquid crystal cell used in the section of (Evaluation Test of Vertical Alignment), a UV light having illuminance of 100 $m/cm^2$ at 365 nm was emitted for 200 seconds using a high pressure mercury lamp. After that, regarding the stability of white display, a physical external force was applied to the cell while applying the rectangular AC wave at 10 V and 100 Hz, the observation was performed in a crossed Nichol prism state, and evaluation was performed with four levels shown below.

A: Evenly vertically aligned over the entire surface including the end portions and the like.

B: Extremely slight alignment defect is obtained, but in an acceptable level.

C: A large number of alignment defect including the end portions and the like, and in an unacceptable level.

D: Alignment defect is significantly deteriorated.

(Evaluation Test of Remaining Monomer Amount)

The amount of the polymerizable compound (R1-1-1), after irradiating the cell used in the section of (Evaluation Test of Pretilt Angle Formation) with light of a UV fluorescent lamp manufactured by Toshiba Lighting and Technology Corporation for 60 minutes (illuminance of 1.7 $mW/cm^2$ at 313 nm), was determined with HPLC, and the amount of the remaining monomer was determined. The evaluation was performed with four levels shown below, in accordance with the amount of the remaining monomer.

A: less than 300 ppm

B: equal to or greater than 300 ppm and less than 500 ppm

C: equal to or greater than 500 ppm and less than 1,500 ppm

D: equal to or greater than 1,500 ppm (Evaluation Test of Response Properties)

The cell having a cell gap of 3.2 μm used in the section of (Evaluation Test of Pretilt Angle Formation) was irradiated with light of a UV fluorescent lamp manufactured by Toshiba Lighting and Technology Corporation for 60 minutes (illuminance of 1.7 $mW/cm^2$ at 313 nm). The response speed was measured with respect to the cell obtained as described above. Regarding the response speed, Voff at 6 V was measured using DMS 703 manufactured by AUTRONIC-MELCHERS under the temperature condition of 25° C. The response properties were evaluated with four levels shown below.

A: less than 5 ms

B: equal to or greater than 5 ms and less than 15 ms

C: equal to or greater than 15 ms and less than 25 ms

D: equal to or greater than 25 ms

TABLE 1

| | Base LC | % by mass | Additive compound | Added amount (% by mass) |
|---|---|---|---|---|
| Example 7 | LC-1 | 100 | (P-J-1) | 0.3 |
| Example 8 | LC-1 | 100 | (P-J-1) | 0.5 |
| Example 9 | LC-1 | 100 | (P-J-1) | 1.0 |
| Example 10 | LC-1 | 100 | (P-J-1) | 1.5 |
| Example 11 | LC-1 | 100 | (P-J-1) | 2.0 |
| Example 12 | LC-1 | 100 | (P-J-1) | 3.0 |
| Example 13 | LC-1 | 100 | (P-J-2) | 0.2 |
| Example 14 | LC-1 | 100 | (P-J-2) | 0.3 |
| Example 15 | LC-1 | 100 | (P-J-2) | 0.5 |
| Example 16 | LC-1 | 100 | (P-J-3) | 1.0 |
| Example 17 | LC-1 | 100 | (P-J-4) | 1.0 |
| Example 18 | LC-1 | 100 | (P-J-5) | 1.0 |
| Example 19 | LC-1 | 100 | (P-J-5) | 3.0 |
| Example 20 | LC-1 | 100 | (P-J-6) | 1.0 |
| Example 21 | LC-1 | 100 | (P-J-6) | 3.0 |
| Example 22 | LC-1 | 100 | (P-J-7) | 1.0 |
| Example 23 | LC-1 | 100 | (P-J-8) | 1.0 |
| Example 24 | LC-1 | 100 | (P-J-9) | 1.0 |
| Example 25 | LC-2 | 100 | (P-J-1) | 0.3 |
| Example 26 | LC-2 | 100 | (P-J-1) | 0.5 |
| Example 27 | LC-2 | 100 | (P-J-1) | 1.5 |
| Example 28 | LC-2 | 100 | (P-J-1) | 2.0 |
| Example 29 | LC-2 | 100 | (P-J-1) | 3.0 |

TABLE 2

| | Low-temperature storage stability | Vertical alignment | Pretilt angle formation | Amount of remaining monomer | Response properties |
|---|---|---|---|---|---|
| Example 7 | A | B | A | A | A |
| Example 8 | A | B | A | A | A |
| Example 9 | A | A | A | A | A |
| Example 10 | A | A | A | A | A |

TABLE 2-continued

| | Low-temperature storage stability | Vertical alignment | Pretilt angle formation | Amount of remaining monomer | Response properties |
|---|---|---|---|---|---|
| Example 11 | A | A | A | B | A |
| Example 12 | A | A | A | B | A |
| Example 13 | A | B | A | A | B |
| Example 14 | A | A | A | A | B |
| Example 15 | A | A | A | B | B |
| Example 16 | A | A | A | A | A |
| Example 17 | A | A | A | B | B |
| Example 18 | A | B | A | A | A |
| Example 19 | A | A | A | B | B |
| Example 20 | A | B | A | A | A |
| Example 21 | A | A | A | B | B |
| Example 22 | A | A | A | B | B |
| Example 23 | A | A | A | B | B |
| Example 24 | A | B | A | B | B |
| Example 25 | A | B | A | A | A |
| Example 26 | A | B | A | A | A |
| Example 27 | A | A | A | A | A |
| Example 28 | A | A | A | B | A |
| Example 29 | A | A | A | B | A |

TABLE 3

| | Base LC | % by mass | Additive compound | Added amount (% by mass) |
|---|---|---|---|---|
| Example 30 | LC-2 | 100 | (P-J-2) | 0.2 |
| Example 31 | LC-2 | 100 | (P-J-2) | 0.3 |
| Example 32 | LC-2 | 100 | (P-J-2) | 0.5 |
| Example 33 | LC-2 | 100 | (P-J-3) | 1.5 |
| Example 34 | LC-2 | 100 | (P-J-4) | 1.5 |
| Example 35 | LC-2 | 100 | (P-J-5) | 1.5 |
| Example 36 | LC-2 | 100 | (P-J-5) | 3.0 |
| Example 37 | LC-2 | 100 | (P-J-6) | 1.5 |
| Example 38 | LC-2 | 100 | (P-J-6) | 3.0 |
| Example 39 | LC-2 | 100 | (P-J-7) | 1.5 |
| Example 40 | LC-2 | 100 | (P-J-8) | 1.5 |
| Example 41 | LC-2 | 100 | (P-J-9) | 1.5 |
| Example 42 | LC-1 | 100 | (P-J-10) | 0.5 |
| Example 43 | LC-1 | 100 | (P-J-11) | 0.5 |
| Example 44 | LC-1 | 100 | (P-J-12) | 0.5 |
| Example 45 | LC-1 | 100 | (P-J-13) | 0.5 |
| Example 46 | LC-1 | 100 | (P-J-14) | 0.5 |
| Example 47 | LC-1 | 100 | (P-J-15) | 0.5 |
| Example 48 | LC-1 | 100 | (P-J-16) | 0.5 |
| Example 49 | LC-1 | 100 | (P-J-17) | 0.5 |
| Example 50 | LC-1 | 100 | (P-J-18) | 0.5 |
| Example 51 | LC-1 | 100 | (P-J-19) | 0.5 |
| Example 52 | LC-1 | 100 | (P-J-20) | 0.5 |
| Example 53 | LC-1 | 100 | (P-J-21) | 0.5 |
| Example 54 | LC-1 | 100 | (P-J-22) | 0.5 |
| Example 55 | LC-1 | 100 | (P-J-23) | 0.5 |
| Example 56 | LC-1 | 100 | (P-J-24) | 0.5 |

TABLE 4

| | Low-temperature storage stability | Vertical alignment | Pretilt angle formation | Amount of Remaining monomer | Response properties |
|---|---|---|---|---|---|
| Example 30 | A | B | A | A | B |
| Example 31 | A | A | A | A | B |
| Example 32 | A | A | A | B | B |
| Example 33 | A | A | A | A | A |
| Example 34 | A | A | A | B | B |
| Example 35 | A | B | A | A | A |
| Example 36 | A | A | A | B | B |
| Example 37 | A | B | A | A | A |
| Example 38 | A | A | A | B | B |
| Example 39 | A | A | A | B | B |

TABLE 4-continued

| | Low-temperature storage stability | Vertical alignment | Pretilt angle formation | Amount of Remaining monomer | Response properties |
|---|---|---|---|---|---|
| Example 40 | A | A | A | B | B |
| Example 41 | A | B | A | B | B |
| Example 42 | A | B | A | A | A |
| Example 43 | A | B | A | A | A |
| Example 44 | A | A | A | A | A |
| Example 45 | A | B | A | A | A |
| Example 46 | A | A | A | B | B |
| Example 47 | A | B | A | A | A |
| Example 48 | A | B | A | A | A |
| Example 49 | A | A | A | A | A |
| Example 50 | A | A | A | A | A |
| Example 51 | A | A | A | A | A |
| Example 52 | A | B | A | A | A |
| Example 53 | A | B | A | A | A |
| Example 54 | A | B | A | A | A |
| Example 55 | A | A | A | A | A |
| Example 56 | A | B | A | A | A |

TABLE 5

| | Base LC | % by mass | Additive compound | Added amount (% by mass) |
|---|---|---|---|---|
| Example 57 | LC-1 | 100 | (P-J-25) | 0.5 |
| Example 58 | LC-1 | 100 | (P-J-26) | 0.5 |
| Example 59 | LC-1 | 100 | (P-J-27) | 0.5 |
| Example 60 | LC-1 | 100 | (P-J-28) | 0.5 |
| Example 61 | LC-1 | 100 | (P-J-29) | 0.5 |
| Example 62 | LC-1 | 100 | (P-J-30) | 0.5 |
| Example 63 | LC-1 | 100 | (P-J-31) | 0.5 |
| Example 64 | LC-1 | 100 | (P-J-32) | 0.5 |
| Example 65 | LC-1 | 100 | (P-J-33) | 0.5 |
| Example 66 | LC-1 | 100 | (P-J-34) | 0.5 |
| Example 67 | LC-1 | 100 | (P-J-35) | 0.5 |
| Example 68 | LC-1 | 100 | (P-J-36) | 0.5 |
| Example 69 | LC-1 | 100 | (P-J-37) | 0.5 |
| Example 70 | LC-1 | 100 | (P-J-38) | 0.5 |
| Example 71 | LC-1 | 100 | (P-J-39) | 0.5 |
| Example 72 | LC-1 | 100 | (P-J-40) | 0.5 |
| Example 73 | LC-1 | 100 | (P-J-41) | 0.5 |
| Example 74 | LC-1 | 100 | (P-J-42) | 0.5 |
| Example 75 | LC-1 | 100 | (P-J-43) | 0.5 |
| Example 76 | LC-1 | 100 | (P-J-44) | 0.5 |
| Example 77 | LC-1 | 100 | (P-J-45) | 0.5 |
| Example 78 | LC-1 | 100 | (P-J-46) | 0.5 |
| Example 79 | LC-1 | 100 | (P-J-47) | 0.5 |
| Example 80 | LC-1 | 100 | (P-J-48) | 0.5 |
| Example 81 | LC-1 | 100 | (P-J-49) | 0.5 |
| Example 82 | LC-1 | 100 | (P-J-50) | 0.5 |
| Example 83 | LC-1 | 100 | (P-J-51) | 0.5 |

TABLE 6

| | Low-temperature storage stability | Vertical alignment | Pretilt angle formation | Amount of Remaining monomer | Response properties |
|---|---|---|---|---|---|
| Example 57 | A | B | A | A | A |
| Example 58 | A | A | A | B | B |
| Example 59 | A | A | A | A | A |
| Example 60 | A | A | A | A | A |
| Example 61 | A | A | A | B | B |
| Example 62 | A | A | A | A | A |
| Example 63 | A | A | A | A | A |
| Example 64 | A | A | A | A | A |
| Example 65 | A | A | A | A | A |
| Example 66 | A | A | A | A | A |
| Example 67 | A | B | A | A | A |
| Example 68 | A | A | B | A | A |

TABLE 6-continued

| | Low-temperature storage stability | Vertical alignment | Pretilt angle formation | Amount of Remaining monomer | Response properties |
|---|---|---|---|---|---|
| Example 69 | A | A | A | A | A |
| Example 70 | A | A | B | A | A |
| Example 71 | A | A | A | A | A |
| Example 72 | A | A | A | B | B |
| Example 73 | A | A | A | A | A |
| Example 74 | A | A | A | A | A |
| Example 75 | A | A | A | A | A |
| Example 76 | A | A | A | B | B |
| Example 77 | A | A | A | B | B |
| Example 78 | A | A | A | A | A |
| Example 79 | A | A | A | A | A |
| Example 80 | A | A | A | A | A |
| Example 81 | A | A | A | B | B |
| Example 82 | A | A | B | A | A |
| Example 83 | A | B | B | B | B |

TABLE 7

| | Base LC | % by mass | Additive compound | Added amount (% by mass) |
|---|---|---|---|---|
| Example 84 | LC-1 | 100 | (P-J-52) | 0.5 |
| Example 85 | LC-1 | 100 | (P-J-53) | 0.5 |
| Example 86 | LC-1 | 100 | (P-J-54) | 0.5 |
| Example 87 | LC-1 | 100 | (P-J-55) | 0.5 |
| Example 88 | LC-1 | 100 | (P-J-56) | 0.5 |
| Example 89 | LC-1 | 100 | (P-J-57) | 0.5 |
| Example 90 | LC-1 | 100 | (P-J-10) | 1.2 |
| Example 91 | LC-1 | 100 | (P-J-11) | 1.2 |
| Example 92 | LC-1 | 100 | (P-J-12) | 1.2 |
| Example 93 | LC-1 | 100 | (P-J-13) | 1.2 |
| Example 94 | LC-1 | 100 | (P-J-14) | 1.2 |
| Example 95 | LC-1 | 100 | (P-J-15) | 1.2 |
| Example 96 | LC-1 | 100 | (P-J-16) | 1.2 |
| Example 97 | LC-1 | 100 | (P-J-17) | 1.2 |
| Example 98 | LC-1 | 100 | (P-J-18) | 1.2 |
| Example 99 | LC-1 | 100 | (P-J-19) | 1.2 |
| Example 100 | LC-1 | 100 | (P-J-20) | 1.2 |
| Example 101 | LC-1 | 100 | (P-J-21) | 1.2 |
| Example 102 | LC-1 | 100 | (P-J-22) | 1.2 |
| Example 103 | LC-1 | 100 | (P-J-23) | 1.2 |
| Example 104 | LC-1 | 100 | (P-J-24) | 1.2 |
| Example 105 | LC-1 | 100 | (P-J-25) | 1.2 |
| Example 106 | LC-1 | 100 | (P-J-26) | 1.2 |
| Example 107 | LC-1 | 100 | (P-J-27) | 1.2 |
| Example 108 | LC-1 | 100 | (P-J-28) | 1.2 |

TABLE 8

| | Low-temperature storage stability | Vertical alignment | Pretilt angle formation | Amount of Remaining monomer | Response properties |
|---|---|---|---|---|---|
| Example 84 | A | B | B | B | B |
| Example 85 | A | B | B | B | B |
| Example 86 | A | B | B | B | B |
| Example 87 | A | B | B | B | B |
| Example 88 | A | B | B | B | B |
| Example 89 | A | B | B | B | B |
| Example 90 | A | B | A | A | A |
| Example 91 | A | B | A | A | A |
| Example 92 | A | A | A | A | A |
| Example 93 | A | B | A | A | A |
| Example 94 | A | A | A | B | B |
| Example 95 | A | B | A | A | A |
| Example 96 | A | B | A | A | A |
| Example 97 | A | A | A | A | A |
| Example 98 | A | A | A | A | A |
| Example 99 | A | A | A | A | A |

TABLE 8-continued

| | Low-temperature storage stability | Vertical alignment | Pretilt angle formation | Amount of Remaining monomer | Response properties |
|---|---|---|---|---|---|
| Example 100 | A | B | A | A | A |
| Example 101 | A | B | A | A | A |
| Example 102 | A | B | A | A | A |
| Example 103 | A | A | A | A | A |
| Example 104 | A | B | A | A | A |
| Example 105 | A | B | A | A | A |
| Example 106 | A | A | A | B | B |
| Example 107 | A | A | A | A | A |
| Example 108 | A | A | A | A | A |

TABLE 9

| | Base LC | % by mass | Additive compound | Added amount (% by mass) |
|---|---|---|---|---|
| Example 109 | LC-1 | 100 | (P-J-29) | 1.2 |
| Example 110 | LC-1 | 100 | (P-J-30) | 1.2 |
| Example 111 | LC-1 | 100 | (P-J-31) | 1.2 |
| Example 112 | LC-1 | 100 | (P-J-32) | 1.2 |
| Example 113 | LC-1 | 100 | (P-J-33) | 1.2 |
| Example 114 | LC-1 | 100 | (P-J-34) | 1.2 |
| Example 115 | LC-1 | 100 | (P-J-35) | 1.2 |
| Example 116 | LC-1 | 100 | (P-J-36) | 1.2 |
| Example 117 | LC-1 | 100 | (P-J-37) | 1.2 |
| Example 118 | LC-1 | 100 | (P-J-38) | 1.2 |
| Example 119 | LC-1 | 100 | (P-J-39) | 1.2 |
| Example 120 | LC-1 | 100 | (P-J-40) | 1.2 |
| Example 121 | LC-1 | 100 | (P-J-41) | 1.2 |
| Example 122 | LC-1 | 100 | (P-J-42) | 1.2 |
| Example 123 | LC-1 | 100 | (P-J-43) | 1.2 |
| Example 124 | LC-1 | 100 | (P-J-44) | 1.2 |
| Example 125 | LC-1 | 100 | (P-J-45) | 1.2 |
| Example 126 | LC-1 | 100 | (P-J-46) | 1.2 |
| Example 127 | LC-1 | 100 | (P-J-47) | 1.2 |
| Example 128 | LC-1 | 100 | (P-J-48) | 1.2 |
| Example 129 | LC-1 | 100 | (P-J-49) | 1.2 |
| Example 130 | LC-1 | 100 | (P-J-50) | 1.2 |
| Example 131 | LC-1 | 100 | (P-J-51) | 1.2 |
| Example 132 | LC-1 | 100 | (P-J-52) | 1.2 |
| Example 133 | LC-1 | 100 | (P-J-53) | 1.2 |
| Example 134 | LC-1 | 100 | (P-J-54) | 1.2 |

TABLE 9-continued

| | Base LC | % by mass | Additive compound | Added amount (% by mass) |
|---|---|---|---|---|
| Example 135 | LC-1 | 100 | (P-J-55) | 1.2 |
| Example 136 | LC-1 | 100 | (P-J-56) | 1.2 |
| Example 137 | LC-1 | 100 | (P-J-57) | 1.2 |

TABLE 10

| | Low-temperature storage stability | Vertical alignment | Pretilt angle formation | Amount of Remaining monomer | Response properties |
|---|---|---|---|---|---|
| Example 109 | A | A | A | B | B |
| Example 110 | A | A | A | A | A |
| Example 111 | A | A | A | A | A |
| Example 112 | A | A | A | A | A |
| Example 113 | A | A | A | A | A |
| Example 114 | A | A | A | A | A |
| Example 115 | A | B | A | A | A |
| Example 116 | A | A | B | A | A |
| Example 117 | A | A | A | A | A |
| Example 118 | A | A | B | A | A |
| Example 119 | A | A | A | A | A |
| Example 120 | A | A | A | B | B |
| Example 121 | A | A | A | A | A |
| Example 122 | A | A | A | A | A |
| Example 123 | A | A | A | A | A |
| Example 124 | A | A | A | B | B |
| Example 125 | A | A | A | B | B |
| Example 126 | A | A | A | A | A |
| Example 127 | A | A | A | A | A |
| Example 128 | A | A | A | A | A |
| Example 129 | A | A | A | B | B |
| Example 130 | A | A | B | A | A |
| Example 131 | A | A | B | B | B |
| Example 132 | A | A | B | B | B |
| Example 133 | A | A | B | B | B |
| Example 134 | A | A | B | B | B |
| Example 135 | A | A | B | B | B |
| Example 136 | A | A | B | B | B |
| Example 137 | A | A | B | B | B |

TABLE 11

| | Base LC | % by mass | Additive compound 1 | Added amount (% by mass) | Additive compound 2 | Added amount (% by mass) |
|---|---|---|---|---|---|---|
| Example 138 | LC-1 | 100 | P-J-12 | 0.5 | P-J-19 | 0.5 |
| Example 139 | LC-1 | 100 | P-J-12 | 0.5 | P-J-19 | 1.0 |
| Example 140 | LC-1 | 100 | P-J-12 | 1.0 | P-J-19 | 1.0 |
| Example 141 | LC-1 | 100 | P-J-19 | 0.5 | P-J-23 | 0.5 |
| Example 142 | LC-1 | 100 | P-J-19 | 0.5 | P-J-23 | 1.0 |
| Example 143 | LC-1 | 100 | P-J-19 | 1.0 | P-J-23 | 1.0 |
| Example 144 | LC-1 | 100 | P-J-19 | 0.5 | P-J-39 | 1.0 |
| Example 145 | LC-1 | 100 | P-J-19 | 1.0 | P-J-39 | 1.0 |
| Example 146 | LC-1 | 100 | P-J-19 | 0.5 | P-J-42 | 1.0 |
| Example 147 | LC-1 | 100 | P-J-19 | 1.0 | P-J-42 | 1.0 |
| Example 148 | LC-1 | 100 | P-J-19 | 0.5 | P-J-46 | 1.0 |
| Example 149 | LC-1 | 100 | P-J-19 | 1.0 | P-J-46 | 1.0 |
| Example 150 | LC-1 | 100 | P-J-19 | 0.5 | P-J-51 | 1.0 |
| Example 151 | LC-1 | 100 | P-J-19 | 1.0 | P-J-51 | 1.0 |

TABLE 12

| | Low-temperature storage stability | Vertical alignment | Pretilt angle Formation | Amount of remaining monomer | Response properties |
|---|---|---|---|---|---|
| Example 138 | A | A | A | A | A |
| Example 139 | A | A | A | A | A |
| Example 140 | A | A | A | A | A |
| Example 141 | A | A | A | A | A |
| Example 142 | A | A | A | A | A |
| Example 143 | A | A | A | A | A |
| Example 144 | A | A | A | A | A |
| Example 145 | A | A | A | A | A |
| Example 146 | A | A | A | A | A |
| Example 147 | A | A | A | A | A |
| Example 148 | A | A | A | A | A |
| Example 149 | A | A | A | A | A |
| Example 150 | A | A | B | B | B |
| Example 151 | A | A | B | B | B |

TABLE 13

| | Base LC | % by mass | Additive compound | Added amount (% by mass) |
|---|---|---|---|---|
| Comparative Example 1 | LC-1 | 100 | — | — |
| Comparative Example 2 | LC-1 | 100 | Ref-1 | 1.0 |
| Comparative Example 3 | LC-1 | 100 | Ref-1 | 3.0 |
| Comparative Example 4 | LC-1 | 100 | Ref-2 | 1.0 |
| Comparative Example 5 | LC-1 | 100 | Ref-2 | 3.0 |
| Comparative Example 6 | LC-1 | 100 | Ref-3 | 1.0 |
| Comparative Example 7 | LC-1 | 100 | Ref-3 | 3.0 |
| Comparative Example 8 | LC-2 | 100 | — | — |
| Comparative Example 9 | LC-2 | 100 | Ref-1 | 1.0 |
| Comparative Example 10 | LC-2 | 100 | Ref-2 | 1.0 |
| Comparative Example 11 | LC-2 | 100 | Ref-3 | 1.0 |

TABLE 14

| | Low-temperature storage stability | Vertical alignment | Pretilt angle Formation | Monomer of remaining monomer | Response properties |
|---|---|---|---|---|---|
| Comparative Example 1 | A | D | — | A | A |
| Comparative Example 2 | A | D | — | A | A |
| Comparative Example 3 | D | D | — | A | A |
| Comparative Example 4 | D | C | C | C | D |
| Comparative Example 5 | D | C | C | D | D |
| Comparative Example 6 | D | C | C | C | D |
| Comparative Example 7 | D | C | C | D | D |
| Comparative Example 8 | A | D | — | A | A |
| Comparative Example 9 | A | D | — | A | A |

TABLE 14-continued

| | Low-temperature storage stability | Vertical alignment | Pretilt angle Formation | Monomer of remaining monomer | Response properties |
|---|---|---|---|---|---|
| Comparative Example 10 | D | C | C | C | D |
| Comparative Example 11 | D | C | C | C | D |

The above results show that the invention brings about advantageous effects.

The invention claimed is:

1. A liquid crystal composition having a negative dielectric anisotropy ($\Delta\varepsilon$) comprising a compound represented by general formula (ii-2):

(ii-2)

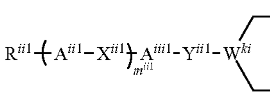

wherein $A^{ii1}$ and $A^{iii1}$ each represent the same meaning as $A^{ii1}$, $m^{ii1}$ represents an integer of 2 to 4, $R^{ii1}$ represents a hydrogen atom, a linear or branched alkyl group having 1 to 40 carbon atoms, a halogenated alkyl group, or $P^{i1}$-$Sp^{i1}$-, wherein $-CH_2-$ in the alkyl group may be replaced with $-CH=CH-$, $-C\equiv C-$, $-O-$, $-NH-$, $-COO-$, or $-OCO-$, provided that $-O-$ moieties are not bonded in series, $W^{ki}$ represents a methine group, $C-CH_3$, or $C-C_2H_5$, $X^{ii1}$ represents a single bond, $-CH=CH-$, $-CF=CF-$, $-C\equiv C-$, $-COO-$, $-OCO-$, $-OCOO-$, $-OOCO-$, $-CF_2O-$, $-OCF_2-$, $-CH=CHCOO-$, $-OCOCH=CH-$, $-CH_2-CH_2COO-$, $-OCOCH_2-CH_2-$, $-CH=C(CH_3)COO-$, $-OCOC(CH_3)=CH-$, $-CH_2-CH(CH_3)COO-$, $-OCOCH(CH_3)-CH_2-$, or $-OCH_2CH_2O-$, provided that at least one $X^{ii1}$ represents $-CH_2-CH_2COO-$, $-OCOCH_2-CH_2-$, $-CH=C(CH_3)COO-$, $-OCOC(CH_3)=CH-$, $-CH_2-CH(CH_3)COO-$, $-OCOCH(CH_3)-CH_2-$, or $-OCH_2CH_2O-$, and $Y^{ii1}$ represents a single bond, $-CH=CH-$, $-CF=CF-$, $-C\equiv C-$, $-COO-$, $-OCO-$, $-OCOO-$, $-OOCO-$, $-CF_2O-$, $-OCF_2-$, $-CH=CHCOO-$, $-OCOCH=CH-$, $-CH_2-CH_2COO-$, $-OCOCH_2-CH_2-$, $-CH=C(CH_3)COO-$, $-OCOC(CH_3)=CH-$, $-CH_2-CH(CH_3)COO-$, $-OCOCH(CH_3)-CH_2-$, or an alkylene group having 2 to 20 carbon atoms, wherein one $-CH_2-$ or two or more $-CH_2-$'s not adjacent to each other in the alkylene group may be replaced with $-O-$, $-COO-$, or $-OCO-$.

2. The liquid crystal composition according to claim 1, further comprising a compound selected from the group consisting of compounds represented by general formulae (N-1), (N-2), and (N-3):

(N-1)

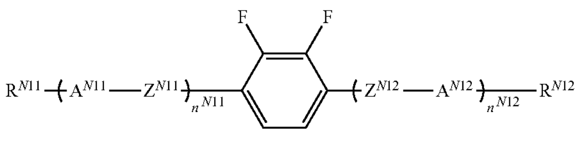

-continued (N-2)

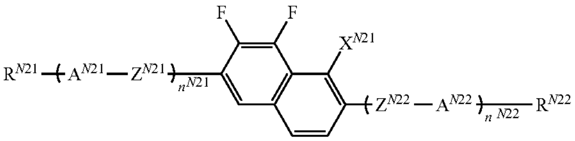

(N-3)

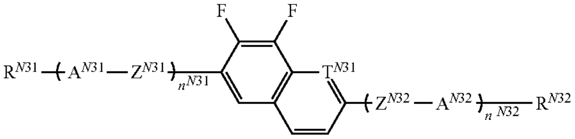

wherein $R^{N11}$, $R^{N12}$, $R^{N21}$, $R^{N22}$, $R^{N31}$, and $R^{N32}$ each independently represent an alkyl group having 1 to 8 carbon atoms, wherein one $—CH_2—$ or two or more $—CH_2—$'s not adjacent to each other in the alkyl group each may be independently replaced with —CH═CH—, —C≡C—, —O—, —CO—, —COO—, or —OCO—, $A^{N11}$, $A^{N12}$, $A^{N21}$, $A^{N22}$, $A^{N31}$, and $A^{N32}$ each independently represent a group selected from the group consisting of (a) a 1,4-cyclohexylene group, wherein one $—CH_2—$ or two or more $—CH_2—$'s not adjacent to each other in this group may be replaced with 0-, (b) a 1,4-phenylene group, wherein one —CH═ or two or more —CH═'s not adjacent to each other in this group may be replaced with —N═, (c) a naphthalene-2,6-diyl group, a 1,2,3,4-tetrahydronaphthalene-2,6-diyl group, or a decahydronaphthalene-2,6-diyl group, wherein one —CH═ or two or more —CH═'s not adjacent to each other in the naphthalene-2,6-diyl group or the 1,2,3,4-tetrahydronaphthalene-2,6-diyl group may be replaced with —N═, and (d) a 1,4-cyclohexenylene group, wherein the group (a), the group (b), the group (c), and the group (d) each may be independently substituted with a cyano group, a fluorine atom, or a chlorine atom, $Z^{N11}$, $Z^{N12}$, $Z^{N21}$, $Z^{N22}$, $Z^{N31}$, and $Z^{N32}$ each independently represent a single bond, $—CH_2CH_2—$, $—(CH_2)_4—$, $—OCH_2—$, $—CH_2O—$, —COO—, —OCO—, $—OCF_2—$, $—CF_2O—$, —CH═N—N═CH—, —CH═CH—, —CF═CF—, or —C≡C—, $X^{N21}$ represents a hydrogen atom or a fluorine atom, $T^{N31}$ represents $—CH_2—$ or an oxygen atom, $n^{N11}$, $n^{N12}$, $n^{N21}$, $n^{N22}$, $n^{N31}$, and $n^{N32}$ each independently represent an integer of 0 to 3, provided that $n^{N11}+n^{N12}$, $n^{N21}+n^{N22}$, and $n^{N31}+n^{N32}$ are each independently 1, 2, or 3, two or more occurrences of one of $A^{N11}$'s to $A^{N32}$'s and $Z^{N11}$'s to $Z^{N32}$'s may be the same or different.

3. The liquid crystal composition according to claim 1, further comprising:

a compound represented by general formula (L):

$$R^{L1}—A^{L1}—Z^{L1}—(A^{L2}—Z^{L2})_{nL1}—A^{L3}—R^{L2} \quad \text{(L)}$$

wherein $R^{L1}$ and $R^{L2}$ each independently represent an alkyl group having 1 to 8 carbon atoms, wherein one $—CH_2—$ or two or more $—CH_2—$'s not adjacent to each other in the alkyl group each may be independently replaced with —CH═CH—, —C≡C—, —O—, —CO—, —COO—, or —OCO—, $n^{L1}$ represents 0, 1, 2, or 3, $A^{L1}$, $A^{L2}$, and $A^{L3}$ each independently represent a group selected from the group consisting of (a) a 1,4-cyclohexylene group, wherein one $—CH_2—$ or two or more $—CH_2—$'s not adjacent to each other in this group may be replaced with —O—, (b) a 1,4-phenylene group, wherein one —CH═ or two or more —CH═'s not adjacent to each other in this group may be replaced with —N═, and (c) a naphthalene-2,6-diyl group, a 1,2,3,4-tetrahydronaphthalene-2,6-diyl group, or a decahydronaphthalene-2,6-diyl group, wherein one —CH═ or two or more —CH═'s not adjacent to each other in the naphthalene-2,6-diyl group or the 1,2,3,4-tetrahydronaphthalene-2,6-diyl group may be replaced with —N═, wherein the group (a), the group (b), and the group (c) each may be independently substituted with a cyano group, a fluorine atom, or a chlorine atom, $Z^{L1}$ and $Z^{L2}$ each independently represent a single bond, $—CH_2CH_2—$, $—(CH_2)_4—$, $—OCH_2—$, $—CH_2O—$, —COO—, —OCO—, $—OCF_2—$, $—CF_2O—$, —CH═N—N═CH—, —CH═CH—, —CF═CF—, or —C≡C—, when $n^{L1}$ is 2 or 3 and a plurality of $A^{L2}$'s are present, these may be the same or different, and when $n^{L1}$ is 2 or 3 and a plurality of $Z^{L2}$'s are present, these may be the same or different, exclusive of compounds represented by general formulae (N-1), (N-2), and (N-3).

4. The liquid crystal composition according to claim 1, further comprising:

at least one polymerizable compound.

5. The liquid crystal composition according to claim 4, wherein the at least one polymerizable compound includes one or more compounds represented by general formula (P):

$$(R^{p1}—Sp^{p1})_{mp1}—(M^{p1})_{mp2}—(L^{p1}—M^{p2})_{mp3}—(L^{p2}—M^{p3})_{mp4}—(Z^{p1})_{mp5} \quad \text{(P)}$$

wherein $Z^{p1}$ represents a fluorine atom, a cyano group, a hydrogen atom, an alkyl group having 1 to 15 carbon atoms in which a hydrogen atom may be replaced with a halogen atom, an alkoxy group having 1 to 15 carbon atoms in which a hydrogen atom may be replaced with a halogen atom, an alkenyl group having 1 to 15 carbon atoms in which a hydrogen atom may be replaced with a halogen atom, an alkenyloxy group having 1 to 15 carbon atoms in which a hydrogen atom may be replaced with a halogen atom, or $-SP^{p2}-R^{p2}$, $R^{P1}$ and $R^{P2}$ each represent one of formula (R-I) to formula (R-IX):

(R-I)

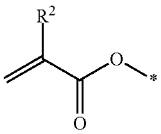

-continued (R-II)

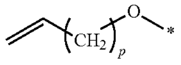

(R-III)

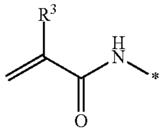

(R-IV)

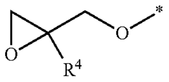

(R-V)

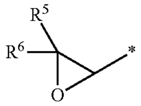

(R-VI)

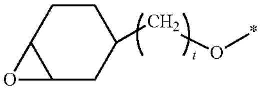

(R-VII)

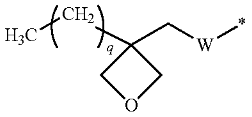

(R-VIII)

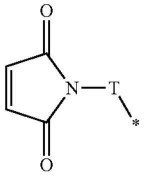

(R-IX)

HS—* wherein $Sp^{P1}$ and $Sp^{P2}$ is bonded at a position marked by *, $R^2$ to $R^6$ each independently represent a hydrogen atom, an alkyl group having 1 to 5 carbon atoms, or a halogenated alkyl group having 1 to 5 carbon atoms, W represents a single bond, —O—, or a methylene group, T represents a single bond or —COO—, p, t, and q each independently represent 0, 1, or 2, $Sp^{P1}$ and $Sp^{P2}$ each represent a spacer group, $L^{P1}$ and $L^{P2}$ each independently represent a single bond, —O—, —S—, $—CH_2—$, $—OCH_2—$, $—CH_2O—$, —CO—, $—C_2H_4—$, —COO—, —OCO—, $—OCOOCH_2—$, $—CH_2OCOO—$, $—OCH_2CH_2O—$, $—CO—NR^a—$, $—NR^a—CO—$, $—SCH_2—$, $—CH_2S—$, $—CH═CR^a—COO—$, $—CH═CR^a—OCO—$, $—COO—CR^a═CH—$, $—OCO—CR^a═CH—$, $—COO—CR^a═CH—COO—$, $—COO—CR^a═CH—OCO—$, $—OCO—CR^a═CH—COO—$, $—OCO—CR^a═CH—OCO—$, $—(CH_2)_z—C(═O)—O—$, $—(CH_2)_z—O—(C═O)—$, $—O—(C═O)—(CH_2)_z—$, $—(C═O)—O—(CH_2)_z—$, $—CH_2(CH_3)C—C(═O)—O—$, $—CH_2(CH_3)C—O—(C═O)—$, $—O—(C═O)—C(CH_3)CH_2$, $—(C═O)—O—C(CH_3)—CH_2$, —CH═CH—, —CF═CF—, —CF═CH—, —CH═CF—, $—CF_2—$, $—CF_2O—$, $—OCF_2—$, $—CF_2CH_2—$, $—CH_2CF_2—$, $—CF_2CF_2—$, or —C≡C—, wherein $R^a$'s each independently represent a hydrogen atom or an alkyl group having 1 to 4 carbon atoms, and z represents an integer of 1 to 4, $M^{P2}$ represents a 1,4-phenylene group, a 1,4-cyclohexylene group, anthracene-2,6-diyl group, a phenanthrene-2,7-diyl group, a pyridine-2,5-diyl group, a pyrimidine-2,5-diyl group, a naphthalene-2,6-diyl group, an indane-2,5-diyl group, a 1,2,3,4-tetrahydronaphthalene-2,6-diyl group, a 1,3-dioxane-2,5-diyl group, or a single bond, $M^{P2}$ may be unsubstituted or substituted with an alkyl group having 1 to 12 carbon atoms, a halogenated alkyl group having 1 to 12 carbon atoms, an alkoxy group having 1 to 12 carbon atoms, a halogenated alkoxy group having 1 to 12 carbon atoms, a halogen atom, a cyano group, a nitro group, or $—R^{P1}$, $M^{P1}$ represents one of the following formulae (i-11) to (ix-11):

(i-11)

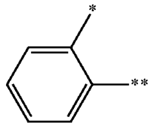

(ii-11)

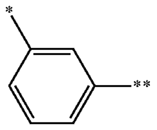

(iii-11)

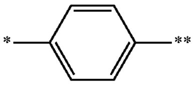

(iv-11)

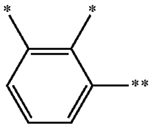

(v-11)

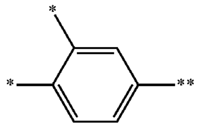

(vi-11)

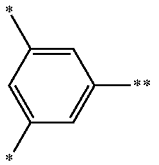

(vii-11)

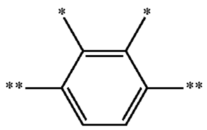

(viii-11)

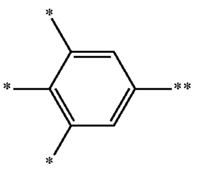

-continued (ix-11)

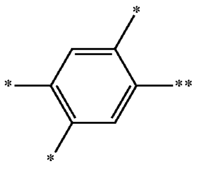

wherein $SP^{P1}$ is bonded at a position marked by *, and $L^{P1}$, $L^{P2}$, or $Z^{P1}$ is bonded at a position marked by **, $M^{P3}$ represents one of formulae (i-13) to (ix-13):

(i-13)

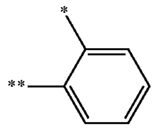

(iv-13)

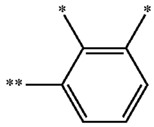

(vii-13)

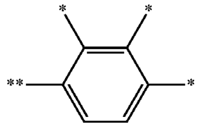

(ii-13)

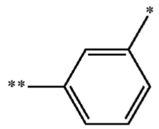

(v-13)

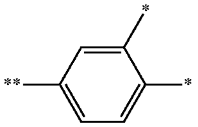

(viii-13)

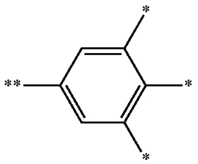

(iii-13)

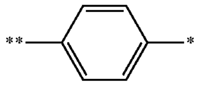

(vi-13)

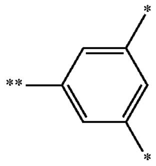

-continued (ix-13)

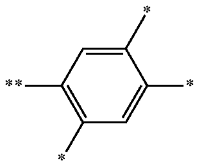

wherein $Z^{P1}$ is bonded at a position marked by *, and $L^{P2}$ is bonded at a position marked by **, $m^{P2}$ to $m^{P4}$ each independently represent 0, 1, 2, or 3, $m^{P1}$ and $m^{P5}$ each independently represent 1, 2, or 3, when a plurality of $Z^{P1}$'s are present, these may be the same or different, when a plurality of $R^{P1}$'s are present, these may be the same or different, when a plurality of $R^{P2}$'s are present, these may be the same or different, when a plurality of $Sp^{P1}$'s are present, these may be the same or different, when a plurality of $Sp^{P2}$'s are present, these may be the same or different, when a plurality of $L^{P1}$'s are present, these may be the same or different, and when a plurality of $M^{P2}$'s are present, these may be the same or different.

6. A liquid crystal display element comprising:

two substrates; and a liquid crystal layer including the liquid crystal composition according to claim 1 provided between the two substrates.

7. A liquid crystal display element comprising:

two substrates; and a liquid crystal layer including the liquid crystal composition according to claim 1 in which the compound represented by general formula (ii-2) has been polymerized.

8. The liquid crystal display element according to claim 6, which is for active matrix driving.

9. The liquid crystal display element according to claim 6, which is a PSA type, PSVA type, VA type, IPS type, FFS type, or ECB type.

10. The liquid crystal display element according to claim 6, wherein at least one of the two substrates is not provided with any alignment film.

11. A spontaneous orientation aid for a liquid crystal composition, comprising a compound represented by general formula (ii-2):

(ii-2)

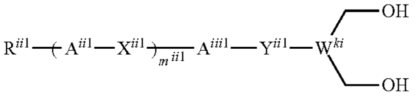

wherein $A^{ii1}$ and $A^{iii1}$ each represent the same meaning as $A^{ii1}$, $m^{ii1}$ represents an integer of 2 to 4, $R^{ii1}$ represents a hydrogen atom, a linear or branched alkyl group having 1 to 40 carbon atoms, a halogenated alkyl group, or wherein $—CH_2—$ in the alkyl group may be replaced with —CH═CH—, —C≡C—, —O—, —NH—, —COO—, or —OCO—, provided that —O— moieties are not bonded in series, $W^{ki}$ represents a methine group, C—$CH_3$, or C—$C_2H_5$, $X^{ii1}$ represents a single bond, —CH═CH—, —CF═CF—, —C≡C—, —COO—, —OCO—, —OCOO—, —OOCO—, —$CF_2O$—, —$OCF_2$—, —CH═CHCOO—, —OCOCH═CH—, —$CH_2$—$CH_2COO$—, —$OCOCH_2$—$CH_2$—, —CH═C($CH_3$)COO—, —OCOC($CH_3$)═CH—, —$CH_2$—CH($CH_3$)COO—, —OCOCH($CH_3$)—$CH_2$—, or —$OCH_2CH_2O$—, provided that at least one $X^{ii1}$ represents —$CH_2$—$CH_2COO$—, —$OCOCH_2$—$CH_2$—, —CH═C($CH_3$)COO—, —OCOC($CH_3$)═CH—, —$CH_2$—CH($CH_3$)COO—, —OCOCH($CH_3$)—$CH_2$—, or —$OCH_2CH_2O$—, and $Y^{ii1}$ represents a single bond, —CH═CH—, —CF═CF—, —C≡C—, —COO—, —OCO—, —OCOO—, —OOCO—, —$CF_2O$—, —$OCF_2$—, —CH═CHCOO—, —OCOCH═CH—, —$CH_2$—$CH_2COO$—, —$OCOCH_2$—$CH_2$—, —CH═C($CH_3$)COO—, —OCOC($CH_3$)═CH—, —$CH_2$—CH($CH_3$)COO—, —OCOCH($CH_3$)—$CH_2$—, or an alkylene group having 2 to 20 carbon atoms, wherein one —$CH_2$— or two or more $CH_2$—'s not adjacent to each other in the alkylene group may be replaced with —O—, —COO—, or —OCO—.

12. A compound represented by general formula (ii-2):

(ii-2)

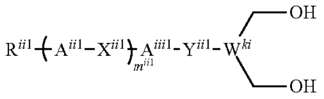

wherein $A^{ii1}$ and $A^{iii1}$ each represent the same meaning as $A^{i1}$, $m^{ii1}$ represents an integer of 2 to 4, $R^{ii1}$ represents a hydrogen atom, a linear or branched alkyl group having 1 to 40 carbon atoms, a halogenated alkyl group, $P^{i1}$-$Sp^{i1}$-, or wherein —$CH_2$— in the alkyl group may be replaced with —CH═CH—, —C≡C—, —O—, —NH—, —COO—, or —OCO—, provided that —O— moieties are not bonded in series, $W^{ki}$ represents a methine group, C—$CH_3$, or C—$C_2H_5$, $X^{ii1}$ represents a single bond, —CH═CH—, —CF═CF—, —C≡C—, —COO—, —OCO—, —OCOO—, —OOCO—, —$CF_2O$—, —$OCF_2$—, —CH═CHCOO—, —OCOCH═CH—, —$CH_2$—$CH_2COO$—, —$OCOCH_2$—$CH_2$—, —CH═C($CH_3$)COO—, —OCOC($CH_3$)═CH—, —$CH_2$—CH($CH_3$)COO—, —OCOCH($CH_3$)—$CH_2$—, or —$OCH_2CH_2O$—, provided that at least one $X^{ii1}$ represents —$CH_2$—$CH_2COO$—, —$OCOCH_2$—$CH_2$—, —CH═C(CH)COO—, —OCOC($CH_3$)═CH—, —$CH_2$—CH(CH)COO—, —OCOCH(CH)—$CH_2$—, or —$OCH_2CH_2O$—, and $Y^{ii1}$ represents a single bond, —CH═CH—, —CF═CF—, —C≡C—, —COO—, —OCO—, —OCOO—, —OOCO—, —$CF_2O$—, —$OCF_2$—, —CH═CHCOO—, —OCOCH═CH—, —$CH_2$—$CH_2COO$—, —$OCOCH_2$—$CH_2$—, —CH═C(CH)COO—, —OCOC(CH)═CH—, —$CH_2$—CH(CH)COO—, —OCOCH($CH_3$)—$CH_2$—, or an alkylene group having 2 to 20 carbon atoms, wherein one —$CH_2$— or two or more —$CH_2$—'s not adjacent to each other in the alkylene group may be replaced with —O—, —COO—, or —OCO—.

* * * * *